United States Patent
Van Baelen et al.

(10) Patent No.: US 9,631,220 B2
(45) Date of Patent: Apr. 25, 2017

(54) METHOD FOR DESIGNING A DRUG REGIME FOR HIV-INFECTED PATIENTS

(71) Applicant: JANSSEN DIAGNOSTICS BVBA, Beerse (BE)

(72) Inventors: Kurt Van Baelen, Westerlo (BE); Lieven Jozef Stuyver, Herzele (BE); Kevin Karel Florentina Arien, Nazareth (BE)

(73) Assignee: Janssen Diagnostics BVBA, Beerse (BE)

( * ) Notice: Subject to any disclaimer, the term of this patent is extended or adjusted under 35 U.S.C. 154(b) by 26 days.

(21) Appl. No.: 14/617,855

(22) Filed: Feb. 9, 2015

(65) Prior Publication Data

US 2015/0218611 A1 Aug. 6, 2015

Related U.S. Application Data

(62) Division of application No. 13/668,906, filed on Nov. 5, 2012, now abandoned, which is a division of application No. 12/524,120, filed as application No. PCT/EP2008/050778 on Jan. 23, 2008, now Pat. No. 8,338,101.

(30) Foreign Application Priority Data

Jan. 23, 2007 (EP) .................................. 07101037
Feb. 15, 2007 (EP) .................................. 07102423

(51) Int. Cl.
| | | |
|---|---|---|
| C12Q 1/68 | (2006.01) | |
| C12Q 1/02 | (2006.01) | |
| C12N 7/00 | (2006.01) | |
| C12Q 1/70 | (2006.01) | |
| C07H 21/04 | (2006.01) | |
| C07H 21/02 | (2006.01) | |

(52) U.S. Cl.
CPC ............ *C12Q 1/025* (2013.01); *C07H 21/04* (2013.01); *C12N 7/00* (2013.01); *C12Q 1/703* (2013.01); *C12N 2740/16021* (2013.01); *C12N 2740/16031* (2013.01); *C12N 2740/16043* (2013.01); *C12N 2740/16051* (2013.01); *G01N 2333/16* (2013.01); *G01N 2500/02* (2013.01); *G01N 2500/10* (2013.01)

(58) Field of Classification Search
CPC .......... C12N 2740/16021; C12N 2740/16031; C12N 2740/16043; C12N 2740/16051; C12N 7/00; C12Q 1/025; C12Q 1/703; G01N 2333/16; G01N 2500/02; G01N 2500/10
See application file for complete search history.

(56) References Cited

U.S. PATENT DOCUMENTS

| | | |
|---|---|---|
| 5,674,680 A | 10/1997 | Saksela et al. |
| 6,800,463 B1 | 10/2004 | Larder et al. |
| 6,852,491 B2 | 2/2005 | Harris et al. |
| 2003/0124514 A1 | 7/2003 | Vingerhoets et al. |
| 2009/0215028 A1* | 8/2009 | Paxinos ................ C12N 15/86 435/5 |

FOREIGN PATENT DOCUMENTS

| | | |
|---|---|---|
| WO | WO 9727319 A1 | 7/1997 |
| WO | WO 01/79540 A2 | 10/2001 |
| WO | WO 01/81624 A1 | 11/2001 |
| WO | WO 02/23186 | 3/2002 |
| WO | WO 02/33402 | 4/2002 |
| WO | WO 2007/118849 A2 | 10/2007 |
| WO | WO 2008/090185 A1 | 7/2008 |

OTHER PUBLICATIONS

Boom, et al., "Rapid and simple method for purification of nucleic acids", J. Clin. Microbial., Mar. 1990, 28(3), 495-503.
Buck, et al., "Design strategies and performance of custom DNA sequencing primers", BioTechniques, Sep. 1999, vol. 27, pp. 528-536.
Fikkert, et al. "Development of Resistance Against Diketo Derivatives of Human Immunodeficiency Virus Type 1 by Progressive Accumulation of Integrase Mutations", Journal of Virology, vol. 77, No. 21, Nov. 2003, pp. 11459-11470.
GenBank Accession No. A24304, "Human immunodeficiency virus type 1 (HIV-1)", Mar. 15, 1995, 1 page.
GenBank Accession No. AF178660, "Human immunodeficiency virus type 1 (HIV-1)", May 8, 2001, 1 page.
GenBank Accession No. AY840284, "Human immunodeficiency virus type 1 (HIV-1)", Jan. 23, 2005, 1 page.
GenBank Accession No. HC022486, "Human immunodeficiency virus" Dec. 8, 2009, 1 page.
GenBank Accession No. K03455, "Human immunodeficiency virus type 1 (HXB2), complete gnome", Oct. 21, 2002, 8 pages.
Hertogs, et al. "A Rapid Method for Simultaneous Detection of Phenotypic Resistance to Inhibitors of Protease and Reverse Transcriptase in Recombinant Human Immunodeficiency Virus Type 1 Isolates from Patients Treated with Antiretroviral Drugs", Antimicrobial Agents and Chemotherapy, American Society for Microbiology, vol. 42, No. 2, Feb. 1998, pp. 269-276.
Kellam et al., "Recombinant virus assay: a rapid, phenotypic assay for assessment of drug susceptibility of human immunodeficiency virus type 1 isolates", Antimicrob Agents Chemother., Jan. 1994, 38(1), pp. 23-30.

(Continued)

Primary Examiner — Teresa Strzelecka
(74) Attorney, Agent, or Firm — Baker & Hostetler LLP

(57) ABSTRACT

The instant disclosure describes a novel genotype and phenotype assay to elucidate and/or evaluate new potential HIV integrase inhibitors, but also currently approved and experimental compounds that target protease, reverse transcriptase, and RNaseH. This assay allows studying linked mutations and mutational patterns that occur under HAART and experimental therapies.

2 Claims, 25 Drawing Sheets

(56) References Cited

OTHER PUBLICATIONS

Lee, et. al. "Human Immunodeficiency virus Type 1 (HIV-1) Integrase: Resistance to Diketo Acid Integrase Inhibitors Impairs HIV-1 Replication and Integratin and Confers Cross-Resistance to L-Chicoric Acid", Journal of Virology, vol. 78, No. 11, Jun. 2004, pp. 5835-5847.
Maguire, et al., "Changes in Human Immunodeficiency Virus Type 1 Gag at Positions L449 and P453 are Linked to I50V Protease Mutants In Vivo and Cause Reduction of Sensitivity to Amprenavir and Improved Viral Fitness in Vitro", Journal of Virology 2002, vol. 76(15), pp. 7398-7406.
Pauwels, et al., "Rapid and Automated Tetrazolium-Based Colorimetric Assay for the Detection of Anti-HIV Compounds", J. Viral. Methods, Mar. 30, 988, 20, pp. 309-321.
Petropoulos, et al. "A Novel Phenotypic Drug Susceptibility Assay for Human Immunodeficiency Virus Type 1", Antimicrobial Agents and Chemotherapy, American Society for Microbiology, vol. 44, No. 4, Apr. 2000, pp. 920-928.
Ratner et al., "Complete nucleotide sequence of the AIDS virus, HTLV-111", Jan. 1985, vol. 313, p. 277-284.
Shafer, et al., "Human Immunodeficiency Virus Reverse Transcriptase and Protease Sequence Database", Nucleic Acids Research, Oxford University Press, Surrey, GB, vol. 27, No. 1, Jan. 1, 1999, pp. 348-352.

* cited by examiner

Vector: Delta(Gag-Pol)

FIG. 1A. Digest pUC18 with PstI and EcoRI

461 - GCTTGCATGC CTGCAGGTCG ACTCTAGAGG ATCCCCGGGT ACCGAGCTC GAATTCGTAAT CATGGTCATA - 471
       PstI                                                    EcoRI
                              - 35 nt                                      SEQ ID NO:59

FIG 1B. Ligate linker into pUC18

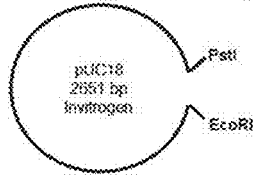

PstI     HpaI      SpeI       SalI      EcoRI
- CTGCAG ACAC  GTTAACACAC  ACTAGTACAC  GTCGACACA  GAATTC -    SEQ ID NO:60
- GACGTCTGTG  CAATTGTGTG  TGATCATGTG  CAGCTGTGT  CTTAAG -
                              + 35 nt

FIG. 1C. Digest pUC18-LINK with HpaI and SalI

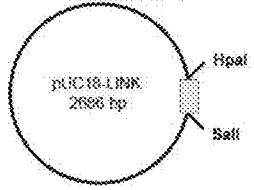

HpaI                     SalI
- CTGCAG ACAC  GTTAAC  ACAC ACTAGT ACAC  GTCGAC ACAC GAATTC -   SEQ ID NO:61
- GACGTCTGTG  CAATTGTGTG  TGATCATGTG  CAGCTGTGTG  CTTAAG -
                              Linker FIG. 1D. Ligate fragment A into pUC18-LINK

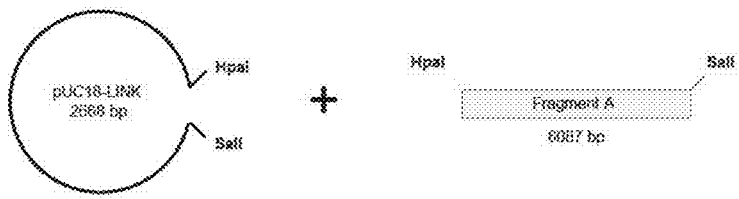

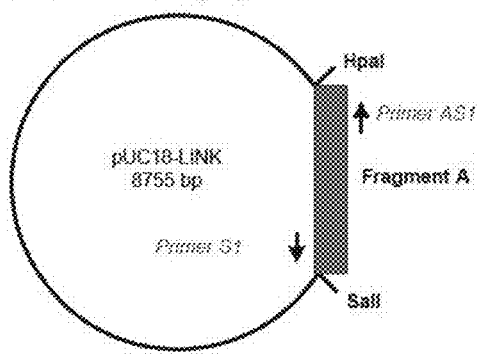
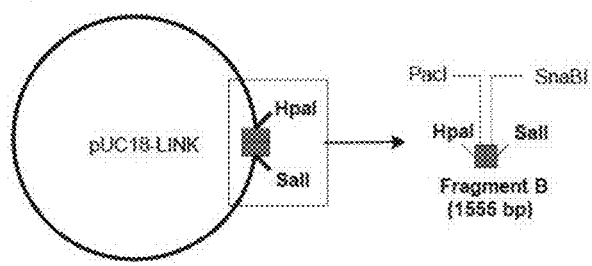
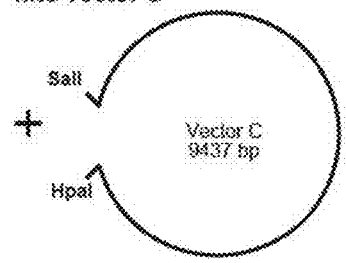
Figure 1: Creation of delta[GAG-POL] backbone based on the HXB2D_eGFP HIV-1 vector.

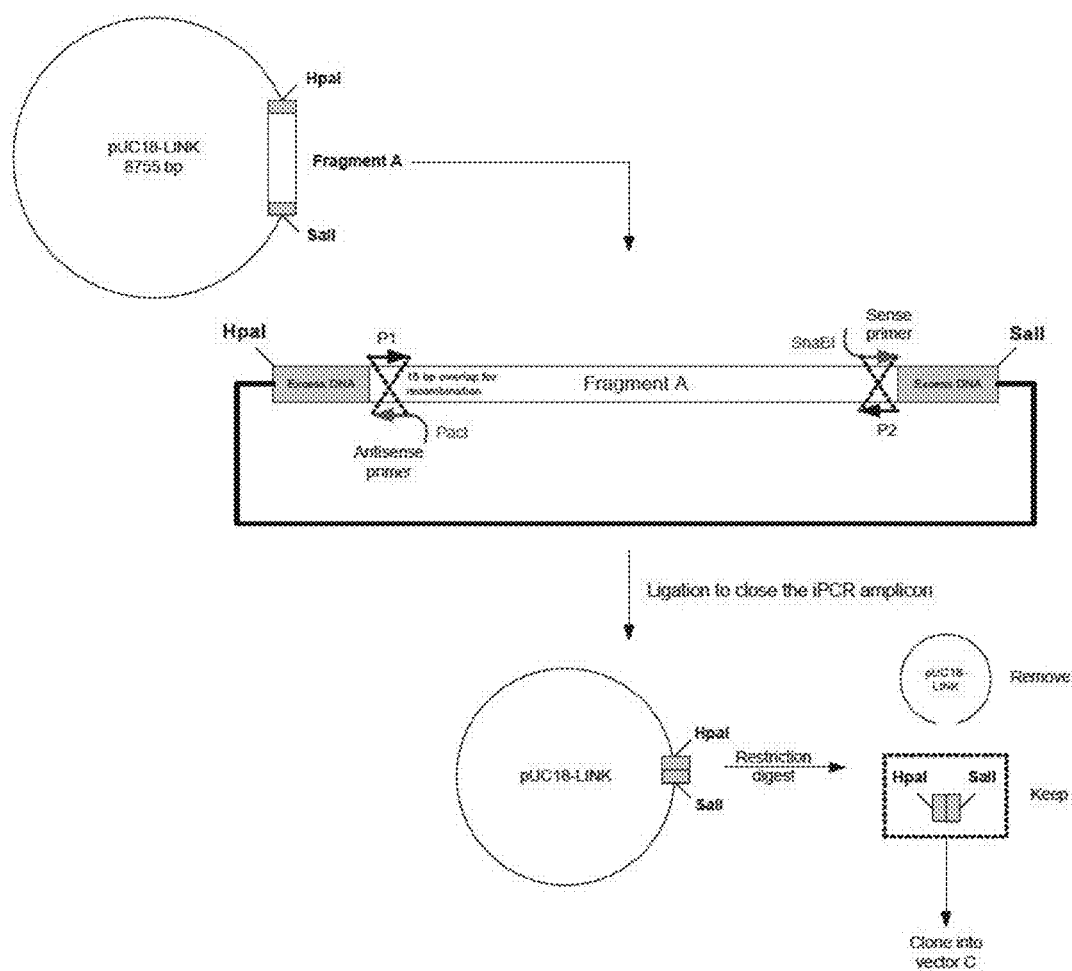
Figure 2: Detailed description of the 'inverse PCR' reaction.

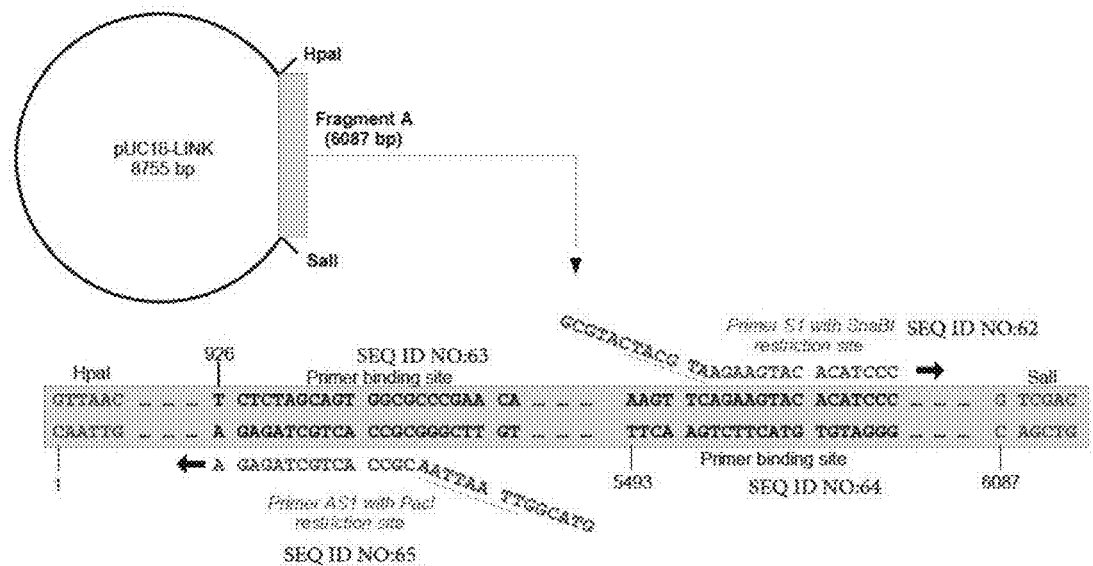
Figure 3 : Primers for 'inverse PCR' containing the PacI and SnaBI restriction sites.

Vector : Delta[RT-INT]

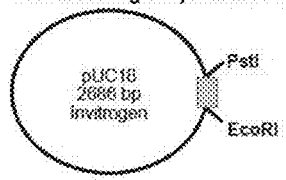

FIG. 4A. Digest pUC18 with PstI and EcoRI

461 - GCTTGCATGC CTGCAG GTCG ACTCTAGAGG ATCCCCGGGT ACCGAGCTC G AATTC GTAAT CATGGTCATA - 471
                  PstI              - 35 nt                    EcoRI
                                                                             SEQ ID NO:59

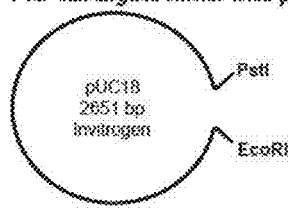

FIG 4B. Ligate linker into pUC18

```
          PstI        HpaI         SpeI         SalI         EcoRI
- CTGCAG ACAC  GTTAAC ACAC  ACTAGT ACAC  GTCGAC ACA  GAATTC -   SEQ ID NO:60
- GACGTC TGTG  CAATTG TGTG  TGATCA TGTG  CAGCTG TGT  CTTAAG -
                                  + 35 nt
```

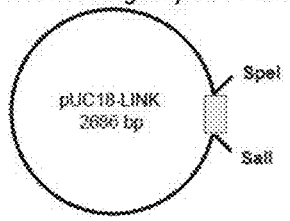

FIG. 4C. Digest pUC18-LINK with SpeI and SalI

```
                              SpeI          SalI
- CTGCAGACAC  GTTAAC ACAC  ACTAGT ACAC  GTCGAC ACAC  GAATTC -  SEQ ID NO:61
- GACGTCTGTG  CAATTG TGTG  TGATCA TGTG  CAGCTG TGTG  CTTAAG -
                                Linker
```

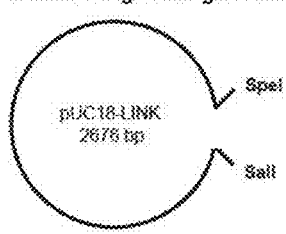

FIG. 4D. Ligate fragment X into pUC18-LINK

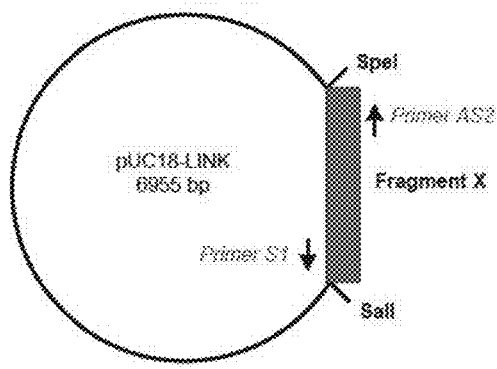
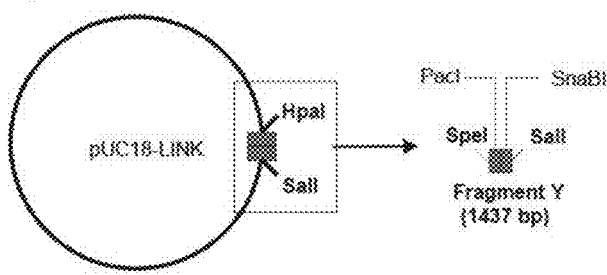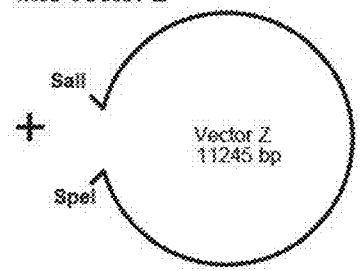
Figure 4: Creation of delta[RT-INT] backbone based on the HXB2D_eGFP HIV-1 vector.

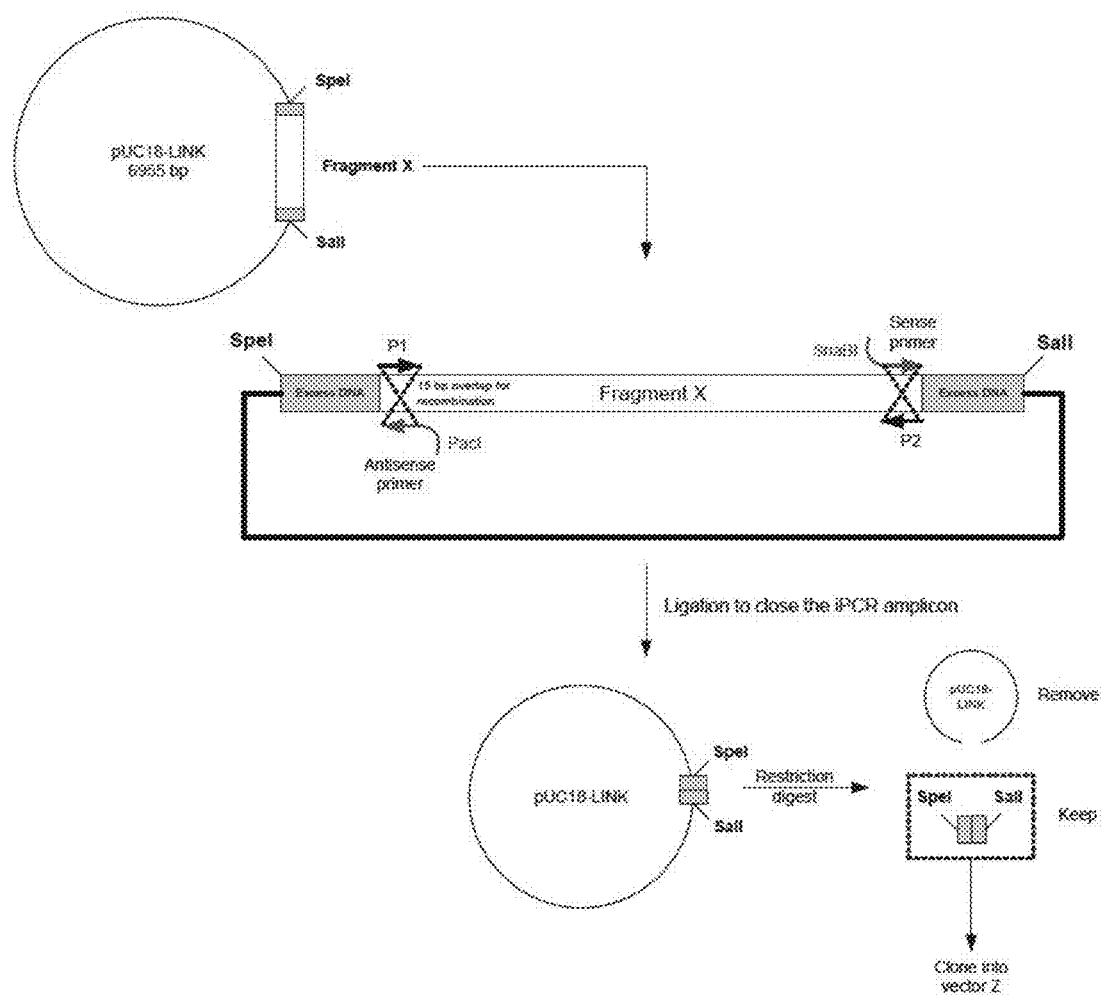
Figure 5: Detailed description of the 'inverse PCR' reaction.

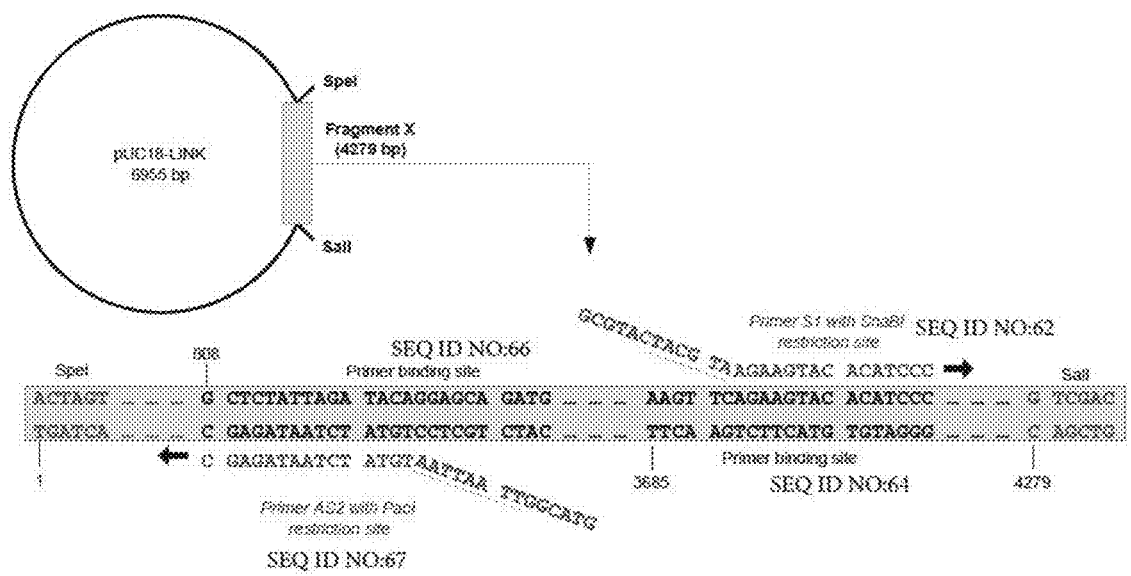
Figure 6: Primers for 'inverse PCR' containing the PacI and SnaBI restriction sites Vector : Delta[Gag-Pr]

FIG. 7A. Digest pUC18 with PstI and EcoRI

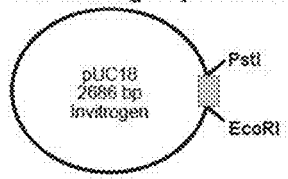

401 - GCTTGCATGC CTGCAGGTCG ACTCTAGAGG ATCCCCGGGT ACCGAGCTCG AATTCGTAAT CATGGTCATA - 471
         PstI                                                      EcoRI
                          - 35 nt                                              SEQ ID NO:59

FIG 7B. Ligate linker into pUC18

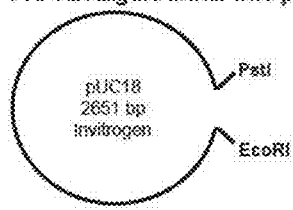

PstI        HpaI         SpeI        SalI        EcoRI
- CTGCAGACAC GTTAACACAC ACTAGTACAC GTCGACACA GAATTC - SEQ ID NO:60
- GACGTCTGTG CAATTGTGTG TGATCATGTG CAGCTGTGT CTTAAG -
                          + 35 nt

FIG. 7C. Digest pUC18-LINK with HpaI and SalI

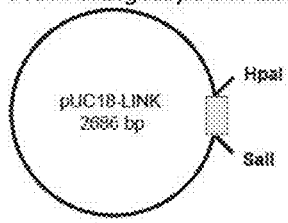

HpaI                        SalI
- CTGCAG ACAC GTTAAC ACAC ACTAGT ACAC GTCGAC ACAC GAATTC - SEQ ID NO:61
- GACGTCTGTG CAATTGTGTG TGATCATGTG CAGCTGTGTG CTTAAG -
                              Linker

FIG. 7D. Ligate fragment A into pUC18-LINK

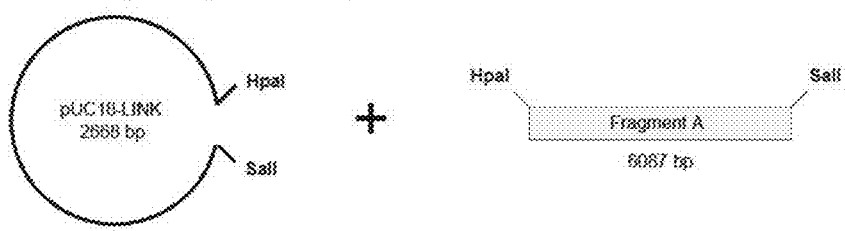

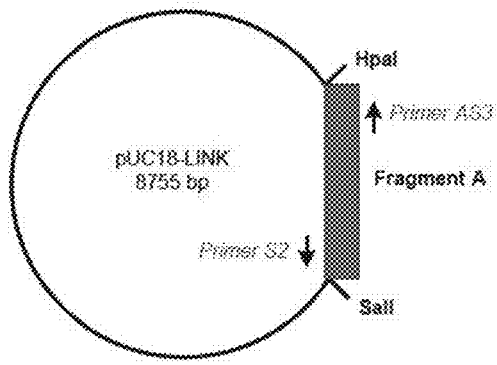
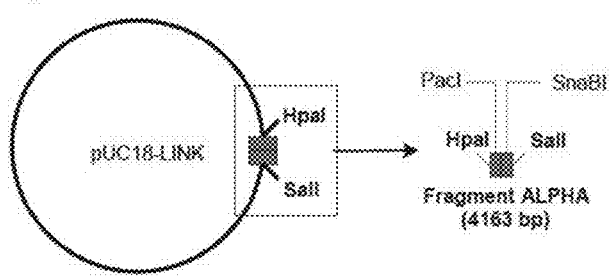 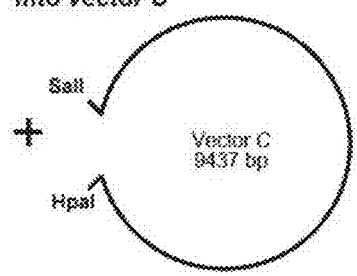
Figure 7: Creation of delta[GAG-PR] backbone based on the HXB2D_eGFP HIV-1 vector.

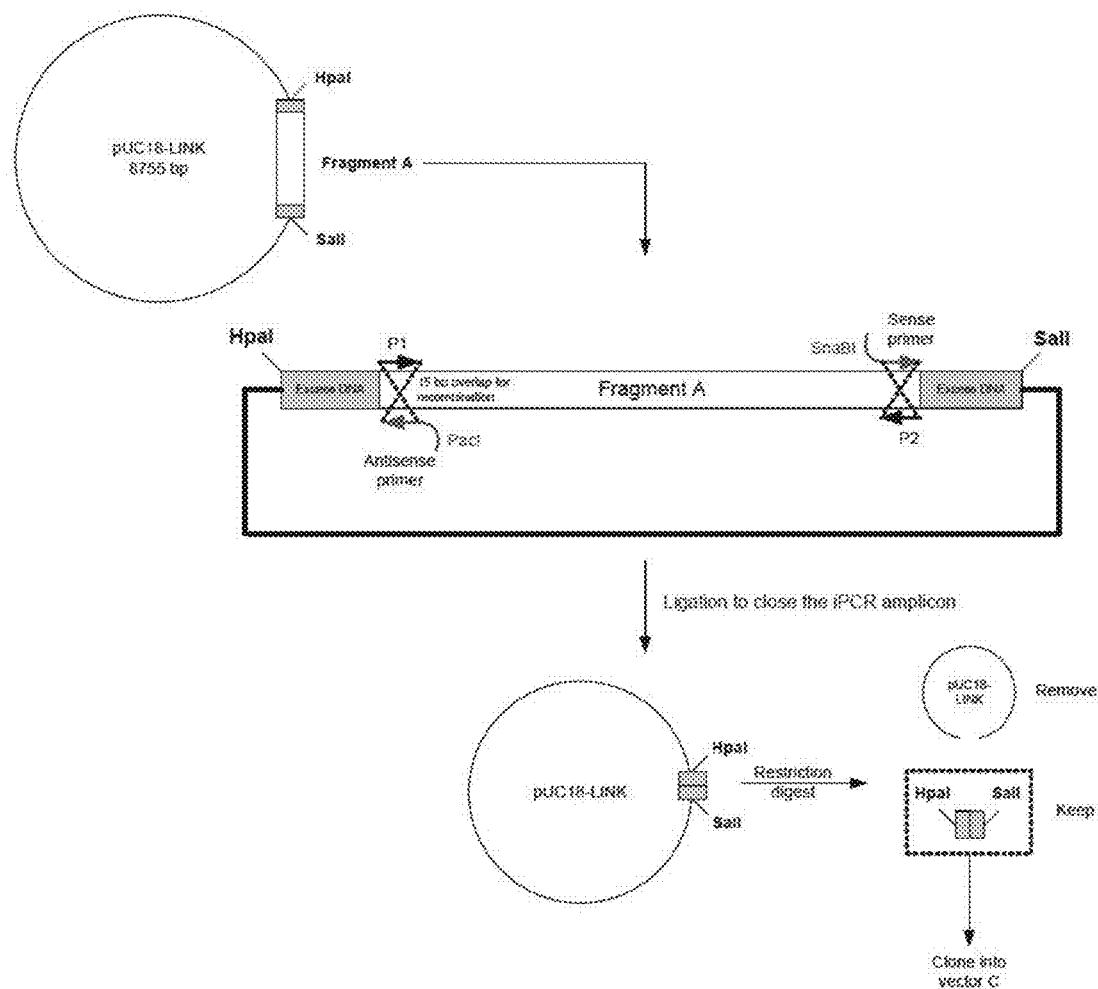
Figure 8: Detailed description of the 'inverse PCR' reaction.

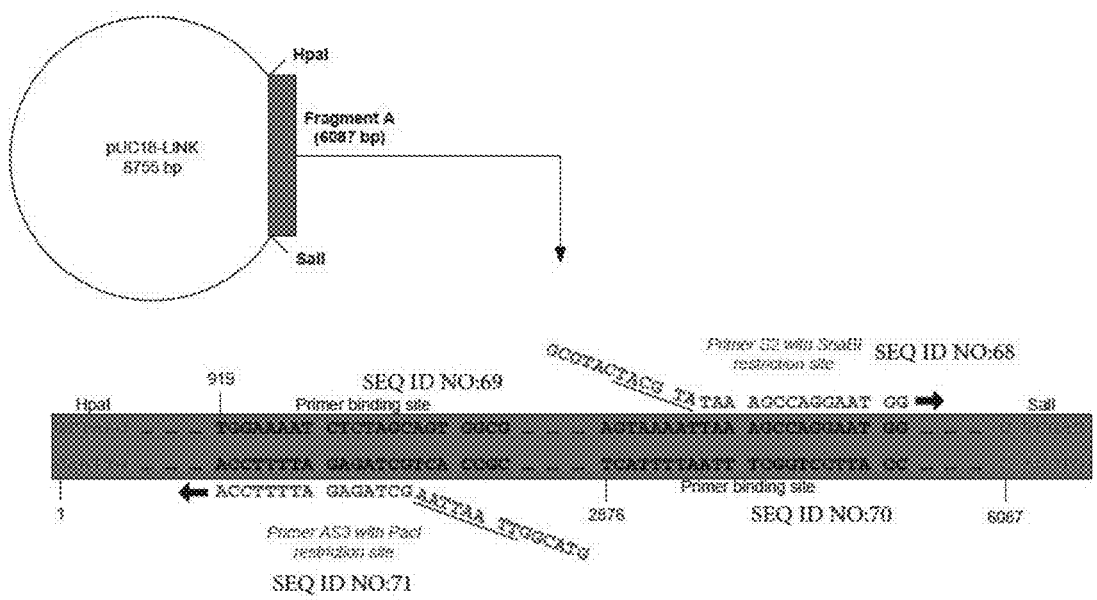
Figure 9 : Primers for 'inverse PCR' containing the PacI and SnaBI restriction sites

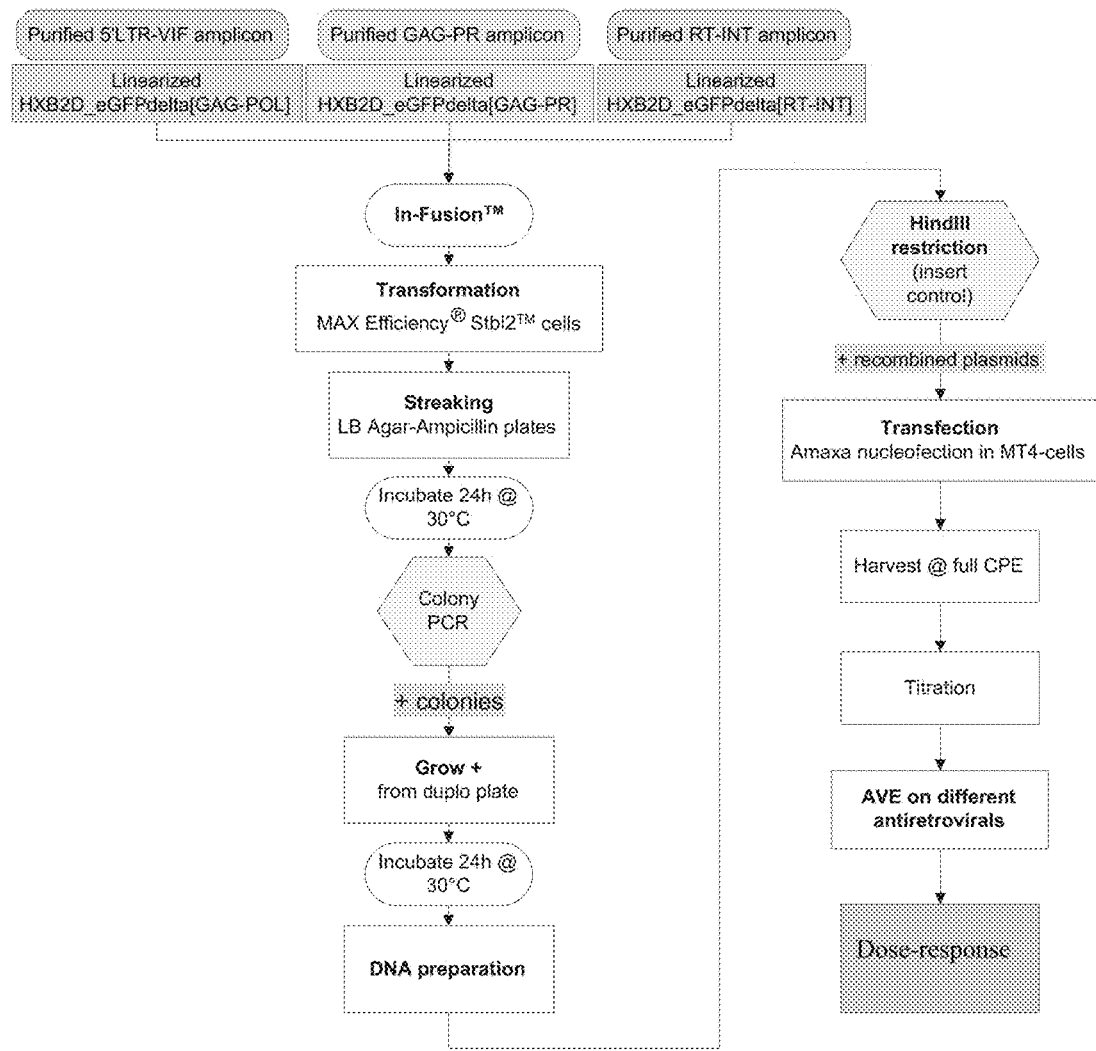
Figure 10: Phenotypic process flow

Figure 11: Dose-response curves for 1 GAG-POL recombinant virus stock.

Atazanavir

Saquinavir

PA457

Indinavir

Ritonavir

Nevirapine

Nelfinavir

Lamivudine

Tipranavir

Abacavir

Lopinavir

GS9137

Zidovudine

Amprenavir

Merck L870,810

Merck L731,988

Vector : Delta(Pol)

FIG. 12A. Digest pUC18 with PstI and EcoRI

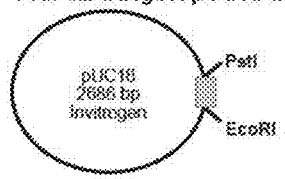

401 - GCTTGCATGC CTGCAGGTCG ACTCTAGAGG ATCCCCGGGT ACCGAGCTCG AATTCGTAAT CATGGTCATA - 471
　　　　　　　　PstI　　　　　　　　　　　　　－ 35 nt　　　　　　　　　EcoRI
　　　　　　　　　　　　　　　　　　　　　　　　　　　　　　　　　　　　　　　　SEQ ID NO:59

FIG 12B. Ligate linker into pUC18

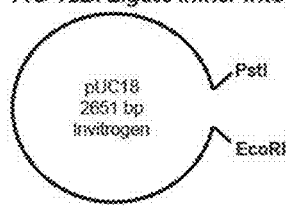

PstI　　　　　Hpal　　　　　Spel　　　　　Sall　　　　　EcoRI
　　　　　- CTGCAG ACAC GTTAAC ACAC ACTAGT ACAC GTCGAC ACAC GAATTC - SEQ ID NO:60
　　　　　- GACGTCTGTG CAATTGTGTG TGATCATGTG CAGCTGTGT CTTAAG -
　　　　　　　　　　　　　　　　　　　+ 35 nt

FIG. 12C. Digest pUC18-LINK with HpaI and SalI

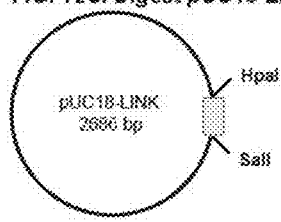

Hpal　　　　　　　　　　　　　Sall
　　　　- CTGCAG ACAC GTTAAC ACAC ACTAGT ACAC GTCGAC ACAC GAATTC - SEQ ID NO:61
　　　　- GACGTCTGTG CAATTGTGTG TGATCATGTG CAGCTGTGTG CTTAAG -
　　　　　　　　　　　　　　　　　　　Linker

FIG. 12D. Ligate fragment A into pUC18-LINK

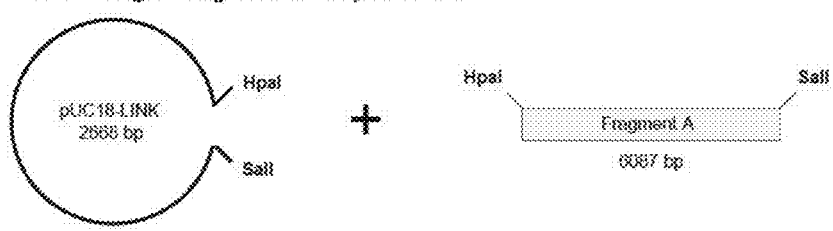

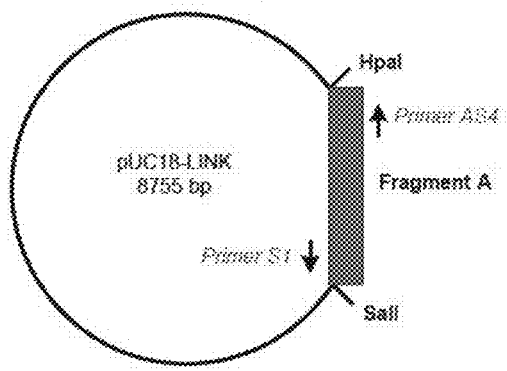
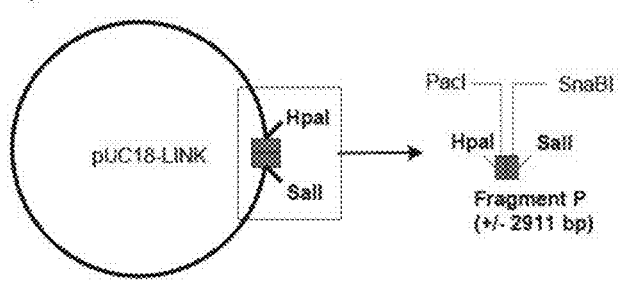
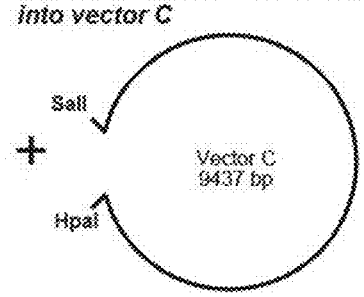
Figure 12: Creation of delta[POL] backbone based on the HXB2D_eGFP HIV-1 vector.

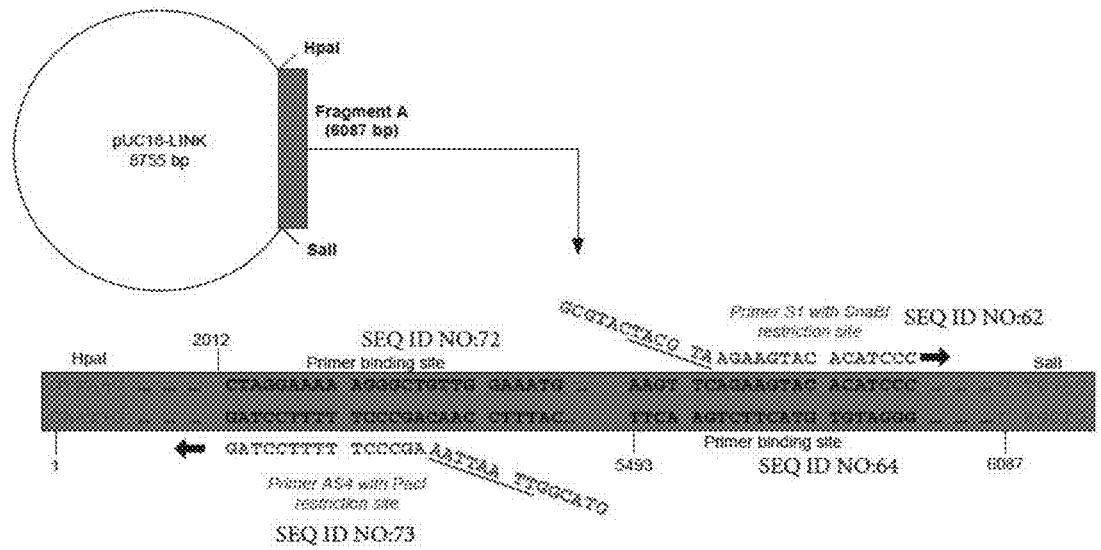
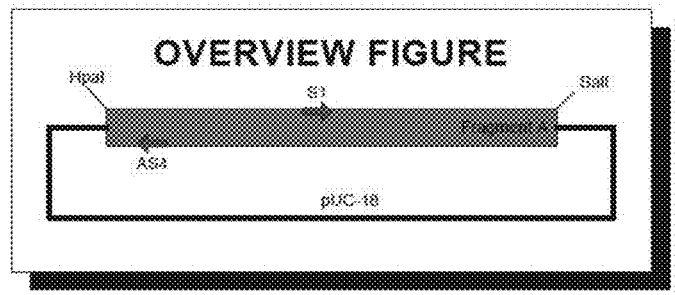
Figure 13. Primers for 'inverse PCR' containing the PacI and SnaBI restriction sites.

METHOD FOR DESIGNING A DRUG REGIME FOR HIV-INFECTED PATIENTS

CROSS REFERENCE TO RELATED APPLICATIONS

This application is a divisional application of U.S. application Ser. No. 13/668,906, filed Nov. 5, 2012, which is a divisional application of U.S. application Ser. No. 12/524,120, filed Jul. 22, 2009, now U.S. Pat. No. 8,338,101, issued Dec. 25, 2012, which is the national stage of PCT Application No. PCT/EP2008/050778 filed Jan. 23, 2008, which claims priority from European Patent Application No. 07102423.6, filed Feb. 15, 2007, and European Patent Application No. 07101037.5, filed 23 Jan. 2007, the entire disclosures of which are hereby incorporated by reference in their entirety.

BACKGROUND

Millions and millions of people have been infected with the human immunodeficiency virus ("HIV"), the causative agent of acquired immune deficiency syndrome ("AIDS"), since the early 1980s. HIV/AIDS is now the leading cause of death in sub-Saharan Africa, and is the fourth biggest killer worldwide. At the end of 2001, an estimated 40 million people were living with HIV globally.

Currently, five classes of antiretroviral drugs are used to treat infection by Human Immunodeficiency Virus (HIV), i.e. protease inhibitors (PIs), two classes of reverse transcriptase inhibitors (nucleoside reverse transcriptase inhibitors abbreviated as N RTI and non-nucleoside reverse transcriptase inhibitors abbreviated as NN-RTI), entry inhibitors (fusion inhibitors (FIs) and co-receptor antagonists), and integrase inhibitors (INIs). Integrase inhibitors are a promising new class of antiretrovirals interfering with HIV replication by blocking the ability of the virus to integrate into the genetic material of human cells.

Modern anti-HIV drugs target different stages of the HIV life cycle and a variety of enzymes essential for HIV's replication and/or survival. Amongst the drugs that have so far been approved for AIDS therapy are nucleoside reverse transcriptase inhibitors ("NRTIs") such as AZT, ddl, ddC, d4T, 3TC, and abacavir; nucleotide reverse transcriptase inhibitors such as tenofovir; non-nucleoside reverse transcriptase inhibitors ("NNRTIs") such as nevirapine, efavirenz, and delavirdine; protease inhibitors ("PIs") such as darunavir, saquinavir, ritonavir, indinavir, nelfinavir, amprenavir, lopinavir and atazanavir; fusion inhibitors, such as enfuvirtide, co-receptor antagonists such as maraviroc and integrase inhibitors such as raltegravir.

Nonetheless, in the vast majority of subjects none of the antiviral drugs currently approved, either alone or in combination, proves effective either to prevent eventual progression of chronic HIV infection to AIDS or to treat acute AIDS. This phenomenon is due, in part, to the high mutation rate of HIV and the rapid emergence of mutant HIV that are resistant to antiviral therapeutics upon administration of such drugs to infected individuals.

The integrase protein thus represents an interesting target for HIV inhibitor research. HIV integrase is required for integration of the viral genome into the genome of the host cell, a step in the replicative cycle of the virus. HIV integrase is a protein of about 32 KDa encoded by the pol gene, and is produced in vivo by protease cleavage of the gag-pol precursor protein during the production of viral particles. The integration process takes place following reverse transcription of the viral RNA. First, the viral integrase binds to the viral DNA and removes two nucleotides from the 3' end of the viral long-terminal repeat (LTR) sequences on each strand. This step is called 3' end processing and occurs in the cytoplasm within a nucleoprotein complex termed the pre-integration complex (PIC). Second, in a process called strand transfer, the two strands of the cellular DNA into which the viral DNA will be inserted, the target DNA, is cleaved in a staggered fashion. The 3' ends of the viral DNA are ligated to the 5' ends of the cleaved target DNA. Finally, host enzymes probably repair remaining gaps.

With the increasing number of available anti-HIV compounds as mentioned above, the number of potential treatment protocols for HIV infected patients will continue to increase. Many of the currently available compounds are administered as part of a combination therapy. The high complexity of treatment options coupled with the ability of the virus to develop resistance to HIV inhibitors requires the frequent assessment of treatment strategies. The ability to accurately monitor the replicative capacity of virus in patients with a drug regimen and to use that data to modify the doses or combinations of inhibitors allows physicians to effectively reduce the formation of drug resistant virus and provide an optimal, tailored treatment for each patient.

Accordingly, as new drugs targeting new HIV polypeptides become available, phenotypic and genotypic assays for determining resistance or susceptibility of HIV infecting a patient to such new anti-HIV drugs are highly needed.

While phenotyping and genotyping assays have been developed and marketed for reverse transcriptase and protease genes, protocols and assays for evaluation of drug resistance against the integrase gene have not been successfully developed.

For instance, the amplicon used in the marketed Antivirogram® contains the gag cleavage sites (p1/p7 and p1/p6), PR (codon 1-99) and RT (codon 1-400) coding sequences respectively, leaving the rest of the relevant HIV reverse transcriptase gene and more importantly the HIV integrase gene undetected.

SUMMARY

The instant disclosure describes a novel genotype and phenotype assay to elucidate and/or evaluate new HIV integrase inhibitors, but also currently approved and experimental compounds that target maturation, protease, reverse transcriptase, and RNaseH. This assay allows studying linked mutations and mutational patterns that occur under HAART and experimental therapies. The selection of the primers used for the preparation of the appropriate amplicon is, due to the mutations and mutational patterns present in the HIV sequence, of the utmost importance to further develop a reliable and sensitive genotype and phenotype assay.

BRIEF DESCRIPTION OF THE DRAWINGS

FIG. 1 shows a schematic representation for creating the GAG-POL vector backbone based on the HXB2D_eGFP HIV-1 vector. Subparts 1A-1D, 1F, and 1G illustrate certain digestion/ligation vector manipulations, while subpart 1E depicts PCR amplification of Fragment A.

FIG. 2 provides a more detailed schematic representation of the inverse PCR described for creating the GAG-POL vector backbone based on the HXB2D_eGFP HIV-1 vector.

FIG. 3 depicts the primer binding sites for the inverse PCR described for creating the GAG-POL vector backbone based on the HXB2D_eGFP HIV-1 vector.

FIG. 4 shows a schematic representation for creating the RT-INT vector backbone based on the HXB2D_eGFP HIV-1 vector. Subparts 4A-4D, 4F, and 4G illustrate certain digestion/ligation vector manipulations, while subpart 4E depicts PCR amplification of Fragment X.

FIG. 5 provides a more detailed schematic representation of the inverse PCR described for creating the RT-INT vector backbone based on the HXB2D_eGFP HIV-1 vector.

FIG. 6 depicts the primer binding sites for the inverse PCR described for creating the RT-INT vector backbone based on the HXB2D_eGFP HIV-1 vector.

FIG. 7 shows a schematic representation for creating the GAG-PR vector backbone based on the HXB2D_eGFP HIV-1 vector. Subparts 7A-7D, 7F, and 7G illustrate certain digestion/ligation vector manipulations, while subpart 7E depicts PCR amplification of Fragment A.

FIG. 8 provides a more detailed schematic representation of the inverse PCR described for creating the GAG-PR vector backbone based on the HXB2D_eGFP HIV-1 vector.

FIG. 9 depicts the primer binding sites for the inverse PCR described for creating the GAG-PR vector backbone based on the HXB2D_eGFP HIV-1 vector.

FIG. 10 is a flow chart summarizing an experimental process for determining the phenotype of viruses produced using a GAG-POL, GAG-PR or RT-INT vector.

FIG. 12 shows a schematic representation for creating the delta[POL] vector backbone based on the HXB2D_eGFP HIV-1 vector. Subparts 12A-12D, 12F, and 12G illustrate certain digestion/ligation vector manipulations, while subpart 12E depicts PCR amplification of Fragment A.

FIG. 13 depicts the primer binding sites for the inverse PCR described for creating the delta[POL] vector backbone based on the HXB2D_eGFP HIV-1 vector.

DETAILED DESCRIPTION OF ILLUSTRATIVE EMBODIMENTS

Figure 11A:
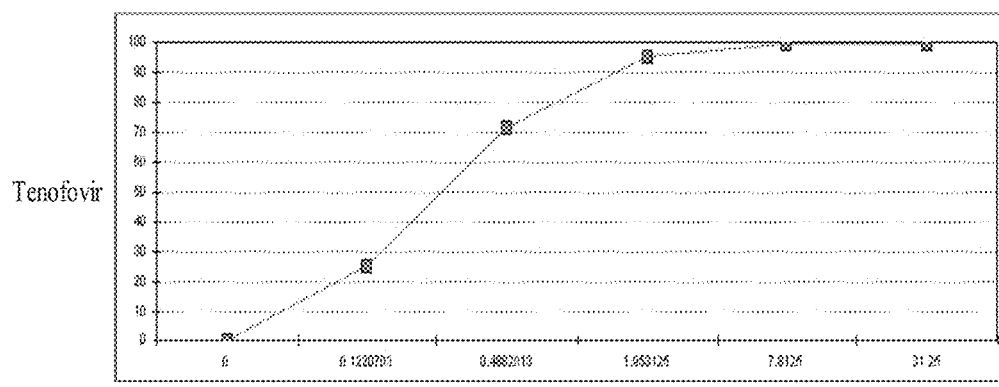
FIGS. 11A-11R show the dose-response curves 1 GAG-POL RVS for all drugs tested.

In contrast to the amplicon mentioned above as used in the Antivirogram, the amplicon described in the instant invention and referred to as 5' LTR-Vif fragment contains the complete gag and complete pol (PR-RT-INT) coding region (4588 bp in HXB2D, GenBank accession number K03455).

Gag is the Group-specific Antigen protein, encoding the structural capsid proteins. The proteins are produced as a GAG precursor polyprotein, which is processed by the viral protease.

Other amplicons used in the current invention are the amplicon spanning the Gag cleavage sites p1/p7 and p1/p6, PR, RT, RNaseH and INT (3202 bp), referred to as Pol fragment, the amplicon containing the Gag and PR coding sequence (1980 bp), referred to as Gag-PR fragment, and the amplicon containing the complete RT, RNaseH and INT coding sequence (2898 bp), named RT-INT fragment.

The current disclosure describes an in vitro method for designing a drug regimen for an HIV-infected patient by determining the phenotypic susceptibility of HIV to at least one drug, comprising:

i) using at least one sample comprising HIV RNA from a patient, wherein the sample comprises the complete HIV gag-pol coding region;

ii) reverse-transcribing and amplifying the HIV RNA with primers specific for the complete HIV gag-pol coding region to obtain at least one amplicon comprising the complete HIV gag-pol coding region, wherein at least one primer is selected from SEQ ID NO: 1-4;

iii) generating a plasmid comprising a reference HIV sequence with a deletion of the complete HIV gag-pol coding region;

iv) preparing at least one recombinant virus by recombination or ligation between at least one amplicon obtained in step ii) and the plasmid comprising the reference HIV sequence with a deletion of the complete HIV gag-pol coding region obtained in step iii), and v) monitoring the at least one recombinant virus in the presence of the at least one drug to determine the phenotypic susceptibility of HIV to at least one drug, wherein said susceptibility is determined by the cytopathogenicity of said recombinant virus to cells or by determining the replicative capacity of said recombinant virus in the presence of at least one drug.

The instant disclosure describes an in vitro method for designing a drug regimen for an HIV-infected patient by determining the phenotypic susceptibility of HIV to at least one drug, comprising:

i) using at least one sample comprising HIV RNA from a patient, wherein the sample comprises the region spanning the HIV gag-protease coding sequence;

ii) reverse-transcribing and amplifying the HIV RNA with primers specific for the region spanning the HIV gag-protease coding sequence to obtain at least one amplicon comprising the region spanning the HIV gag-protease coding sequence, wherein at least one primer is selected from SEQ ID NO: 1 and SEQ ID NO: 8-10;

iii) generating a plasmid comprising a reference HIV sequence with a deletion of the region spanning the HIV gag-protease coding sequence;

iv) preparing at least one recombinant virus by recombination or ligation between at least one amplicon obtained in step ii) and the plasmid comprising the reference HIV sequence with a deletion of the region spanning the HIV gag-protease coding sequence obtained in step iii), and v) monitoring the at least one recombinant virus in the presence of the at least one drug to determine the phenotypic susceptibility of HIV to at least one drug, wherein said susceptibility is determined by the cytopathogenicity of said recombinant virus to cells or by determining the replicative capacity of said recombinant virus in the presence of at least one drug.

Furthermore the present disclosure also comprises an in vitro method for designing a drug regimen for an HIV-infected patient by determining the phenotypic susceptibility of HIV to at least one drug, comprising:

i) using at least one sample comprising HIV RNA from a patient, wherein the sample comprises the complete HIV reverse transcriptase-integrase coding sequence;

ii) reverse-transcribing and amplifying the HIV RNA with primers specific for the complete HIV reverse transcriptase-integrase coding sequence to obtain at least one amplicon comprising the complete HIV reverse transcriptase-integrase coding sequence, wherein at least one primer is selected from SEQ ID NO: 4-7;

iii) generating a plasmid comprising a reference HIV sequence with a deletion of the complete HIV reverse transcriptase-integrase coding sequence;

iv) preparing at least one recombinant virus by recombination or ligation between at least one amplicon obtained in step ii) and the plasmid comprising the reference HIV sequence with a deletion of the complete HIV reverse transcriptase-integrase coding sequence obtained in step iii), and v) monitoring the at least one recombinant virus in the presence of the at least one drug to determine the phenotypic susceptibility of HIV to at least one drug, wherein said susceptibility is determined by the cytopathogenicity of said recombinant virus to cells or by determining the replicative capacity of said recombinant virus in the presence of at least one drug.

The current invention also applies to an in vitro method for designing a drug regimen for an HIV-infected patient by determining the phenotypic susceptibility of HIV to at least one drug, comprising:

i) using at least one sample comprising HIV DNA, wherein the sample comprises the complete HIV gag-pol coding region;

ii) amplifying the HIV DNA with primers specific for the complete HIV gag-pol coding region to obtain at least one amplicon comprising the complete HIV gag-pol coding region, wherein at least one primer is selected from SEQ ID NO: 1-4;

iii) generating a plasmid comprising a reference HIV sequence with a deletion of the complete HIV gag-pol coding region;

iv) preparing at least one recombinant virus by recombination or ligation between at least one amplicon obtained in step ii) and the plasmid comprising the reference HIV sequence with a deletion of the complete HIV gag-pol coding region obtained in step iii), and v) monitoring the at least one recombinant virus in the presence of the at least one drug to determine the phenotypic susceptibility of HIV to at least one drug, wherein said susceptibility is determined by the cytopathogenicity of said recombinant virus to cells or by determining the replicative capacity of said recombinant virus in the presence of at least one drug.

In addition the disclosure describes an in vitro method for designing a drug regimen for an HIV-infected patient by determining the phenotypic susceptibility of HIV to at least one drug, comprising:

i) using at least one sample comprising HIV DNA, wherein the sample comprises the region spanning the HIV gag-protease coding sequence;

ii) amplifying the HIV DNA with primers specific for the region spanning the HIV gag-protease coding sequence to obtain at least one amplicon comprising the region spanning the HIV gag-protease coding sequence, wherein at least one primer is selected from SEQ ID NO: 1 and SEQ ID NO: 8-10;

iii) generating a plasmid comprising a reference HIV sequence with a deletion of the region spanning the HIV gag-protease coding sequence;

iv) preparing at least one recombinant virus by recombination or ligation between at least one amplicon obtained in step ii) and the plasmid comprising the reference HIV sequence with a deletion of the region spanning the HIV gag-protease coding sequence obtained in step iii), and v) monitoring the at least one recombinant virus in the presence of the at least one drug to determine the phenotypic susceptibility of HIV to at least one drug, wherein said susceptibility is determined by the cytopathogenicity of said recombinant virus to cells or by determining the replicative capacity of said recombinant virus in the presence of at least one drug.

The disclosure also comprises an in vitro method for designing a drug regimen for an HIV-infected patient by determining the phenotypic susceptibility of HIV to at least one drug, comprising:

i) using at least one sample comprising HIV DNA, wherein the sample comprises the complete HIV reverse transcriptase-integrase coding sequence;

ii) amplifying the HIV DNA with primers specific for the complete HIV reverse transcriptase-integrase coding sequence to obtain at least one amplicon comprising the complete HIV reverse transcriptase-integrase coding sequence, wherein at least one primer is selected from SEQ ID NO: 4-7;

iii) generating a plasmid comprising a reference HIV sequence with a deletion of the complete HIV reverse transcriptase-integrase coding sequence;

iv) preparing at least one recombinant virus by recombination or ligation between at least one amplicon obtained in step ii) and the plasmid comprising the reference HIV sequence with a deletion of the complete HIV reverse transcriptase-integrase coding sequence obtained in step iii), and v) monitoring the at least one recombinant virus in the presence of the at least one drug to determine the phenotypic susceptibility of HIV to at least one drug, wherein said susceptibility is determined by the cytopathogenicity of said recombinant virus to cells or by determining the replicative capacity of said recombinant virus in the presence of at least one drug.

A further embodiment of the invention is an in vitro method for determining the phenotypic susceptibility of HIV to at least one drug, comprising:

i) using at least one sample comprising HIV RNA from a patient, wherein the sample comprises the complete HIV gag-pol coding region;

ii) reverse-transcribing and amplifying said HIV RNA with primers specific for the complete HIV gag-pol coding region to obtain an amplicon comprising the complete HIV gag-pol coding region, wherein at least one primer is selected from SEQ ID NO: 1-4;

iii) determining the nucleotide sequence of the amplicon or a portion thereof as obtained in step ii), and iv) comparing the nucleotide sequence of the amplicon with the sequence of sequences whose phenotypic susceptibility is known to estimate the phenotypic susceptibility of HIV to at least one drug, wherein said susceptibility is determined by the cytopathogenicity of said recombinant virus to cells or by determining the replicative capacity of said recombinant virus in the presence of at least one drug.

Part of the invention is also wherein the embodiment is an in vitro method for determining the phenotypic susceptibility of HIV to at least one drug, comprising:

i) using at least one sample comprising HIV RNA from a patient, wherein the sample comprises the region spanning the HIV gag-protease coding sequence;

ii) reverse-transcribing and amplifying said HIV RNA with primers specific for the region spanning the HIV gag-protease coding sequence to obtain an amplicon comprising the region spanning the HIV gag-protease coding region, wherein at least one primer is selected from SEQ ID NO: 1 and SEQ ID NO: 8-10;

iii) determining the nucleotide sequence of the amplicon or a portion thereof as obtained in step ii), and iv) comparing the nucleotide sequence of the amplicon with the sequence of sequences whose phenotypic susceptibility is known to estimate the phenotypic susceptibility of HIV to at least one drug, wherein said susceptibility is determined by the cytopathogenicity of said recombinant virus to cells or by determining the replicative capacity of said recombinant virus in the presence of at least one drug.

In addition the invention relates to an in vitro method for determining the phenotypic susceptibility of HIV to at least one drug, comprising:

i) using at least one sample comprising HIV RNA from a patient, wherein the sample comprises the complete HIV reverse transcriptase-integrase coding sequence;

ii) reverse-transcribing and amplifying said HIV RNA with primers specific for the complete HIV reverse transcriptase-integrase coding sequence to obtain an amplicon comprising the complete HIV reverse transcriptase-integrase coding region, wherein at least one primer is selected from SEQ ID NO: 4-7;

iii) determining the nucleotide sequence of the amplicon or a portion thereof as obtained in step ii), and iv) comparing the nucleotide sequence of the amplicon with the sequence of sequences whose phenotypic susceptibility is known to estimate the phenotypic susceptibility of HIV to at least one drug, wherein said susceptibility is determined by the cytopathogenicity of said recombinant virus to cells or by determining the replicative capacity of said recombinant virus in the presence of at least one drug.

To the invention also belongs an in vitro method for determining the phenotypic susceptibility of HIV to at least one drug, comprising:

i) using at least one sample comprising HIV DNA wherein the sample comprises the complete HIV gag-pol coding region;

ii) amplifying said HIV DNA with primers specific for the complete HIV gag-pol coding region to obtain an amplicon comprising the complete HIV gag-pol coding region, wherein at least one primer is selected from SEQ ID NO: 1-4;

iii) determining the nucleotide sequence of the amplicon or a portion thereof as obtained in step ii), and iv) comparing the nucleotide sequence of the amplicon with the sequence of sequences whose phenotypic susceptibility is known to estimate the phenotypic susceptibility of HIV to at least one drug, wherein said susceptibility is determined by the cytopathogenicity of said recombinant virus to cells or by determining the replicative capacity of said recombinant virus in the presence of at least one drug.

The above embodiment of the invention can be extended to an in vitro method for determining the phenotypic susceptibility of HIV to at least one drug using at least one sample comprising HIV DNA wherein the sample comprises the region spanning the HIV gag-protease coding sequence using the appropriate primers SEQ ID NO: 1 and SEQ ID NO: 8-10 or wherein the sample comprises the complete HIV reverse transcriptase-integrase coding region using the appropriate primers selected from SEQ ID NO 4-7 respectively.

Part of the invention is also an in vitro method for designing a drug regimen for an HIV-infected patient by determining the phenotypic susceptibility of HIV to at least one drug, comprising:

i) using at least one sample comprising HIV RNA from a patient, wherein the sample comprises the complete HIV pol coding region;

ii) reverse-transcribing and amplifying the HIV RNA with primers specific for the complete HIV pol coding region to obtain at least one amplicon comprising the complete HIV pol coding region, wherein at least one primer is selected from SEQ ID NO's: 2, 4, 53 and 54;

iii) generating a plasmid comprising a reference HIV sequence with a deletion of the complete HIV pol coding region;

iv) preparing at least one recombinant virus by recombination or ligation between at least one amplicon obtained in step ii) and the plasmid comprising the reference HIV sequence with a deletion of the complete HIV pol coding region obtained in step iii), and v) monitoring at least one recombinant virus in the presence of at least one drug to determine the phenotypic susceptibility of HIV to at least one drug, wherein said susceptibility is determined by the cytopathogenicity of said recombinant virus to cells or by determining the replicative capacity of said recombinant virus in the presence of at least one drug.

In addition also to the invention belongs an in vitro method for designing a drug regime for an HIV-infected patient by determining the phenotypic susceptibility of HIV to at least one drug, comprising:

i) using at least one sample comprising HIV DNA, wherein the sample comprises the complete HIV pol coding region;

ii) amplifying the HIV DNA with primers specific for the complete HIV pol coding region to obtain at least one amplicon comprising the complete HIV pol coding region, wherein at least one primer is selected from SEQ ID NO: 2, 4, 53 and 54;

iii) generating a plasmid comprising a reference HIV sequence with a deletion of the complete HIV pol coding region;

iv) preparing at least one recombinant virus by recombination or ligation between at least one amplicon obtained in step ii) and the plasmid comprising the reference HIV sequence with a deletion of the complete HIV pol coding region obtained in step iii), and v) monitoring at least one recombinant virus in the presence of at least one drug to determine the phenotypic susceptibility of HIV to at least one drug, wherein said susceptibility is determined by the cytopathogenicity of said recombinant virus to cells or by determining the replicative capacity of said recombinant virus in the presence of at least one drug The disclosure further describes a method of constructing a genotypic and phenotypic database of HIV sequences, comprising:

i) using samples of HIV RNA from a patient comprising the complete HIV gag-pol coding region;

ii) reverse-transcribing and amplifying said HIV RNA with primers specific for the complete HIV gag-pol coding region to obtain an amplicon comprising the complete HIV gag-pol coding region, wherein at least one primer is selected from SEQ ID NO: 1-4;

iii) determining the nucleotide sequence of the amplicon or portions thereof as obtained in step ii);

iv) generating a plasmid comprising a reference HIV sequence with a deletion of the complete HIV gag-pol coding region;

v) preparing recombinant virus by recombination or ligation between the amplicon obtained in step ii) and the plasmid comprising the reference HIV sequence with a deletion of the complete HIV gag-pol coding region obtained in step iv);

vi) determining the relative replicative capacity of the recombinant virus in the presence of anti-HIV drugs compared to an HIV with a reference complete HIV gag-pol coding region.

The disclosure also comprises an in vitro method of constructing a genotypic and phenotypic database of HIV sequences, comprising:

i) using samples of HIV DNA comprising the complete HIV gag-pol coding region;

ii) amplifying said HIV DNA with primers specific for the complete HIV gag-pol coding region to obtain an amplicon comprising the complete HIV gag-pol coding region, wherein at least one primer is selected from SEQ ID NO: 1-4;

iii) determining the nucleotide sequence of the amplicon or portions thereof as obtained in step ii);

iv) generating a plasmid comprising a reference HIV sequence with a deletion of the complete HIV gag-pol coding region;

v) preparing recombinant virus by recombination or ligation between the amplicon obtained in step ii) and the plasmid comprising the reference HIV sequence with a deletion of the complete HIV gag-pol coding region obtained in step iv);

vi) determining the relative replicative capacity of the recombinant virus in the presence of anti-HIV drugs compared to an HIV virus with a reference complete HIV gag-pol coding region.

The above embodiments of the invention of constructing a genotypic and phenotypic database of HIV sequences can be extended to using at least one sample comprising either HIV RNA or DNA wherein the sample comprises the region spanning the HIV gag-protease coding sequence using the appropriate primers SEQ ID NO: 1 and SEQ ID NO: 8-10 or wherein the sample comprises the complete HIV reverse transcriptase-integrase coding region using the appropriate primers selected from SEQ ID NO 4-7 respectively.

Part of the invention is also a method of constructing a genotypic and phenotypic database of HIV sequences, comprising:

i) using samples of HIV RNA from a patient comprising the complete HIV pol coding region;

ii) reverse-transcribing and amplifying said HIV RNA with primers specific for the complete HIV pol coding region to obtain an amplicon comprising the complete HIV pol coding region, wherein at least one primer is selected from SEQ ID NO: 2, 4, 53 and 54;

iii) determining the nucleotide sequence of the amplicon or portions thereof as obtained in step ii);

iv) generating a plasmid comprising a reference HIV sequence with a deletion of the complete HIV pol coding region;

v) preparing recombinant virus by recombination or ligation between the amplicon obtained in step ii) and the plasmid comprising the reference HIV sequence with a deletion of the complete HIV pol coding region obtained in step iv);

vi) determining the relative replicative capacity of the recombinant virus in the presence of anti-HIV drugs compared to an HIV with a reference complete HIV pol coding region.

In addition to the invention also belongs an in vitro method of constructing a genotypic and phenotypic database of HIV sequences, comprising:

i) using samples of HIV DNA comprising the complete HIV pol coding region;

ii) amplifying said HIV DNA with primers specific for the complete HIV pol coding region to obtain an amplicon comprising the complete HIV pol coding region, wherein at least one primer is selected from SEQ ID NO: 2, 4, 53 and 54;

iii) determining the nucleotide sequence of the amplicon or portions thereof as obtained in step ii);

iv) generating a plasmid comprising a reference HIV sequence with a deletion of the complete HIV pol coding region;

v) preparing recombinant virus by recombination or ligation between the amplicon obtained in step ii) and the plasmid comprising the reference HIV sequence with a deletion of the complete HIV pol coding region obtained in step iv);

vi) determining the relative replicative capacity of the recombinant virus in the presence of anti-HIV drugs compared to an HIV virus with a reference complete HIV pol coding region.

The present invention also comprises the plasmids or sometimes called vectors described in the experimental part and the use of these plasmids or vectors in the methods described herein. The HIV sequence incorporated in the plasmid or vector may be based on the K03455 sequence. The complete HIV sequence may be incorporated or only part thereof. A suitable plasmid backbone may be selected from the group including pUC, pSV or pGEM.

To prepare vectors containing recombinant HIV gag-pol coding sequences, the patient derived gag-pol RNA was reverse transcribed and amplified by the polymerase chain reaction (PCR), then inserted into a vector containing the wild type HIV genome sequence but lacking a complete gag-pol coding region. Different primer combinations were initially used to obtain the amplified DNA sequences from patient samples. The 5' to 3' sequences and the primers identified as SEQ ID's NO: 1-10, more specifically SEQ ID NO's: 1-4 were successfully used to reverse transcribe and PCR amplify gag-pol coding region are listed below in Table 7.

To prepare a vector containing recombinant HIV gag-protease coding sequence, the patient derived gag-protease RNA was reverse transcribed and amplified by the polymerase chain reaction (PCR), then inserted into a vector containing the wild type HIV genome sequence but lacking gag-protease coding region. Different primer combinations were initially used to obtain the amplified DNA sequences from patient samples. The 5' to 3' sequences and the primers identified as SEQ ID's NO: 1-10, more specifically SEQ ID NO: 1 and SEQ ID NO's 8-10 were successfully used to reverse transcribe and PCR amplify gag-protease coding region are listed below in Table 7.

To prepare a vector containing recombinant HIV reverse transcriptase-integrase coding sequence, the patient derived reverse transcriptase-integrase RNA was reverse transcribed and amplified by the polymerase chain reaction (PCR), then inserted into a vector containing the wild type HIV genome sequence but lacking reverse transcriptase-integrase coding region. Different primer combinations were initially used to obtain the amplified DNA sequences from patient samples. The 5' to 3' sequences and the primers identified as SEQ ID's NO: 1-10, more specifically SEQ ID NO: 4-7 were successfully used to reverse transcribe and PCR amplify reverse transcriptase-integrase coding region are listed below in Table 7.

To prepare a vector containing recombinant HIV pol coding sequences, the patient derived pol RNA was reverse transcribed and amplified by the polymerase chain reaction (PCR), then inserted into a vector containing the wild type HIV genome sequence but lacking a complete pol coding region. Different primer combinations were initially used to obtain the amplified DNA sequences from patient samples. The 5' to 3' sequences and the primers identified as SEQ ID's NO: 2, 4, 53 and 54 were successfully used to reverse transcribe and PCR amplify pol coding region and are listed below in Table 7.

Reverse transcription and amplification may be performed with a single set of primers. Alternatively, more than one set of primers may be used in a hemi-nested approach to reverse transcribe and amplify the genetic material. Particularly, more than one set of primer is used in a nested approach. Following the generation of the recombinant construct, the chimeric virus may be grown and the viral titer determined (expressed as 50% cell culture infectious dose, CCID50) before proceeding to the determination of the phenotypic susceptibility.

"Chimeric" means a construct comprising nucleic acid material from different origin such as for example a combination of wild type HIV with a laboratory HIV virus, a combination of wild type HIV sequence and patient derived HIV sequence.

The indicator gene, encoding a signal indicative of replication of the virus in the presence of a drug or indicative of the susceptibility of the virus in the presence of a drug may be present in the culturing cells such as MT-4 cells. In addition, said indicator gene may be incorporated in the chimeric construct introduced into the culturing cells or may be introduced separately. Suitable indicator genes encode fluorescent proteins, particularly green fluorescent protein (GFP) or mutants thereof such as eGFP (enhanced GFP).

Genetic material may be introduced into the cells using a variety of techniques known in the art including, calcium phosphate precipitation, liposomes, viral infection, and electroporation. The monitoring may be performed in high throughput.

A human immunodeficiency virus (HIV), as used herein refers to any HIV including laboratory HIV strains, wild type HIV strains, mutant HIV strains and any biological sample comprising HIV such as a HIV clinical isolate. HIV strains compatible with the present invention are those strains capable of infecting mammals, particularly humans such as HIV-1 and HIV-2. A patient may have HIV in his body with different mutations in the integrase (IN) gene. It is to be understood that a sample may contain a variety of different HIV containing different mutational profiles in the IN gene. A sample may be obtained for example from an individual, from cell cultures, or generated using recombinant technology, or cloning. Viral strains used for obtaining a plasmid are preferably HIV wild-type sequences, such as LAI or HXB2D. LAI, also known as IIIB, is a wild type HIV strain. One particular clone thereof, this means one sequence, is HXB2D. This sequence may be incorporated into a plasmid.

Instead of viral RNA, HIV DNA, e.g. proviral DNA, may be used for the methods described herein. In case RNA is used, reverse transcription into DNA by a suitable reverse transcriptase is needed. The protocols describing the analysis of RNA are also amenable for DNA analysis. However, if a protocol starts from DNA, the person skilled in the art will know that no reverse transcription is needed. The primers designed to amplify the RNA strand, also anneal to, and amplify DNA. Reverse transcription and amplification may be performed with a single set of primers. Suitably a hemi-nested and more suitably a nested approach may be used to reverse transcribe and amplify the genetic material.

Nucleic acid may be amplified by techniques such as polymerase chain reaction (PCR), nucleic acid sequence based amplification (NASBA), self-sustained sequence replication (3SR), transcription-based amplification (TAS), ligation chain reaction (LCR). Preferably the polymerase chain reaction is used.

Any type of patient sample may be used to obtain the integrase gene, such as serum or tissue. Viral RNA may be isolated using known methods such as described in Boom, R. et al. (J. Clin. Microbiol. 28(3): 495-503 (1990)). Alternatively, a number of commercial methods such as the QIAAMP® viral RNA kit (Qiagen, Inc.) or EasyMag RNA extraction platform (Biomérieux, Boxtel, the Netherlands) may be used to obtain viral RNA from bodily fluids such as plasma, serum, or cell-free fluids. DNA may be obtained by procedures known in the art (e.g. Maniatis, 1989) and commercial procedures (e.g. Qiagen).

According to the instant invention, for instance, the complete HIV gag and complete pol (Protease-reverse transcriptase-integrase) coding region (4588 bp) is used to prepare an amplicon.

"Amplicon" refers to the amplified, and where necessary, reverse transcribed complete gag-protease-reverse transcriptase-integrase sequence.

It should be understood that this complete gag-protease-reverse transcriptase-integrase sequence may be of diverse origin including plasmids and patient material. Suitably, the amplicon is obtained from patient material.

For the purpose of the present invention the amplicon is sometimes referred to as "DNA construct". A viral sequence may contain one or multiple mutations versus the consensus reference sequence given by HXB2D, GenBank accession number K03455. Said sequence, K03455, is present in Genbank and available through the Internet. A single mutation or a combination of mutations may correlate to a change in drug efficacy. This correlation may be indicative of an altered i.e. decreased or increased susceptibility of the virus for a drug. Said mutations may also influence the viral fitness.

A "drug" means any agent such as a chemotherapeutic, peptide, antibody, antisense, ribozyme and any combination thereof. Examples of drugs include protease inhibitors including darunavir, ritonavir, amprenavir, nelfinavir; reverse transcriptase inhibitors such as nevirapine, delavirdine, AZT, zidovudine, didanosine; integrase inhibitors; agents interfering with envelope (such as T-20).

Treatment or treatment regimen refers to the therapeutic management of an individual by the administration of drugs. Different drug dosages, administration schemes, administration routes and combinations may be used to treat an individual.

An alteration in viral drug sensitivity is defined as a change in susceptibility of a viral strain to said drug. Susceptibilities are generally expressed as ratios of $EC_{50}$ or $EC_{90}$ values (the $EC_{50}$ or $EC_{90}$ value being the drug concentration at which 50% or 90% respectively of the viral population is inhibited from replicating) of a viral strain under investigation compared to the wild type strain. Hence, the susceptibility of a viral strain towards a certain drug can be expressed as a fold change in susceptibility, wherein the fold change is derived from the ratio of for instance the $EC_{50}$ values of a mutant viral strain compared to the wild type $EC_{50}$ values. In particular, the susceptibility of a viral strain or population may also be expressed as resistance of a viral strain, wherein the result is indicated as a fold increase in $EC_{50}$ as compared to wild type $IC_{50}$.

The $IC_{50}$ is the drug concentration at which 50% of the enzyme activity is inhibited.

The susceptibility of HIV to a drug is tested by either determining the cytopathogenicity of the recombinant virus to cells or by determining the replicative capacity of the recombinant virus in the presence of at least one drug, relative to the replicative capacity of a wild type or reference HIV.

In the context of this invention, the cytopathogenic effect means the viability of the cells in culture in the presence of chimeric viruses. The cells may be chosen from T cells, monocytes, macrophages, dendritic cells, Langerhans cells, hematopoetic stem cells or precursor cells, MT4 cells and PM-1 cells. The cytopathogenicity may, for example, be followed microscopically, or replication might be monitored by the presence of any reporter molecule including reporter genes. A reporter gene is defined as a gene whose product has reporting capabilities. Suitable reporter molecules include tetrazolium salts, green fluorescent proteins, beta-galactosidase, chloramfenicol transferase, alkaline phophatase, and luciferase. Several methods of cytopathogenic testing including phenotypic testing are described in the literature comprising the recombinant virus assay (Kellam and Larder, Antimicrob. Agents Chemotherap. 1994, 38, 23-30, Hertogs et al. Antimicrob. Agents Chemotherap. 1998, 42, 269-276; Pauwels et al. J. Virol Methods 1988, 20, 309-321)

The susceptibility of HIV to a drug may also be determined by the replicative capacity of the recombinant virus in the presence of at least one drug, relative to the replicative capacity of a reference or wild type HIV. Replicative capacity means the ability of the virus or chimeric construct to grow under culturing conditions. This is sometimes referred to as viral fitness. The culturing conditions may contain triggers that influence the growth of the virus, examples of which are drugs. The methods for determining the susceptibility may be useful for designing a treatment regimen for an HIV-infected patient. For example, a method may comprise determining the replicative capacity of a clinical isolate of a patient and using said replicative capacity to determine an appropriate drug regime for the patient.

The phenotyping assays of the present invention can be performed at high throughput using, for example, a microtiter plate containing a variety of anti-HIV drugs. The present assays may be used to analyze the influence of changes at the HIV gag-pol gene to any type of drug useful to treat HIV. Examples of anti-HIV drugs that can be tested in this assay include, nucleoside and non-nucleoside reverse transcriptase inhibitors, nucleotide reverse transcriptase inhibitors, protease inhibitors, maturation inhibitors, RNaseH inhibitors and integrase inhibitors, but those of skill in the art will appreciate that other types of antiviral compounds may also be tested. The results may be monitored by several approaches including but not limited to morphology screening, microscopy, and optical methods, such as, for example, absorbance and fluorescence. An $IC_{50}$ value for each drug may be obtained in these assays and used to determine viral replicative capacity in the presence of the drug. Apart from $IC_{50}$ also e.g. $IC_{90}$ can be used. The replicative capacity of the viruses may be compared to that of a wild-type HIV virus to determine a relative replicative capacity value. Data from phenotypic assays may further be used to predict the behaviour of a particular HIV isolate to a given drug based on its genotype.

The assays of the present invention may be used for therapeutic drug monitoring. Said approach includes a combination of susceptibility testing, determination of drug level and assessment of a threshold. Said threshold may be derived from population based pharmacokinetic modelling (WO 02/23186). The threshold is a drug concentration needed to obtain a beneficial therapeutic effect in vivo. The in vivo drug level may be determined using techniques such as high performance liquid chromatography, liquid chromatography, mass spectroscopy or combinations thereof. The susceptibility of the virus may be derived from phenotyping or interpretation of genotyping results i.e. virtual phenotyping (WO 01/79540).

The assays of the present invention may be useful to discriminate an effective drug from an ineffective drug by establishing cut-offs i.e. biological cut-offs (see e.g. WO 02/33402). A biological cut-off is drug specific. These cut-offs are determined following phenotyping a large population of individuals containing wild type viruses. The cut-off is derived from the distribution of the fold increase in resistance of the virus for a particular drug.

The genotype of the patient-derived gag-pol coding region may be determined directly from the amplified DNA, i.e. the DNA construct by performing DNA sequencing. Alternatively, the sequence may be obtained after sub-cloning into a suitable vector. A variety of commercial sequencing enzymes and equipment may be used in this process. The efficiency may be increased by determining the sequence of the gag-pol coding region in several parallel reactions, each with a different set of primers. Such a process could be performed at high throughput on a multiple-well plate, for example. Commercially available detection and analysis systems may be used to determine and store the sequence information for later analysis.

The nucleotide sequence may be obtained using several approaches including sequencing nucleic acids. This sequencing may be performed using techniques including gel based approaches, mass spectroscopy and hybridisation. However, as more resistance related mutations are identified, the sequence at particular nucleic acids, codons or short sequences may be obtained. If a particular resistance associated mutation is known, the nucleotide sequence may be determined using hybridisation assays (including Biochips, LipA-assay), mass spectroscopy, allele specific PCR, or using probes or primers discriminating between mutant and wild-type sequence. A selected set of sequencing primers includes SEQ ID No's: 11-44 and 55-58 respectively (Table 10). This particular selection has the advantage that it enables the sequencing of the complete HIV gag-pol coding sequence. Consequently, using this set of primers all possible mutations that may occur in the HIV gag or pol gene may be detected.

The patient gag-pol genotype provides an additional means to determine drug susceptibility of a virus strain. Phenotyping is a lengthy process often requiring 2 or more weeks to accomplish. Therefore, systems have been developed which enable the prediction of the phenotype based on the genotypic results. The results of genotyping may be interpreted in conjunction with phenotyping and eventually be subjected to database interrogation. A suitable system is virtual phenotyping (WO 01/79540). In the virtual phenotyping process the complete gag-pol genes may be used. Alternatively, portions of the genes may be used. Also combinations of mutations, preferentially mutations indicative of a change in drug susceptibility, may be used. A combination of mutations is sometimes referred to as a hot-spot (see e.g. WO 01/79540). Briefly, in the process of virtual phenotyping, the genotype of a patient derived gag-pol sequence may be correlated to the phenotypic response of said patient derived gag-pol sequence. If no phenotyping is performed, the sequence may be screened towards a collection of sequences present in a database. Identical sequences are retrieved and the database is further interrogated to identify if a corresponding phenotype is known for any of the retrieved sequences. In this latter case a virtual phenotype may be determined. A report may be prepared including the $IC_{50}$ of the viral strain for one or more therapies, the sequence of the strain under investigation, and the biological cut-offs.

According to the methods described herein a database may be constructed comprising genotypic and phenotypic data of the HIV gag-pol sequences, wherein the database further provides a correlation between genotypes and phenotypes, wherein the correlation is indicative of efficacy of a given drug regimen. A database of gag-pol sequences may be created and used as described in WO 01/79540. For example, such a database may be analyzed in combination with gag, pol, protease, reverse transcriptase or integrase sequence information and the results used in the determination of appropriate treatment strategies. Said database containing a collection of genotypes, phenotypes and samples for which the combined genotype/phenotype are available, may be used to determine the virtual phenotype (see supra). In addition, instead of interrogating the complete gag-pol sequences, particular codons correlating to a change in drug susceptibility of the virus may be interrogated in such database.

A primer may be chosen from SEQ ID N° 1-10, 53 and 54. A particular set of primers is SEQ ID 1-4 and 53 and 54. Primers specific for the gag-pol region of the HIV genome such as the primers described herein and their homologs are disclosed to perform the assay according to the invention. The primer sequences listed herein may be labelled. Suitably, this label may be detected using fluorescence, luminescence or absorbance. The primer for creating a deletion construct may contain a portion that does not anneal to the HIV sequence. That portion may be used to introduce a unique restriction site. Interestingly, primers may be designed in which the unique restriction site is partially present in the HIV sequence. The primers are chosen from those listed herein or have at least 80% homology as determined by methods known by the person skilled in the art such BLAST or FASTA. Specifically, the homology is at least 90%, more specifically, at least 95%. In addition, primers located in a region of 50 nucleotides (nt) upstream or downstream from the sequences given herein constitute part of the invention. Especially, said region is 20 nucleotides up or downstream from the position in the HIV genome of the primer sequences given herein. Alternatively, primers comprising at least 8 consecutive bases present in either of the primers described here constitute one embodiment of the invention. Interestingly, the primers comprise at least 12 consecutive bases present in either of the primers described herein.

EXAMPLES

General Outline

An amplicon was generated from patient-derived plasma viral RNA by RT-PCR and nested PCR. This amplicon, further referred to as 5'LTR-Vif fragment, contains the complete Gag and complete Pol (PR-RT-INT) coding region (4588 bp). Sequence primers across the 5' end of HIV-1 allow for nucleotide sequence determination and genotypic drug resistance analysis.

A delta[Gag-Pol] backbone (SEQ ID NO: 49) was made starting from an HIV-1 vector that contains eGFP in the Nef coding region. In vitro cloning (using BD In-Fusion™, Clontech Laboratories Inc.) between the PCR-generated amplicon and the delta[Gag-Pol] backbone resulted in a fully replication-competent HIV-1 that was used in experiments to evaluate phenotypic drug resistance.

Further, an amplicon spanning the Gag cleavage sites p1/p7 and p1/p6, PR, RT, RNaseH and INT (3202 bp), referred to as Pol fragment, was evaluated together with an amplicon containing the Gag and PR coding sequence (1980 bp), referred to as Gag-PR fragment, and an amplicon containing the complete RT, RNaseH and INT coding sequence (2898 bp), named RT-INT fragment.

For phenotypic evaluation delta[Pol] (SEQ ID NO: 52) delta[Gag-PR] (SEQ ID NO: 50) and delta[RT-INT] HIV-1 (SEQ ID NO: 51) backbones, also containing eGFP (enhanced Green Fluorescent protein) in Nef, were designed respectively.

Protocol for Amplification of 5'LTR-VIF Fragment

Starting from freshly prepared patient-derived RNA, 5 µl was mixed with 0.2 µM forward outer primer (5LTR_IF1=SEQ ID NO: 1) and 0.2 µM reverse outer primer (VIF_R2=SEQ ID NO: 2), 1× Superscript™ reaction buffer (containing 0.4 mM of each dNTP and 2.5 mM MgSO$_4$) and 0.5 µl Superscript™ III HIFI enzyme mix in a total volume of 25 µl (Table 1). The reverse transcription reaction was performed @ 53° C. for 30 mM, followed by an initial denaturation @ 94° C. for 2 min. This was followed by 30 cycles of [denaturation @ 92° C. for 15 sec, annealing @ 55° C. for 30 sec and elongation @ 68° C. for 5 min]. The final elongation step was 10 min @ 68° C. (Table 2).

Subsequently, 1 µl of outer PCR product was mixed with 0.304 µM forward inner primer (5LTR_F2=SEQ ID NO: 3) and 0.304 µM reverse inner primer (VIF_R5=SEQ ID NO: 4), 1× Expand™ HIFI reaction buffer, 0.2 µl dNTP's (0.2 mM) and 0.3 µl Expand™ HIFI enzyme mix (=1.05 U) in a total volume of 25 µl (Table 1).

The inner PCR reaction consists of an initial denaturation @ 94° C. for 2 min, followed by 35 cycles of [denaturation @ 94° C. for 15 sec, annealing @ 61° C. for 30 sec and elongation @ 68° C. for 5 min] The final elongation step was 10 min @ 68° C. (Table 2).

All reaction mixtures and samples were kept on ice during preparation. The outer and inner primers used to generate this amplicon can be found in Table 7.

Finally, 4 µl PCR product was mixed with 2 µl loading dye, loaded on a 1% agarose gel and stained with ethidium bromide for visualization.

TABLE 1

Composition of the RT-outer PCR mix and inner PCR mix for amplification of the 5'LTR-VIF fragment.

| RT-outer PCR mix | | inner PCR mix | |
|---|---|---|---|
| component | volume/sample (µl) | component | volume/sample (µl) |
| DEPC.water | 6.5 | DEPC. water | 20.24 |
| 2 × reaction buffer | 12.5 | 10 × reaction buffer | 2.5 |
| 5LTR_IF1 primer (20 µM) | 0.25 | 5LTR_F2 primer (20 µM) | 0.38 |
| VIF_R2 primer (20 µM) | 0.25 | VIF_R5 primer (20 µM) | 0.38 |
| Superscript III HiFi | 0.5 | dNTP's (25 mM) | 0.2 |
| RNA | 5 | Expand HiFi (3.5 U/µl) | 0.3 |
| total volume (µl) | 25 | OUT_sample | 1 |
| | | total volume (µl) | 25 |

TABLE 2

Thermal cycling conditions for the outer and inner PCR for amplification of the 5'LTR-VIF fragment.

| outer PCR 5'LTR-VIF fragment | | | | inner PCR 5'LTR-VIF fragment | | | |
|---|---|---|---|---|---|---|---|
| step | temperature (° C.) | time | cycles | step | temperature (° C.) | time | cycles |
| 1 | 53 | 30 min | | 1 | 94 | 2 min | |
| 2 | 94 | 2 min | | 2 | 94 | 15 s | 35 |
| 3 | 92 | 15 s | 30 | 3 | 61 | 30 s | |
| 4 | 55 | 30 s | | 4 | 68 | 5 min | |
| 5 | 68 | 5 min | | 5 | 68 | 10 min | |
| 6 | 68 | 10 min | | 6 | 4 | hold | |
| 7 | 4 | hold | | | | | |

Protocol for Amplification of Pol Fragment

Starting from freshly prepared patient-derived RNA, 5 µl was mixed with 0.2 µM forward outer primer (5'OUT=SEQ ID NO: 53) and 0.2 µM reverse outer primer (VIF_R2=SEQ ID NO: 2), 1× Superscript™ reaction buffer (containing 0.4 mM of each dNTP and 2.5 mM MgSO$_4$) and 0.5 µl Superscript™ III HIFI enzyme mix in a total volume of 25 µl (Table 12). The reverse transcription reaction was performed @ 53° C. for 30 min, followed by an initial denaturation @ 94° C. for 2 min. This was followed by 30 cycles of [denaturation @ 92° C. for 15 sec, annealing @ 55° C. for 30 sec and elongation @ 68° C. for 3 min 30 sec]. The final elongation step was 10 min @ 68° C. (Table 13).

Subsequently, 1 µl of outer PCR product was mixed with 0.304 µM forward inner primer (5'IN=SEQ ID NO: 54) and 0.304 µM reverse inner primer (VIF_R5=SEQ ID NO: 4), 1× Expand™ HIFI reaction buffer, 0.2 µl dNTP's (0.2 mM) and 0.3 µl Expand™ HIFI enzyme mix (=1.05 U) in a total volume of 25 µl (Table 12).

The inner PCR reaction consists of an initial denaturation @ 94° C. for 2 min, followed by 35 cycles of [denaturation @ 94° C. for 15 sec, annealing @ 58° C. for 30 sec and elongation @ 68° C. for 3 min 30 sec]. The final elongation step was 10 min @ 68° C. (Table 13).

All reaction mixtures and samples were kept on ice during preparation. The outer and inner primers used to generate this amplicon can be found in Table 7.

Finally, 4 µl PCR product was mixed with 2 µl loading dye, loaded on a 1% agarose gel and stained with ethidium bromide for visualization.

TABLE 12

Composition of the RT-outer PCR mix and inner PCR mix for amplification of the Pol fragment.

| RT-outer PCR mix | | inner PCR mix | |
|---|---|---|---|
| component | volume/sample (µl) | component | volume/sample (µl) |
| DEPC.water | 6.5 | DEPC. water | 20.24 |
| 2 × reaction buffer | 12.5 | 10 × reaction buffer | 2.5 |
| 5LTR_IF1 primer (20 µM) | 0.25 | 5LTR_F2 primer (20 µM) | 0.38 |
| VIF_R2 primer (20 µM) | 0.25 | VIF_R5 primer (20 µM) | 0.38 |
| Superscript III HiFi | 0.5 | dNTP's (25 mM) | 0.2 |
| RNA | 5 | Expand HiFi (3.5 U/µl) | 0.3 |
| total volume (µl) | 25 | OUT_sample | 1 |
| | | total volume (µl) | 25 |

TABLE 13

Thermal cycling conditions for the outer and inner PCR for amplification of the Pol fragment.

| | outer PCR Pol fragment | | | | inner PCR Pol fragment | | |
|---|---|---|---|---|---|---|---|
| step | temperature (° C.) | time | cycles | step | temperature (° C.) | time | cycles |
| 1 | 53 | 30 min | | 1 | 94 | 2 min | |
| 2 | 94 | 2 min | | 2 | 94 | 15 s | 35 |
| 3 | 92 | 15 s | 30 | 3 | 58 | 30 s | |
| 4 | 55 | 30 s | | 4 | 68 | 3 min 30 sec | |
| 5 | 68 | min 30 sec | | 5 | 68 | 10 min | |
| 6 | 68 | 10 min | | 6 | 4 | hold | |
| 7 | 4 | hold | | | | | |

Protocol for Amplification of RT-INT Fragment

Starting from freshly prepared patient-derived RNA, 5 μl was mixed with 0.2 μM forward outer primer (PR_F1=SEQ ID NO: 5) and 0.2 μM reverse outer primer (VIF_R3=SEQ ID NO: 6), 1× Superscript™ reaction buffer (containing 0.4 mM of each dNTP and 2.5 mM MgSO$_4$) and 0.5 μl Superscript™ III HIFI enzyme mix in a total volume of 25 μl (Table 3). The reverse transcription reaction was performed @ 56° C. for 30 min, followed by an initial denaturation @ 94° C. for 2 min. This was followed by 30 cycles of [denaturation @ 92° C. for 15 sec, annealing @ 62° C. for 30 sec and elongation @ 68° C. for 3 min 30 sec]. The final elongation step was 10 min @ 68° C. (Table 4).

Subsequently, 1 μl of outer PCR product was mixed with 0.304 μM forward inner primer (PR_F3=SEQ ID NO: 7) and 0.304 μM reverse inner primer (VIF_R5=SEQ ID NO: 4), 1× Expand™ HIFI reaction buffer, 0.2 μl dNTP's (0.2 mM) and 0.3 μl Expand™ HIFI enzyme mix (=1.05 U) in a total volume of 25 μl (Table 3)

The inner PCR reaction consists of an initial denaturation @ 94° C. for 2 min, followed by 35 cycles of [denaturation @ 94° C. for 15 sec, annealing @ 60° C. for 30 sec and elongation @ 68° C. for 3 min] The final elongation step was 10 min @ 68° C. (Table 4).

All reaction mixtures and samples were kept on ice during preparation. The outer and inner primers used to generate this amplicon can be found in Table 7.

Finally, 4 μl PCR product was mixed with 2 μl loading dye, loaded on a 1% agarose gel and stained with ethidium bromide for visualization.

TABLE 3

Composition of the RT-outer PCR mix and inner PCR mix for amplification of the RT-INT fragment.

| RT-outer PCR mix | | inner PCR mix | |
|---|---|---|---|
| component | volume/sample (μl) | component | volume/sample (μl) |
| DEPC.water | 6.5 | DEPC.water | 20.24 |
| 2 × reaction buffer | 12.5 | 10 × reaction buffer | 2.5 |
| PR_F1 (20 μM) | 0.25 | PR_F3 (20 μM) | 0.38 |
| VIF_R3 (20 μM) | 0.25 | VIF_R5 (20 μM) | 0.38 |
| Superscript III HiFi | 0.5 | dNTP's (25 mM) | 0.2 |
| RNA | 5 | Expand HiFi (3.5 U/μl) | 0.3 |
| total volume (μl) | 25 | OUT_sample | 1 |
| | | total volume (μl) | 25 |

TABLE 4

Thermal cycling conditions for the outer and inner PCR for amplification of the RT-INT fragment.

| | outer PCR RT-INT fragment | | | | inner PCR RT-INT fragment | | |
|---|---|---|---|---|---|---|---|
| step | temperature (° C.) | time | cycles | step | temperature (° C.) | time | cycles |
| 1 | 53 | 30 min | | 1 | 94 | 2 min | |
| 2 | 94 | 2 min | | 2 | 94 | 15 s | 35 |
| 3 | 92 | 15 s | 30 | 3 | 60 | 30 s | |
| 4 | 55 | 30 s | | 4 | 68 | 3 min | |
| 5 | 68 | 3 min 30 s | | 5 | 68 | 10 min | |
| 6 | 68 | 10 min | | 6 | 4 | hold | |
| 7 | 4 | hold | | | | | |

Protocol for Amplification of GAG-PR Fragment

Starting from freshly prepared patient-derived RNA, 5 μl was mixed with 0.2 μM forward outer primer (EF1=SEQ ID NO: 8) and 0.2 μM reverse outer primer (Gaprout-R3=SEQ ID NO: 9), 1× Superscript™ reaction buffer (containing 0.4 mM of each dNTP and 2.5 mM $MgSO_4$) and 0.5 μl Superscript™ III HIFI enzyme mix in a total volume of 25 μl (Table 5). The reverse transcription reaction was performed @ 53° C. for 30 min, followed by an initial denaturation @ 94° C. for 2 min. This was followed by 30 cycles of [denaturation @ 92° C. for 15 sec, annealing @ 55° C. for 30 sec and elongation @ 68° C. for 2 min 30 sec]. The final elongation step was 10 min @ 68° C. (Table 6).

Subsequently, 1 μl of outer PCR product was mixed with 0.304 μM forward inner primer (5LTR_IF1=SEQ ID NO:1) and 0.304 μM reverse inner primer (Gaprout-R1=SEQ ID NO: 10), 1× Expand™ HIFI reaction buffer, 0.2 μl dNTP's (0.2 mM) and 0.3 μl Expand™ HIFI enzyme mix (=1.05 U) in a total volume of 25 μl (Table 5).

The inner PCR reaction consists of an initial denaturation @ 94° C. for 2 min, followed by 35 cycles of [denaturation @ 94° C. for 15 sec, annealing @ 60° C. for 30 sec and elongation @ 72° C. for 2 min] The final elongation step was 10 min @ 72° C. (Table 6).

All reaction mixtures and samples were kept on ice during preparation. The outer and inner primers used to generate this amplicon can be found in Table 7.

Finally, 4 μl PCR product was mixed with 2 μl loading dye, loaded on a 1% agarose gel and stained with ethidium bromide for visualization.

TABLE 5

Composition of the RT-outer PCR mix and inner PCR mix for amplification of the GAG-PR fragment.

| RT-outer PCR mix | | inner PCR mix | |
| --- | --- | --- | --- |
| component | volume/sample (μl) | component | volume/sample (μl) |
| DEPC.water | 6.5 | DEPC.water | 20.24 |
| 2 × reaction buffer | 12.5 | 10 × reaction buffer | 2.5 |
| EF1 (20 μM) | 0.25 | 5LTR_IF1 (20 μM) | 0.38 |
| Gaprout-R3 (20 μM) | 0.25 | Gaprout-R1 (20 μM) | 0.38 |
| Superscript III HiFi | 0.5 | dNTP's (25 mM) | 0.2 |
| RNA | 5 | Expand HiFi (3.5 U/μl) | 0.3 |
| total volume (μl) | 25 | OUT_sample | 1 |
| | | total volume (μl) | 25 |

TABLE 6

Thermal cycling conditions for the outer and inner PCR for amplification of the GAG-PR fragment.

| outer PCR Gag-PR fragmmt | | | | inner PCR Gag-PR fragmmt | | | |
| --- | --- | --- | --- | --- | --- | --- | --- |
| step | temperature (° C.) | time | cycles | step | temperature (° C. | time | cycles |
| 1 | 53 | 30 min | | 1 | 94 | 2 min | |
| 2 | 94 | 2 min | | 2 | 94 | 15 s | 35 |
| 3 | 92 | 15 s | 30 | 3 | 60 | 30 s | |
| 4 | 55 | 30 s | | 4 | 72 | 2 min | |
| 5 | 68 | 2 min 30 s | | 5 | 72 | 10 min | |
| 6 | 68 | 10 min | | 6 | 4 | hold | |
| 7 | 4 | hold | | | | | |

TABLE 7

Primer sequences of all amplification primers and their position on the HXB2 reference.

| primer name | primer sequence from 5' to 3' | position on HXB2 |
| --- | --- | --- |
| EF1 | CAA GTA GTG TGT GCC CGT CTG T | 550-571 |
| 5LTR_IF1 | TGG AAA ATC TCT AGC AGT GGC G | 619-640 |
| 5LTR_F2 | TCT CTA GCA GTG GCG CCC GAA CA | 626-648 |
| PR_F1 | CCC TCA AAT CAC TCT TTG GCA ACG AC | 2252-2277 |
| PR_F3 | GCT CTA TTA GAT ACA GGA GCA GAT G | 2316-2340 |

TABLE 7-continued

Primer sequences of all amplification primers and their position on the HXB2 reference.

| primer name | primer sequence from 5' to 3' | position on HXB2 |
|---|---|---|
| VIF_R2 | AGT GGG ATG TGT ACT TCT GAA C | 5195-5216 |
| VIF_R3 | CTC CTG TAT GCA GAC CCC AAT ATG | 5243-5266 |
| VIF_R5 | GGG ATG TGT ACT TCT GAA CTT | 5193-5213 |
| Gaprout-R3 | CCA TTG TTT AAC TTT TGG GCC ATC C | 2597-2621 |
| Gaprout-R1 | CCA TTC CTG GCT TTA ATT TTA CTG G | 2574-2598 |
| 5' OUT | GCC CCT AGG AAA AAG GGC TGT TGG | 2008-2031 |
| 5' IN | CTA GGA AAA AGG GCT GTT GGA AAT G | 2012-2036 |

| | | |
|---|---|---|
| SEQ ID NO 1: | (5LTR_IF1) | TGG AAA ATC TCT AGC AGT GGC G |
| SEQ ID NO 2: | (VIF_R2) | AGT GGG ATG TGT ACT TCT GAA C |
| SEQ ID NO 3: | (5LTR_F2) | TCT CTA GCA GTG GCG CCC GAA CA |
| SEQ ID NO 4: | (VIF_R5) | GGG ATG TGT ACT TCT GAA CTT |
| SEQ ID NO 5: | (PR_F1) | CCC TCA AAT CAC TCT TTG GCA ACG AC |
| SEQ ID NO 6: | (VIF_R3) | CTC CTG TAT GCA GAC CCC AAT ATG |
| SEQ ID NO 7: | (PR_F3) | GCT CTA TTA GAT ACA GGA GCA GAT G |
| SEQ ID NO 8: | (EF1) | CAA GTA GTG TGT GCC CGT CTG T |
| SEQ ID NO 9: | (Gaprout-R3) | CCA TTG TTT AAC TTT TGG GCC ATC C |
| SEQ ID NO 10: | (Gaprout-R1) | CCA TTC CTG GCT TTA ATT TTA CTG G |
| SEQ ID NO 53 | (5'OUT) | GCC CCT AGG AAA AAG GGC TGT TGG |
| SEQ ID NO 54 | (5'IN) | CTA GGA AAA AGG GCT GTT GGA AAT G |

Sequencing Protocol for all Fragments Mentioned Before

Sequencing reactions were performed with the Big Dye Terminator Cycle Sequencing Kit v3.1 (Applied Biosystems). Each reaction mixture (11.5 µl) contained: the amplicon (1 µl), DNase RNase free water (3 µl), Big Dye terminator mix (1 µl), primer (4 µl, 4 µM) and 1× dilution buffer (1.0 M Tris HCL, 1.0 M MgCl$_2$ and H$_2$O) (Table 8). All primers used for nucleotide sequencing of the different fragments are listed in Table 10.

The PCR conditions were 25 cycles of [10 seconds at 96° C., 5 seconds at 50° C. and 4 minutes at 60° C.], followed by a final hold at 4° C. and using an ABI 9800 Fast Thermal Cycler (Applied Biosystems) (Table 9).

The purification of the sequencing reaction mixtures was performed using the DyeEX (Qiagen) purification kit according to the manufacturers protocol. The sequencing was performed using an ABI3730 XL (Applied Biosystems) and the generated sequences were aligned and analyzed using SeqScape v2.5 software (Applied Biosystems).

TABLE 8

Composition of the sequencing reaction mixture. mix composition for sequencing

| component | vol/sample (µl) |
|---|---|
| DEPC.water | 3 |
| 2.5 × dilution buffer | 2.5 |
| Big Dye terminator mix | 1 |
| primer (4 µM) | 4 |
| template | 1 |
| total volume (µl) | 11.5 |

Thermal Cycling Program

TABLE 9

Thermal cycling conditions for the sequencing reaction.

| step | temp. | time | # cycles |
|---|---|---|---|
| 1 | 96° C. | 10 s | 25 |
| 2 | 50° C. | 5 s | |
| 3 | 60° C. | 4 min | |
| 4 | 4° C. | hold | |

TABLE 10

Primer sequences of all sequencing primers and their position on the HXB2 reference.

| | Primer name | Nucleotide sequence (5' → 3') | Position on HXB2 |
|---|---|---|---|
| Forward Primers | | | |
| SEQ ID NO 11 | 5'LTR_F_631 | AGCAGTGGCGCCCGAACAG | 631-649 |
| SEQ ID NO 12 | F0 gag | TTTGACTAGCGGGAGGCTAGAAG | 761-782 |
| SEQ ID NO 13 | GAG_F_1070 | TAAAAGACACCAAGGAAGC | 1070-1088 |
| SEQ ID NO 14 | F10 gag | AAGCACCAAGGAAGC | 1073-1088 |
| SEQ ID NO 15 | F3 gag | CATAGCAGGAACTACTAGTA | 1494-1513 |
| SEQ ID NO 16 | GAG_F_1602 | TAAAATAGTAAGAATGTATAGCCC | 1602-1625 |
| SEQ ID NO 17 | F5 gag | ATGACAGCATGTCAGGGAGT | 1828-1847 |
| SEQ ID NO 18 | F1 | GAGAGCTTCAGGTTTGGGG | 2170-2188 |
| SEQ ID NO 19 | F5 | CACTCTTTGGCAACGACCC | 2261-2279 |
| SEQ ID NO 20 | PR_F2376 | TGGAAACCAAAAATGATAGG | 2376-2395 |
| SEQ ID NO 21 | F2 | AATTGGGCCTGAAAATCC | 2696-2713 |
| SEQ ID NO 22 | F3 | CCTCCATTCCTTTGGATGGG | 3222-3241 |
| SEQ ID NO 23 | RT_F_3681 | GAAAGCATAGTAATATGGG | 3681-3699 |
| SEQ ID NO 24 | IN_F_4074 | CAACCAGATAAAAGTGAATCAG | 4074-4095 |
| SEQ ID NO 25 | IN_F_4540 | TAGCAGGAAGATGGCCAGT | 4540-4558 |
| SEQ ID NO 26 | Inseq3F | GTAGACATAATAGCAACAGAC | 4830-4850 |
| SEQ ID NO 55 | F7 | GTACTGGATGTGGGTGATGC | 2871-2890 |
| SEQ ID NO 56 | F8 | GTGGGAAAATTGAATTGGG | 3330-3348 |
| SEQ ID NO 57 | F3771 | GCCACCTGGATTCCTGAGTG | 3771-3790 |
| Reverse primers | | | |
| SEQ ID NO 27 | R8 gag | TCTTGTGGGGTGGCTCCTTC | 1337-1318 |
| SEQ ID NO 28 | GAG_R_1316 | TCTTGTGGGGTGGCTCCTTCTG | 1337-1316 |
| SEQ ID NO 29 | R3 gag | TCTACATAGTCTCTAAAGGG | 1682-1663 |
| SEQ ID NO 30 | GAG_R_1825 | ACTCCCTGACATGCTGTCATCAT | 1847-1825 |
| SEQ ID NO 31 | R7 gag | GTGGGGCTGTTGGCTCTGGT | 2164-2145 |
| SEQ ID NO 32 | PR_R_2382 | ATTCCCCCTATCATTTTTGG | 2401-2382 |
| SEQ ID NO 33 | R8 | GATAAAACCTCCAATTCC | 2414-2397 |
| SEQ ID NO 34 | R3 | CTTCCCAGAAGTCTTGAGTTC | 2817-2797 |
| SEQ ID NO 35 | R6 | GGAATATTGCTGGTGATCC | 3030-3012 |
| SEQ ID NO 36 | RT_R_3304 | TGTATGTCATTGACAGTCC | 3322-3304 |
| SEQ ID NO 37 | R5 | GGGTCATAATACACTCCATG | 3511-3492 |
| SEQ ID NO 38 | R1 | CTCCCACTCAGGAATCC | 3794-3778 |
| SEQ ID NO 39 | RT_R_3964 | CAGTCTTCTGATTTGTTG | 3981-3964 |
| SEQ ID NO 40 | RT_R_4150 | CTTTGTGTGCTGGTACCCATG | 4170-4150 |
| SEQ ID NO 41 | RT_R_4380a | GGACTACAGTCTACTTGTCCAATG | 4402-4380 |
| SEQ ID NO 42 | Inseq2R | CTGCCATTTGTACTGCTGTC | 4767-4748 |
| SEQ ID NO 43 | IN_R_5042 | ATCACCTGCCATCTGTTTTCCA | 5063-5042 |

TABLE 10-continued

Primer sequences of all sequencing primers and their position on the HXB2 reference.

| Primer name | Nucleotide sequence (5' → 3') | Position on HXB2 |
|---|---|---|
| SEQ ID NO 44 VIF_R_5193 | ATGTGTACTTCTGAACTT | 5210-5193 |
| SEQ ID NO 58 IN_R_4348 | CTCCTTTTAGCTGACATTTATCAC | 4371-4348 |

Creation of the HXB2D_eGFP_Delta[GAG-POL] Backbone (SEQ ID NO: 49)

This backbone contains all genetic elements of HIV-1, except the complete GAG and POL region. Recombination between this GAG-POL deletion backbone and the 5'LTR-VIF amplicon resulted in a fully functional HIV-1 viral vector, which was used in transfection/infection experiments.

First, pUC18 was digested with PstI and EcoRI restriction enzymes. Subsequently, a 35 bp synthetic linker containing the HpaI, SpeI, and SalI restriction sites was ligated into the PstI/EcoRI-linearized pUC18 plasmid, creating pUC18-LINK. Next, HXB2D_eGFP (original fully replication competent HIV-1 vector, containing eGFP in Nef) was digested with HpaI and SalI (termed vector C), cutting out the 5' part of the HIV-1 genome (5'LTR, GAG, POL, VIF) (from nucleotide 15223 to 5786 compared to the HXB2 reference), termed fragment A. Fragment A was then cloned into the HpaI/SalI-digested pUC18-LINK plasmid. PCR primers that are complementary to the 5' and 3' ends of the 5'LTR-Vif amplicon were designed and used in an 'inverse PCR' (iPCR) reaction to 're-create' the nucleotide sequence that was removed in excess during HpaI/SalI digestion (i.e. sequence between primer binding site and restriction site). These inverse PCR primers were extended with the nucleotide sequences of two restriction sites (i.e. PacI and SnaBI) for linearization of the backbone afterwards. Finally, HpaI/SalI digestion was performed on the iPCR product and the excised HpaI/SalI fragment (fragment B) was cloned back into the HpaI/SalI digested original HXB2D-eGFP vector (vector C) (see FIG. 1, 2, 3).

Creation of the HXB2D_eGFP_Delta[POL] Backbone (SEQ ID NO: 52)

This backbone contains all genetic elements of HIV-1, except the complete Pol region. Recombination between this Pol deletion backbone and the Pol amplicon resulted in a fully functional HIV-1 viral vector, which was used in transfection/infection experiments.

First, pUC18 was digested with PstI and EcoRI restriction enzymes. Subsequently, a 35 bp synthetic linker containing the HpaI, SpeI, and SalI restriction sites was ligated into the PstI/EcoRI-linearized pUC18 plasmid, creating pUC18-LINK. Next, HXB2D_eGFP (original fully replication competent HIV-1 vector, containing eGFP in Nef) was digested with HpaI and SalI (termed vector C), cutting out the 5' part of the HIV-1 genome (5'LTR, GAG, POL, VIF) (from nucleotide 15223 to 5786 compared to the HXB2 reference), termed fragment A. Fragment A was then cloned into the HpaI/SalI-digested pUC18-LINK plasmid. PCR primers that are complementary to the 5' and 3' ends of the Pol amplicon were designed and used in an 'inverse PCR' (iPCR) reaction to 're-create' the nucleotide sequence that was removed in excess during HpaI/SalI digestion (i.e. sequence between primer binding site and restriction site). These inverse PCR primers were extended with the nucleotide sequences of two restriction sites (i.e. PacI and SnaBI) for linearization of the backbone afterwards. Finally, HpaI/SalI digestion was performed on the iPCR product and the excised HpaI/SalI fragment (fragment P) was cloned back into the HpaI/SalI digested original HXB2D-eGFP vector (vector C) (see FIGS. 12 and 13).

Creation of the HXB2D_eGFP_Delta[RT-INT] Backbone (SEQ ID NO: 51)

This backbone contains all genetic elements of HIV-1, except the complete RT and INT region. Recombination between this RT-INT deletion backbone and the RT-INT amplicon resulted in a fully functional HIV-1 viral vector, which was used in transfection/infection experiments.

First, pUC18 was digested with PstI and EcoRI restriction enzymes. Subsequently, a 35 bp synthetic linker containing the HpaI, SpeI, and SalI restriction sites was ligated into the PstI/EcoRI-linearized pUC18 plasmid, creating pUC18-LINK. Next, HXB2D_eGFP (original fully replication competent HIV-1 vector, containing eGFP in Nef) was digested with SpeI and SalI (termed vector Z), cutting out the majority of POL and VIF of the HIV-1 genome (from nucleotide 1507 to 5786 compared to the HXB2 reference), termed fragment X. Fragment X was then cloned into the SpeI/SalI-digested pUC18-LINK plasmid. PCR primers that are complementary to the 5' and 3' ends of the RT-INT amplicon were designed and used in an 'inverse PCR' (iPCR) reaction to 're-create' the nucleotide sequence that was removed in excess during SpeI/SalI digestion (i.e. sequence between primer binding site and restriction site).

Finally, SpeI/SalI digestion was done on the iPCR product and the excised SpeI/SalI fragment (fragment Y) was cloned back into the SpeI/SalI digested original HXB2D-eGFP vector (vector Z) (see FIG. 4, 5, 6).

Creation of the HXB2D_eGFP_delta[GAG-PR] Backbone (SEQ ID NO: 50)

This backbone contains all genetic elements of HIV-1, except the complete GAG and PR region. Recombination between this GAG-PR deletion backbone and the GAG-PR amplicon resulted in a fully functional HIV-1 viral vector, which was used in transfection/infection experiments.

First, pUC18 was digested with PstI and EcoRI restriction enzymes. Subsequently, a 35 bp synthetic linker containing the HpaI, SpeI, and SalI restriction sites was ligated into the PstI/EcoRI-linearized pUC18 plasmid, creating pUC18-LINK. Next, HXB2D_eGFP (original fully replication competent HIV-1 vector, containing eGFP in Nef) was digested with HpaI and SalI (termed vector C), cutting out the 5' part of the HIV-1 genome (5'LTR, GAG, POL, VIF) (from nucleotide 15223 to 5786 compared to the HXB2 reference), termed fragment A. Fragment A was then cloned into the HpaI/SalI-digested pUC18-LINK plasmid. PCR primers that are complementary to the 5' and 3' ends of the GAG-PR amplicon were designed and used in an 'inverse PCR' (iPCR) reaction to 're-create' the nucleotide sequence that was removed in excess during HpaI/SalI digestion (i.e. sequence between primer binding site and restriction site). Finally, HpaI/SalI digestion was done on the iPCR product and the excised HpaI/SalI fragment (fragment ALPHA) was cloned back into the HpaI/SalI digested original HXB2D-eGFP vector (vector C) (see FIG. 7, 8, 9).

Phenotypic Assay Approach

After linearization of the Gag-Pol, Gag-PR and RT-INT HXB2D_eGFP_delta backbone described before, the respective purified amplicon was cloned in the appropriate backbone using the In-Fusion™ technology (Clontech, Mountain view, California) and subsequently transformed into MAX Efficiency® Stbl2™ cells (Invitrogen, Merelbeke, Belgium). After DNA preparation from either clones or the complete plate, full-length recombinant HIV genomes were transfected to MT4 cells. At full CPE, recombinant virus stocks were harvested, titrated and subjected to an antiviral experiment.

The 3 phenotyping assays (GAG-POL, GAG-PR and RT-INT) are described in the following section. The layout of the experiments is shown in FIG. 10.

The three backbones, HXB2D_eGFP_delta [GAG-POL] (SEQ ID NO: 49), HXB2D_eGFP_delta [GAG-PR] (SEQ ID NO: 50) and HXB2D_eGFP_delta [RT-INT] (SEQ ID NO: 51) were linearized by digestion with SnaBI and PacI. After purification, for each backbone, 100 ng linearized vector was recombined with three different PCR amplicons (3×5'LTR-VIF, 3× GAG-PR or 3×RT-INT amplicons) in vector/insert molar ratio of 1/10 using In-Fusion reagents. Thereafter, In-Fusion mixes were transformed to MAX Efficiency Stbl2 cells and incubated for 24 h at 30° C. The day after, colonies were screened for the presence of the full recombinant plasmid by a duplex colony PCR using the primers shown in Table 11 (SEQ ID NO's: 45-48).

As an example, full recombinants generate two fragments (493 bp and 217 bp), while recirculatized vectors containing no inserts, generate only one fragment (300 bp for delta_[GAG-POL], 200 bp for delta_[GAG-PR] and 500 bp for delta_[RT-INT]).

In general full-length HIV recombinants were obtained for all backbones and for all amplicons tested.

For the GAG-POL assay, two full recombinants were obtained for sample 1 and 2, and three recombinants for sample 3.

For the GAG-PR backbone, two recombinants were generated for sample 1, one recombinant for sample 2 and eight recombinants for sample 3.

For the RT-INT backbone, five full recombinants for sample 1, eleven recombinants for sample 2 and two for sample 3 were generated.

Figure 11B:
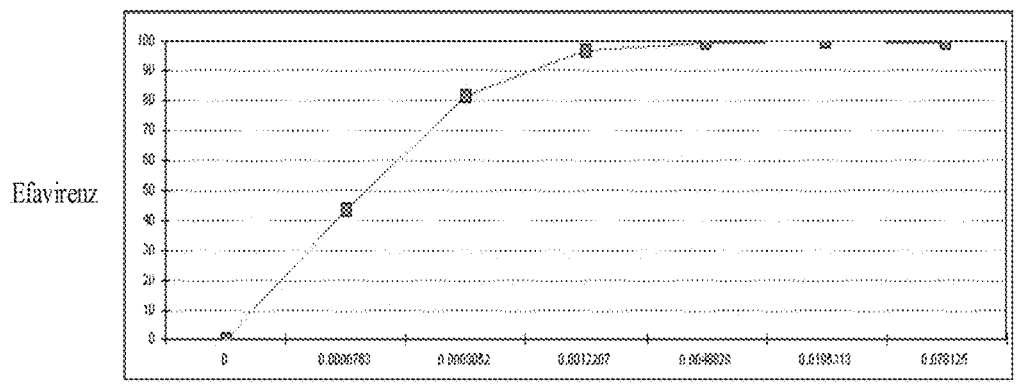
Figure 11C:
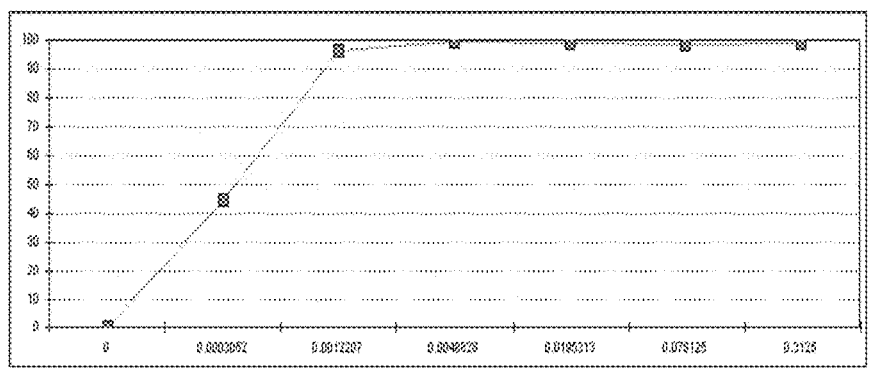
Figure 11D:
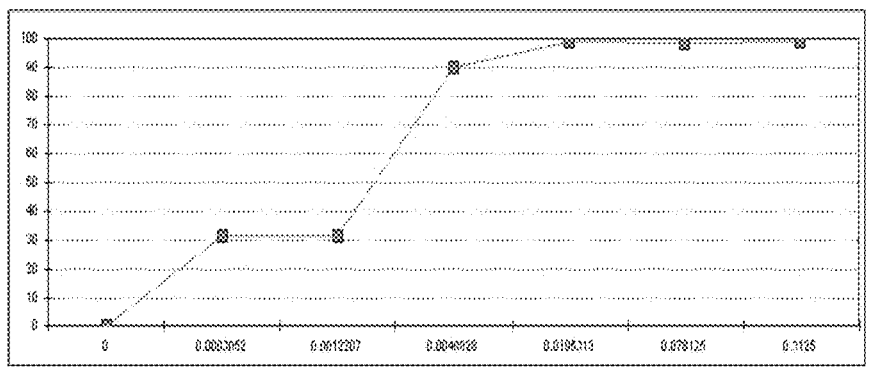
Figure 11E:
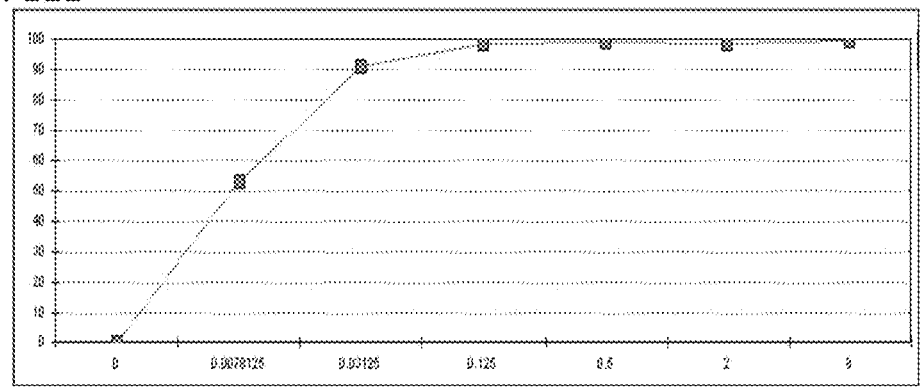
Figure 11F:
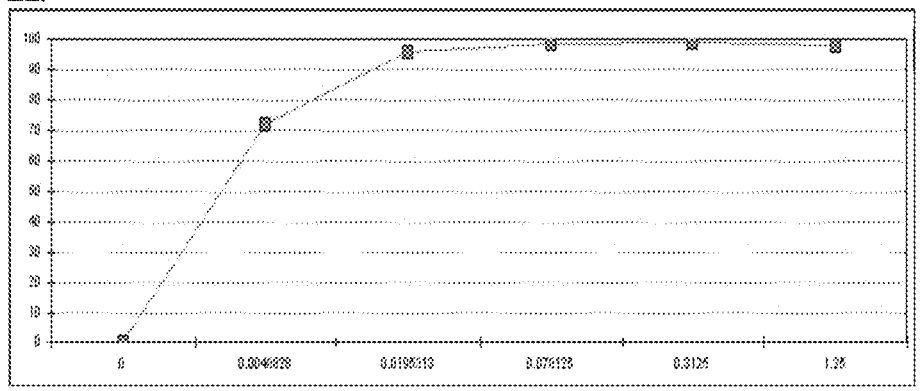
Figure 11G:
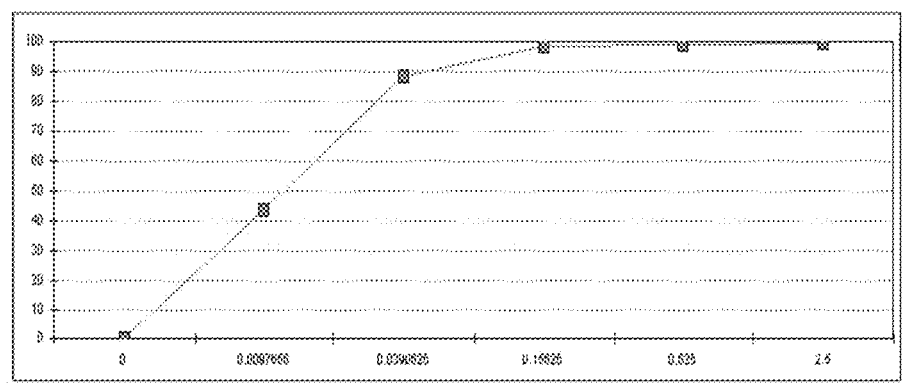
Figure 11H:
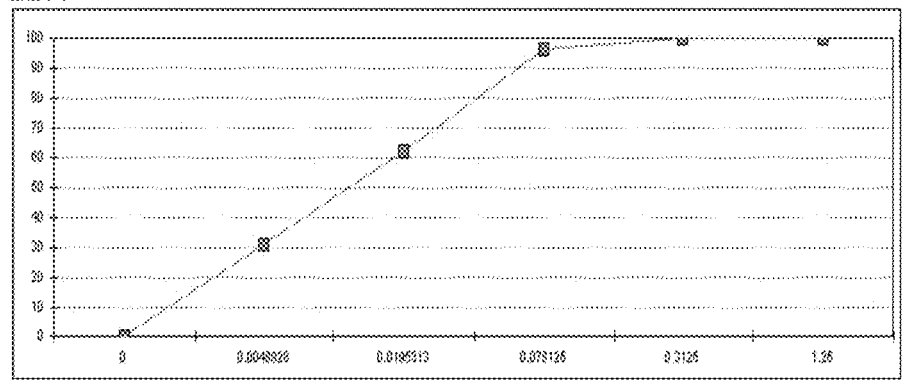
Figure 11I:
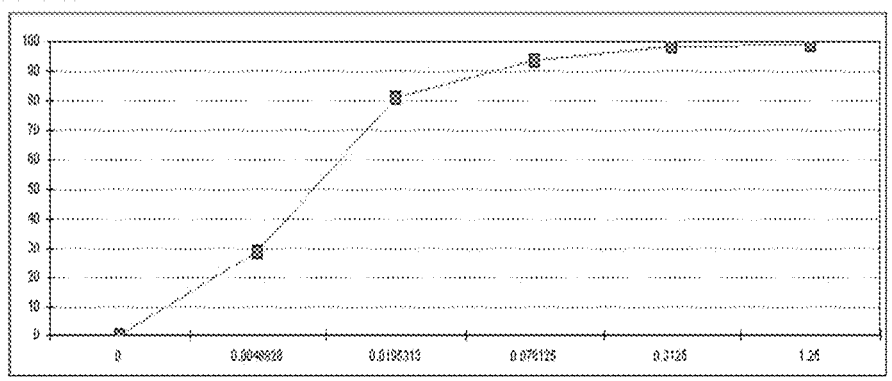
Figure 11J:
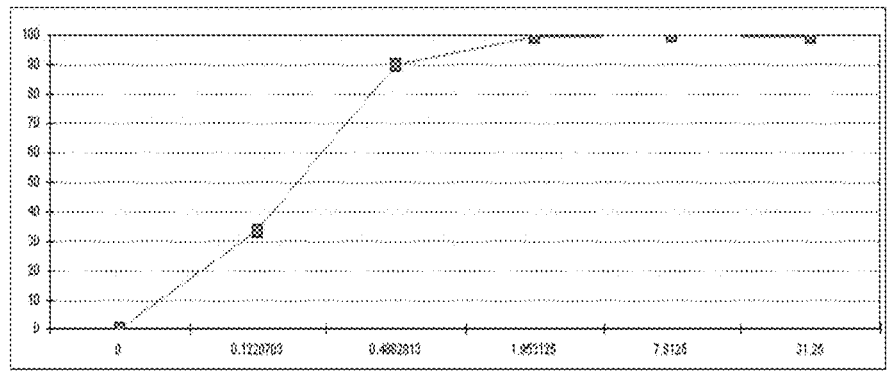
Figure 11K:
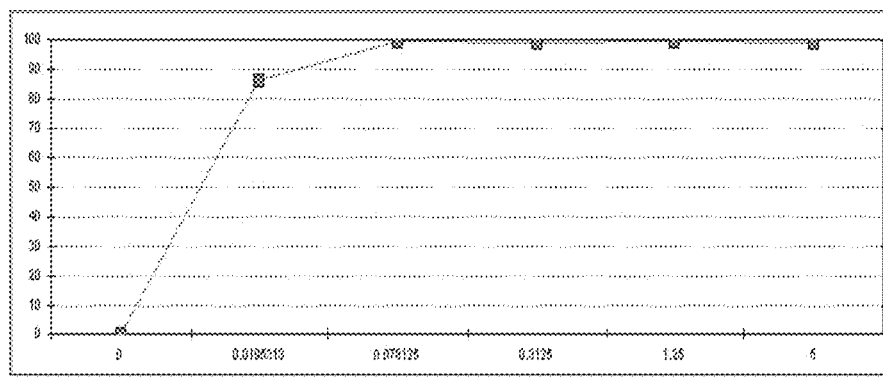
Figure 11L:
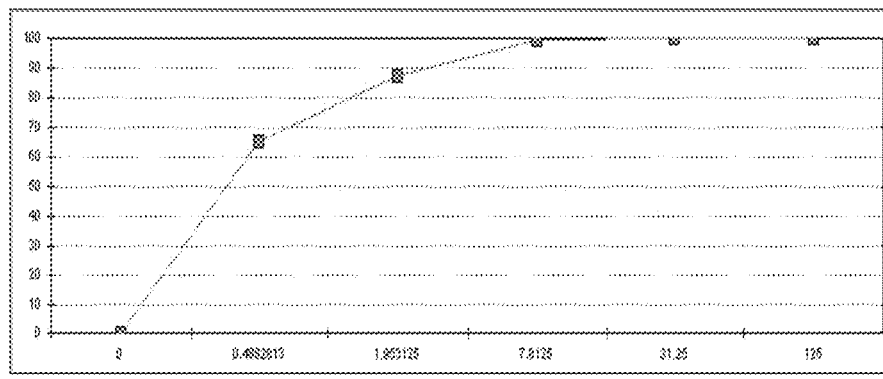
Figure 11M:
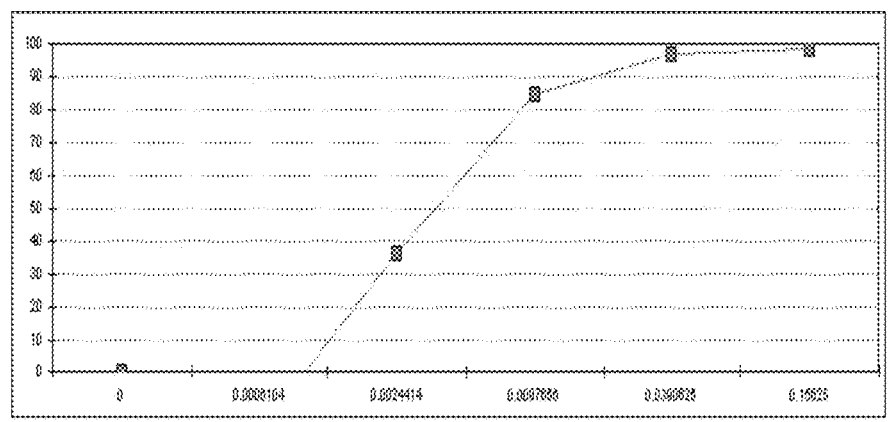
Figure 11N:
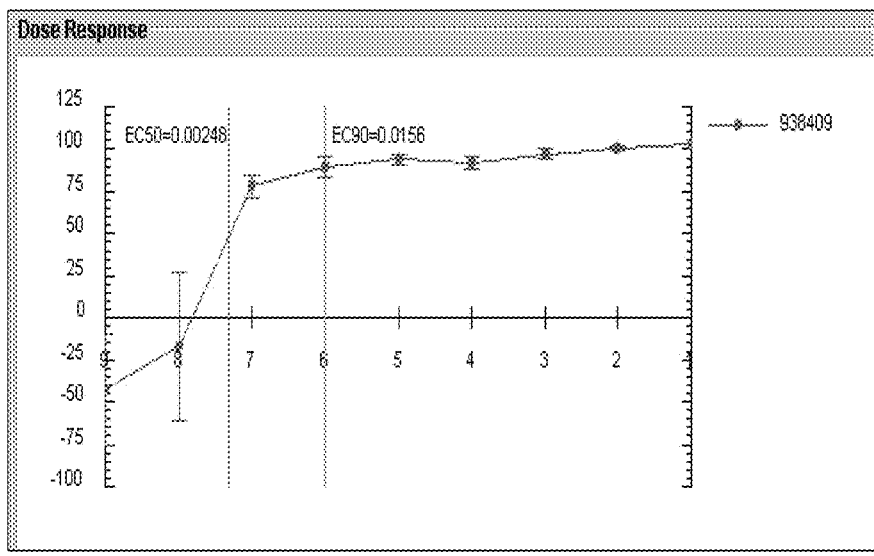
Figure 11O:
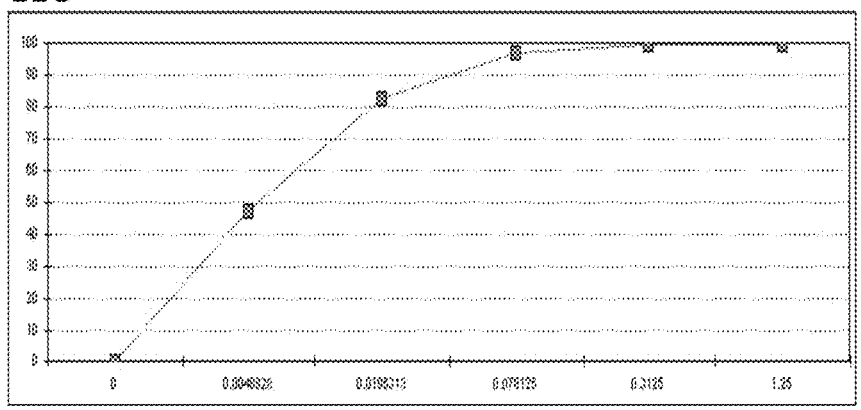
Figure 11P:
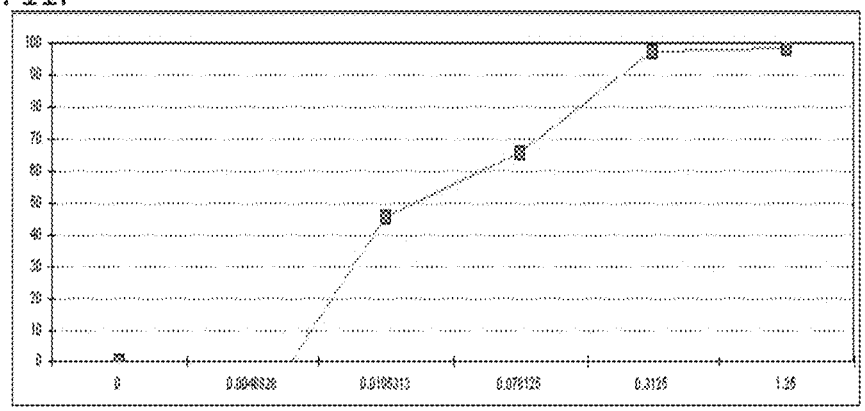
Figure 11Q:
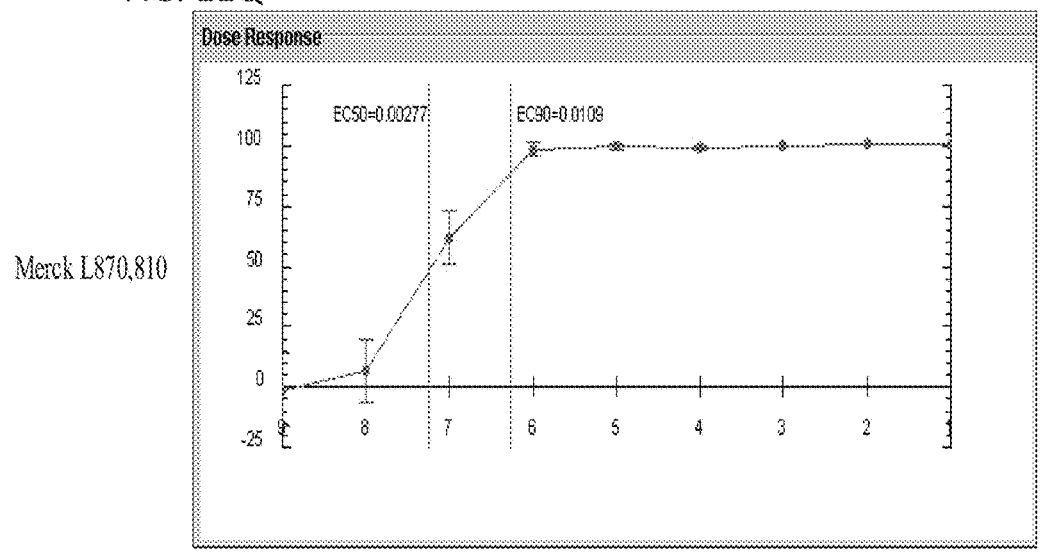
Figure 11R:
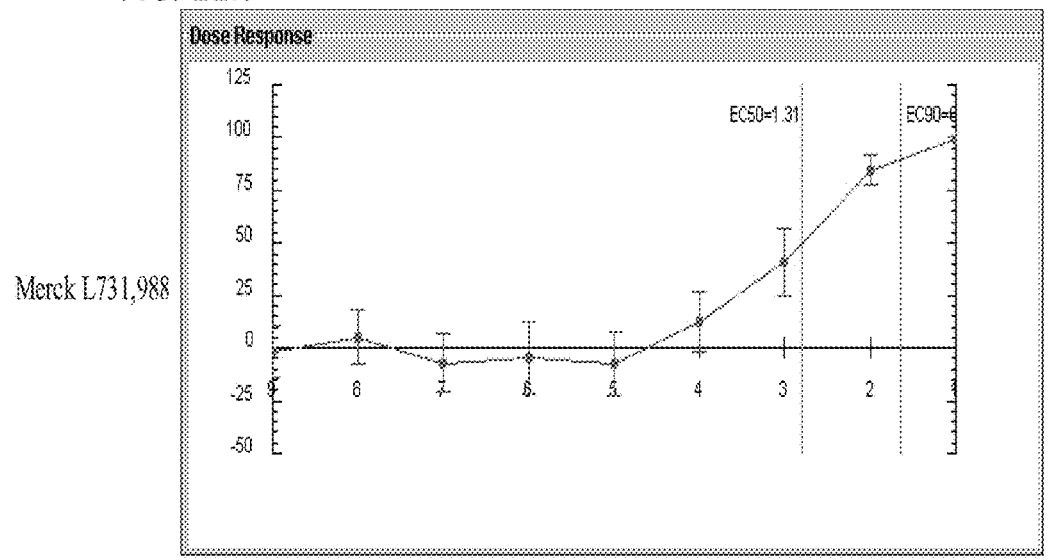

All recombinant clones (with a maximum of five per sample) were grown overnight in LB-ampicillin at 30° C. to prepare DNA from (27 in total). Miniprep DNA was prepared using the Qiaprep Spin miniprep (Qiagen) and checked by HindIII restriction digest. By comparison of the HindIII digestion pattern of the clones with that of the deletion backbones and that of the full-length parental HXB2D_eGFP vector, all 27 clones contained full-length HIV genomes. All 27 clones were transfected to MT4 cells using the Amaxa nucleofection technique and evaluated for their cythopathic effect (CPE). In total, 18 clones reached full CPE (cytopathogenic effect) during the time of evaluation (11 days) and were used for further infection experiments: 16 clones generated full CPE after 4 days, 1 clone after 5 days and 1 clone after 11 days. The other 9 clones did not show substantial infection after 11 days and were stopped for further analysis. The 18 harvested RVS (recombinant virus stock) were titrated and subjected to an antiviral experiment (AVE) at a standardized MOI (multiplicity of infection) using FDA-approved protease and RT inhibitors, and experimental maturation (PA-457) and integrase (GS-9137, L870,810 and L731,988) inhibitors. After 3 days of infection, GFP (green fluorescent protein) infection signals were quantified and dose-response curves were calculated. Only 1 out of 18 samples did not generate significant GFP expression above background, all other 17 RVS were successfully phenotyped for all drugs tested. As an example, FIG. 11 shows the dose-response curves 1 GAG-POL RVS for all drugs tested.

TABLE 11

Primer sequences of the primers used for the colony PCR and their position on the HXB2 reference.

| primer name | primer sequence from 5' to 3' | Position on HXB2 |
| --- | --- | --- |
| SEQ ID NO 45: HXB2_5LTR_F_422 | CTG CAT ATA AGC AGC TGC TTT TTG | 422-445 |
| SEQ ID NO 46: GAG_R_895 | TCT AGC TCC CTG CTT GCC CA | 895-914 |
| SEQ ID NO 47: IN_F_5052 | ATG GCA GGT GAT GAT TGT GTG G | 5052-5073 |
| SEQ ID NO 48: HXB2_VIF_R_5247 | TTC TCC TGT ATG CAG ACC CCA A | 5247-5268 |

What is claimed:

1. An in vitro method for designing a drug regime for an HIV-infected patient by determining the phenotypic susceptibility of HIV to at least one drug, comprising:
  i) using at least one sample comprising HIV RNA from a patient, wherein the sample comprises the complete HIV reverse transcriptase-integrase coding sequence;
  ii) reverse-transcribing and amplifying the HIV RNA with primers specific for the complete HIV reverse transcriptase-integrase coding sequence to obtain at least one amplicon comprising the complete HIV reverse transcriptase-integrase coding sequence, wherein at least one primer comprises one of SEQ ID NO: 4-7;
  iii) generating a plasmid comprising a reference HIV sequence with a deletion of the complete HIV reverse transcriptase-integrase coding sequence, wherein said plasmid comprises SEQ ID NO:51;
  iv) preparing at least one recombinant virus by recombination or ligation between at least one amplicon obtained in step ii) and the plasmid comprising the reference HIV sequence with a deletion of the complete HIV reverse transcriptase-integrase coding sequence obtained in step iii), and v) monitoring at least one recombinant virus in the presence of at least one drug to determine the phenotypic susceptibility of HIV to at least one drug, wherein said susceptibility is determined by the cytopathogenicity of said recombinant virus to cells or by determining the replicative capacity of said recombinant virus in the presence of at least one drug.

2. An in vitro method for designing a drug regime for an HIV-infected patient by determining the phenotypic susceptibility of HIV to at least one drug, comprising:
 i) using at least one sample comprising HIV DNA, wherein the sample comprises the complete HIV reverse transcriptase-integrase coding sequence;
 ii) amplifying the HIV DNA with primers specific for the complete HIV reverse transcriptase-integrase coding sequence to obtain at least one amplicon comprising the complete HIV reverse transcriptase-integrase coding sequence, wherein at least one primer comprises one of SEQ ID NO: 4-7;
 iii) generating a plasmid comprising a reference HIV sequence with a deletion of the complete HIV reverse transcriptase-integrase coding sequence, wherein said plasmid comprises SEQ ID NO:51;
 iv) preparing at least one recombinant virus by recombination or ligation between at least one amplicon obtained in step ii) and the plasmid comprising the reference HIV sequence with a deletion of the complete HIV reverse transcriptase-integrase coding sequence obtained in step iii), and
 v) monitoring at least one recombinant virus in the presence of at least one drug to determine the phenotypic susceptibility of HIV to at least one drug, wherein said susceptibility is determined by the cytopathogenicity of said recombinant virus to cells or by determining the replicative capacity of said recombinant virus in the presence of at least one drug.

* * * * *

SEQUENCE LISTING

<160> NUMBER OF SEQ ID NOS: 73

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
tggaaaatct ctagcagtgg cg                                              22

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
agtgggatgt gtacttctga ac                                              22

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tctctagcag tggcgcccga aca                                             23

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gggatgtgta cttctgaact t                                               21

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ccctcaaatc actctttggc aacgac                                          26

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ctcctgtatg cagaccccaa tatg                                            24

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gctctattag atacaggagc agatg                                           25

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
caagtagtgt gtgcccgtct gt                                              22

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ccattgttta acttttgggc catcc                                           25

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ccattcctgg ctttaatttt actgg                                           25

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
agcagtggcg cccgaacag                                                  19

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tttgactagc gggaggctag aag                                             23

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
taaaagacac caaggaagc                                                  19

<210> SEQ ID NO 14
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
aagacaccaa ggaagc                                                      16

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
catagcagga actactagta                                                  20

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
taaaatagta agaatgtata gccc                                             24

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
atgacagcat gtcagggagt                                                  20

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gagagcttca ggtttgggg                                                   19

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cactctttgg caacgaccc                                                   19

```
<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tggaaaccaa aaatgatagg                                                 20

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
aattgggcct gaaaatcc                                                   18

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cctccattcc tttggatggg                                                 20

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gaaagcatag taatatggg                                                  19

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
caaccagata aaagtgaatc ag                                              22

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tagcaggaag atggccagt                                                  19

<210> SEQ ID NO 26
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gtagacataa tagcaacaga c                                              21

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tcttgtgggg tggctccttc                                                20

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tcttgtgggg tggctccttc tg                                             22

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
tctacatagt ctctaaaggg                                                20

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
actccctgac atgctgtcat cat                                            23

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gtggggctgt tggctctggt                                                20

<210> SEQ ID NO 32
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
attcccccta tcatttttgg                                              20

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gataaaacct ccaattcc                                                18

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cttcccagaa gtcttgagtt c                                            21

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ggaatattgc tggtgatcc                                               19

<210> SEQ ID NO 36
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tgtatgtcat tgacagtcc                                               19

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gggtcataat acactccatg                                              20

<210> SEQ ID NO 38
<211> LENGTH: 17
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 38
ctcccactca ggaatcc                                                      17

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
cagtcttctg atttgttg                                                     18

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ctttgtgtgc tggtacccat g                                                 21

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ggactacagt ctacttgtcc aatg                                              24

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ctgccatttg tactgctgtc                                                   20

<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
atcacctgcc atctgttttc ca                                                22

<210> SEQ ID NO 44
<211> LENGTH: 18
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 44
atgtgtactt ctgaactt                                                    18

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ctgcatataa gcagctgctt tttg                                             24

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
tctagctccc tgcttgccca                                                  20

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
atggcaggtg atgattgtgt gg                                               22

<210> SEQ ID NO 48
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ttctcctgta tgcagacccc aa                                               22

<210> SEQ ID NO 49
<211> LENGTH: 10992
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
tggaagggct aattcactcc caaagaagac aagatatcct tgatctgtgg atctaccaca      60
cacaaggcta cttccctgat tagcagaact acacaccagg gccagggtca gatatccact     120
gacctttgga tggtgctaca agctagtacc agttgagcca gataaggtag aagaggccaa     180
taaaggagag aacaccagct tgttacaccc tgtgagcctg catgggatgg atgacccgga     240
```

```
gagagaagtg ttagagtgga ggtttgacag ccgcctagca tttcatcacg tggcccgaga    300
gctgcatccg gagtacttca agaactgctg atatcgagct tgctacaagg gactttccgc    360
tggggacttt ccagggaggc gtggcctggg cgggactggg gagtggcgag ccctcagatc    420
ctgcatataa gcagctgctt tttgcctgta ctgggtctct ctggttagac cagatctgag    480
cctgggagct ctctggctaa ctagggaacc cactgcttaa gcctcaataa agcttgcctt    540
gagtgcttca agtagtgtgt gcccgtctgt tgtgtgactc tggtaactag agatccctca    600 gacccttta gtcagtgtgg aaaatctcta gcagtggcgt taattaaccg tacgcgtact    660
acgtaagaag tacacatccc actaggggat gctagattgg taataacaac atattggggt    720
ctgcatacag gagaaagaga ctggcatttg ggtcagggag tctccataga atggaggaaa    780
aagagatata gcacacaagt agaccctgaa ctagcagacc aactaattca tctgtattac    840
tttgactgtt tttcagactc tgctataaga aaggccttat taggacacat agttagccct    900
aggtgtgaat atcaagcagg acataacaag gtaggatctc tacaatactt ggcactagca    960
gcattaataa caccaaaaaa gataaagcca cctttgccta gtgttacgaa actgacagag   1020
gatagatgga acaagcccca gaagaccaag ggccacagag ggagccacac aatgaatgga   1080
cactagagct tttagaggag cttaagaatg aagctgttag acattttcct aggatttggc   1140
tccatggctt agggcaacat atctatgaaa cttatgggga tacttgggca ggagtggaag   1200
ccataataag aattctgcaa caactgctgt ttatccattt tcagaattgg gtgtcgacat   1260
agcagaatag gcgttactcg acagaggaga gcaagaaatg gagccagtag atcctagact   1320
agagccctgg aagcatccag gaagtcagcc taaaactgct tgtaccaatt gctattgtaa   1380
aaagtgttgc tttcattgcc aagtttgttt cataacaaaa gccttaggca tctcctatgg   1440
caggaagaag cggagacagc gacgaagagc tcatcagaac agtcagactc atcaagcttc   1500
tctatcaaag cagtaagtag tacatgtaac gcaacctata ccaatagtag caatagtagc   1560
attagtagta gcaataataa tagcaatagt tgtgtggtcc atagtaatca tagaatatag   1620
gaaaatatta agacaaagaa aaatagacag gttaattgat agactaatag aaagagcaga   1680
agacagtggc aatgagagtg aaggagaaat atcagcactt gtggagatgg gggtggagat   1740
ggggcaccat gctccttggg atgttgatga tctgtagtgc tacagaaaaa ttgtgggtca   1800
cagtctatta tggggtacct gtgtggaagg aagcaaccac cactctattt tgtgcatcag   1860
atgctaaagc atatgataca gaggtacata atgtttgggc cacacatgcc tgtgtaccca   1920
cagaccccaa cccacaagaa gtagtattgg taaatgtgac agaaaatttt aacatgtgga   1980
aaaatgacat ggtagaacag atgcatgagg atataatcag tttatgggat caaagcctaa   2040
agccatgtgt aaaattaacc ccactctgtg ttagtttaaa gtgcactgat ttgaagaatg   2100
atactaatac caatagtagt agcgggagaa tgataatgga gaaggagag ataaaaaact   2160 gctctttcaa tatcagcaca agcataagag gtaaggtgca gaaagaatat gcattttttt   2220
ataaacttga tataatacca atagataatg atactaccag ctataagttg acaagttgta   2280
acacctcagt cattacacag gcctgtccaa aggtatcctt tgagccaatt cccatacatt   2340
attgtgcccc ggctggtttt gcgattctaa atgtaataa taagacgttc aatggaacag   2400
gaccatgtac aaatgtcagc acagtacaat gtacacatgg aattaggcca gtagtatcaa   2460
ctcaactgct gttaaatggc agtctagcag aagaagaggt agtaattaga tctgtcaatt   2520
tcacggacaa tgctaaaacc ataatagtac agctgaacac atctgtagaa attaattgta   2580
caagacccaa caacaataca agaaaaagaa tccgtatcca gagaggacca gggagagcat   2640
```

| | |
|---|---|
| ttgttacaat aggaaaaata ggaaatatga gacaagcaca ttgtaacatt agtagagcaa | 2700 |
| aatggaataa cactttaaaa cagatagcta gcaaattaag agaacaattt ggaaataata | 2760 |
| aaacaataat ctttaagcaa tcctcaggag gggacccaga aattgtaacg cacagtttta | 2820 |
| attgtggagg ggaatttttc tactgtaatt caacacaact gtttaatagt acttggttta | 2880 |
| atagtacttg gagtactgaa gggtcaaata cactgaagg aagtgacaca atcaccctcc | 2940 |
| catgcagaat aaaacaaatt ataaacatgt ggcagaaagt aggaaaagca atgtatgccc | 3000 |
| ctcccatcag tggacaaatt agatgttcat caaatattac agggctgcta ttaacaagag | 3060 |
| atggtggtaa tagcaacaat gagtccgaga tcttcagacc tggaggagga gatatgaggg | 3120 |
| acaattggag aagtgaatta tataaatata agtagtaaaa aattgaacca ttaggagtag | 3180 |
| cacccaccaa ggcaaagaga agagtggtgc agagagaaaa aagagcagtg ggaataggag | 3240 |
| cttttgttcct tgggttcttg ggagcagcag gaagcactat gggcgcagcg tcaatgacgc | 3300 |
| tgacggtaca ggccagacaa ttattgtctg gtatagtgca gcagcagaac aatttgctga | 3360 |
| gggctattga ggcgcaacag catctgttgc aactcacagt ctggggcatc aagcagctcc | 3420 |
| aggcaagaat cctggctgtg gaaagatacc taaaggatca acagctcctg ggatttgggg | 3480 |
| gttgctctgg aaaactcatt tgcaccactg ctgtgccttg gaatgctagt tggagtaata | 3540 |
| aatctctgga acagatttgg aatcacacga cctggatgga gtgggacaga gaaattaaca | 3600 |
| attacacaag cttaatacac tccttaattg aagaatcgca aaaccagcaa gaaaagaatg | 3660 |
| aacaagaatt attggaatta gataaatggg caagtttgtg gaattggttt aacataacaa | 3720 |
| attggctgtg gtatataaaa ttattcataa tgatagtagg aggcttggta ggtttaagaa | 3780 |
| tagttttgc tgtactttct atagtgaata gagttaggca gggatattca ccattatcgt | 3840 |
| ttcagaccca cctcccaacc ccgaggggac ccgacaggcc cgaaggaata agaagaagaa | 3900 |
| gtggagagag agacagagac agatccattc gattagtgaa cggatcctta gcacttatct | 3960 |
| gggacgatct gcggagcctg tgcctcttca gctaccaccg cttgagagac ttactcttga | 4020 |
| ttgtaacgag gattgtggaa cttctgggac gcaggggtg ggaagccctc aaatattggt | 4080 |
| ggaatctcct acaatattgg agtcaggagc taaagaatag tgctgttagc ttgctcaatg | 4140 |
| ccacagccat agcagtagct gaggggacag ataggggttat agaagtagta caaggagctt | 4200 |
| gtagagctat tcgccacata cctagaagaa taagacaggg cttggaaagg attttgctat | 4260 |
| aagatgggtg gcgcggccgc aatggtgagc aagggcgagg agctgttcac cggggtggtg | 4320 |
| cccatcctgg tcgagctgga cggcgacgta aacggccaca gttcagcgt gtccggcgag | 4380 |
| ggcgagggcg atgccaccta cggcaagctg accctgaagt tcatctgcac caccggcaag | 4440 |
| ctgcccgtgc cctggcccac cctcgtgacc accctgacct acggcgtgca gtgcttcagc | 4500 |
| cgctaccccg accacatgaa gcagcacgac ttcttcaagt ccgccatgcc cgaaggctac | 4560 |
| gtccaggagc gcaccatctt cttcaaggac gacggcaact acaagacccg cgccgaggtg | 4620 |
| aagttcgagg gcgacaccct ggtgaaccgc atcgagctga agggcatcga cttcaaggag | 4680 |
| gacggcaaca tcctggggca caagctggag tacaactaca acagccacaa cgtctatatc | 4740 |
| atggccgaca agcagaagaa cggcatcaag gcgaacttca gatccgcca caacatcgag | 4800 |
| gacggcagcg tgcagctcgc cgaccactac cagcagaaca ccccatcgg cgacggcccc | 4860 |
| gtgctgctgc ccgacaacca ctacctgagc acccagtccg ccctgagcaa agaccccaac | 4920 |
| gagaagcgcg atcacatggt cctgctggag ttcgtgaccg ccgccgggat cactctcggc | 4980 |

```
atggacgagc tgtacaagta agaattctga ctcgagacct agaaaaacat ggagcaatca    5040
caagtagcaa tacagcagct accaatgctg attgtgcctg ctagaagca caagaggagg      5100 aggaggtggg ttttccagtc acacctcagg tacctttaag accaatgact tacaaggcag    5160
ctgtagatct tagccacttt ttaaaagaaa agggggact ggaagggcta attcactccc       5220
aacgaagaca agatatcctt gatctgtgga tctaccacac acaaggctac ttccctgatt    5280
ggcagaacta cacaccaggg ccagggatca gatatccact gacctttgga tggtgctaca    5340
agctagtacc agttgagcaa gagaaggtag aagaagccaa tgaaggagag aacacccgct    5400
tgttacaccc tgtgagcctg catgggatgg atgacccgga gagagaagta ttagagtgga    5460
ggtttgacag ccgcctagca tttcatcaca tggcccgaga gctgcatccg gagtacttca    5520
agaactgctg acatcgagct tgctacaagg gactttccgc tggggacttt ccagggaggc    5580
gtggcctggg cgggactggg gagtggcgag ccctcagatg ctgcatataa gcagctgctt    5640
tttgcttgta ctgggtctct ctggttagac cagatctgag cctgggagct ctctggctaa    5700
ctagggaacc cactgcttaa gcctcaataa agcttgcctt gagtgcttca agtagtgtgt    5760
gcccgtctgt tgtgtgactc tggcgcgcct ctagaattaa ttccgtgtat tctatagtgt    5820
cacctaaatc gtatgtgtat gatacataag gttatgtatt aattgtagcc gcgttctaac    5880
gacaatatgt acaagcctaa ttgtgtagca tctggcttac tgaagcagac cctatcatct    5940
ctctcgtaaa ctgccgtcag agtcggtttg gttggacgaa ccttctgagt ttctggtaac    6000
gccgtcccgc acccggaaat ggtcagcgaa ccaatcagca gggtcatcgc tagccagatc    6060
ctctacgccg gacgcatcgt ggccggcatc accggcgcca caggtgcggt tgctggcgcc    6120
tatatcgccg acatcaccga tggggaagat cgggctcgcc acttcgggct catgagcgct    6180
tgtttcggcg tgggtatggt ggcaggcccc gtggccgggg gactgttggg cgccatctcc    6240
ttgcatgcac cattccttgc ggcggcggtg ctcaacggcc tcaacctact actgggctgc    6300
ttcctaatgc aggagtcgca taagggagag cgtcgaatgg tgcactctca gtacaatctg    6360
ctctgatgcc gcatagttaa gccagccccg acacccgcca cacccgctg acgcgccctg    6420 acgggcttgt ctgctcccgg catccgctta cagacaagct gtgaccgtct ccgggagctg    6480
catgtgtcag aggttttcac cgtcatcacc gaaacgcgcg agacgaaagg cctcgtgat    6540 acgcctattt ttataggtta atgtcatgat aataatggtt tcttagacgt caggtggcac    6600
ttttcgggga aatgtgcgcg gaacccctat ttgtttattt ttctaaatac attcaaatat    6660
gtatccgctc atgagacaat aaccctgata aatgcttcaa taatattgaa aaggaagag    6720 tatgagtatt caacatttcc gtgtcgccct tattcccttt tttgcggcat tttgccttcc    6780 tgttttgct cacccagaaa cgctggtgaa agtaaaagat gctgaagatc agttgggtgc    6840
acgagtgggt tacatcgaac tggatctcaa cagcggtaag atccttgaga gttttcgccc    6900
cgaagaacgt tttccaatga tgagcacttt taaagttctg ctatgtggcg cggtattatc    6960
ccgtattgac gccgggcaag agcaactcgg tcgccgcata cactattctc agaatgactt    7020
ggttgagtac tcaccagtca cagaaaagca tcttacggat ggcatgacag taagagaatt    7080
atgcagtgct gccataacca tgagtgataa cactgcggcc aacttacttc tgacaacgat    7140
cggaggaccg aaggagctaa ccgcttttt gcacaacatg gggatcatg taactcgcct    7200 tgatcgttgg gaaccggagc tgaatgaagc cataccaaac gacgagcgtg acaccacgat    7260
gcctgtagca atggcaacaa cgttgcgcaa actattaact ggcgaactac ttactctagc    7320
ttcccggcaa caattaatag actggatgga ggcggataaa gttgcaggac cacttctgcg    7380
```

```
ctcggcccttt ccggctggct ggtttattgc tgataaatct ggagccggtg agcgtgggtc    7440
tcgcggtatc attgcagcac tggggccaga tggtaagccc tcccgtatcg tagttatcta    7500
cacgacgggg agtcaggcaa ctatggatga acgaaataga cagatcgctg agataggtgc    7560
ctcactgatt aagcattggt aactgtcaga ccaagtttac tcatatatac tttagattga    7620
tttaaaactt cattttttaat ttaaaaggat ctaggtgaag atccttttttg ataatctcat    7680 gaccaaaatc ccttaacgtg agttttcgtt ccactgagcg tcagaccccg tagaaaagat    7740
caaaggatct tcttgagatc ctttttttct gcgcgtaatc tgctgcttgc aaacaaaaaa    7800
accaccgcta ccagcggtgg tttgtttgcc ggatcaagag ctaccaactc ttttttccgaa    7860 ggtaactggc ttcagcagag cgcagatacc aaatactgtt cttctagtgt agccgtagtt    7920
aggccaccac ttcaagaact ctgtagcacc gcctacatac ctcgctctgc taatcctgtt    7980
accagtggct gctgccagtg gcgataagtc gtgtcttacc gggttggact caagacgata    8040
gttaccggat aaggcgcagc ggtcgggctg aacggggggt tcgtgcacac agcccagctt    8100
ggagcgaacg acctacaccg aactgagata cctacagcgt gagctatgag aaagcgccac    8160
gcttcccgaa gggagaaagg cggacaggta tccggtaagc ggcagggtcg gaacaggaga    8220
gcgcacgagg gagcttccag ggggaaacgc ctggtatctt tatagtcctg tcgggtttcg    8280
ccacctctga cttgagcgtc gatttttgtg atgctcgtca gggggggcgga gcctatggaa    8340 aaacgccagc aacgcggcct ttttacggtt cctggccttt tgctggcctt ttgctcacat    8400
gttctttcct gcgttatccc ctgattctgt ggataaccgt attaccgcct ttgagtgagc    8460
tgataccgct cgccgcagcc gaacgaccga gcgcagcgag tcagtgagcg aggaagcgga    8520
agagcgccca atacgcaaac cgcctctccc cgcgcgttgg ccgattcatt aatgcagctg    8580
tggaatgtgt gtcagttagg gtgtggaaag tccccaggct ccccagcagg cagaagtatg    8640
caaagcatgc atctcaatta gtcagcaacc aggtgtggaa agtccccagg ctccccagca    8700
ggcagaagta tgcaaagcat gcatctcaat tagtcagcaa ccatagtccc gcccctaact    8760
ccgcccatcc cgcccctaac tccgcccagt tccgcccatt ctccgcccca tggctgacta    8820 attttttttta tttatgcaga ggccgaggcc gcctcggcct ctgagctatt ccagaagtag    8880
tgaggaggct ttttttggagg cctaggcttt tgcaaaaagc ttggacacaa gacaggcttg    8940
cgagatatgt ttgagaatac cactttatcc cgcgtcaggg agaggcagtg cgtaaaagga    9000
cgcggactca tgtgaaatac tggtttttag tgcgccagat ctctataatc tcgcgcaacc    9060 tatttttcccc tcgaacactt tttaagccgt agataaacag gctgggacac ttcacatgag    9120
cgaaaaatac atcgtcacct gggacatgtt gcagatccat gcacgtaaac tcgcaagccg    9180
actgatgcct tctgaacaat ggaaaggcat tattgccgta agccgtggcg gtctggtacc    9240
gggtgcgtta ctggcgcgtg aactgggtat tcgtcatgtc gataccgttt gtatttccag    9300
ctacgatcac gacaaccagc gcgagcttaa agtgctgaaa cgcgcagaag gcgatggcga    9360
aggcttcatc gttattgatg acctggtgga taccggtggt actgcggttg cgattcgtga    9420
aatgtatcca aaagcgcact tgtcaccat cttcgcaaaa ccggctggtc gtccgctggt    9480
tgatgactat gttgttgata tcccgcaaga tacctggatt gaacagccgt gggatatggg    9540
cgtcgtattc gtcccgccaa tctccggtcg ctaatctttt caacgcctgg cactgccggg    9600
cgttgttctt tttaacttca ggcgggttac aatagtttcc agtaagtatt ctggaggctg    9660
catccatgac acaggcaaac ctgagcgaaa ccctgttcaa accccgcttt aaacatcctg    9720
```

```
aaacctcgac gctagtccgc cgctttaatc acggcgcaca accgcctgtg cagtcggccc    9780
ttgatggtaa aaccatccct cactggtatc gcatgattaa ccgtctgatg tggatctggc    9840
gcggcattga cccacgcgaa atcctcgacg tccaggcacg tattgtgatg agcgatgccg    9900
aacgtaccga cgatgattta tacgatacgg tgattggcta ccgtggcggc aactggattt    9960
atgagtgggc cccggatctt tgtgaaggaa ccttacttct gtggtgtgac ataattggac   10020
aaactaccta cagagattta aagctctaag gtaaatataa aattttttaag tgtataatgt   10080 gttaaactac tgattctaat tgtttgtgta ttttagattc aacctatgg aactgatgaa    10140 tgggagcagt ggtggaatgc ctttaatgag gaaaacctgt tttgctcaga agaaatgcca   10200
tctagtgatg atgaggctac tgctgactct caacattcta ctcctccaaa aagaagaga    10260 aaggtagaag accccaagga ctttccttca gaattgctaa gttttttgag tcatgctgtg   10320
tttagtaata gaactcttgc ttgctttgct atttacacca caaaggaaaa agctgcactg   10380
ctatacaaga aaattatgga aaatattct gtaacctta taagtaggca taacagttat      10440
aatcataaca tactgttttt tcttactcca cacaggcata gagtgtctgc tattaataac    10500
tatgctcaaa aattgtgtac ctttagcttt ttaatttgta aggggttaa taaggaatat     10560 ttgatgtata gtgccttgac tagagatcat aatcagccat accacatttg tagaggtttt    10620 acttgctta aaaaacctcc cacacctccc cctgaacctg aaacataaaa tgaatgcaat     10680
tgttgttgtt aacttgttta ttgcagctta taatggttac aaataaagca atagcatcac   10740
aaatttcaca ataaagcat ttttttcact gcattctagt tgtggtttgt ccaaactcat     10800
caatgtatct tatcatgtct ggatcaactg gataactcaa gctaaccaaa atcatcccaa   10860
acttcccacc ccatacccta ttaccactgc caattacctg tggtttcatt tactctaaac    10920
ctgtgattcc tctgaattat tttcatttta agaaattgt atttgttaaa tatgtactac     10980
aaacttagta gt                                                                    10992

<210> SEQ ID NO 50
<211> LENGTH: 13600
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
tggaagggct aattcactcc caagaagac aagatatcct tgatctgtgg atctaccaca        60
cacaaggcta cttccctgat tagcagaact acacaccagg gccagggtca gatatccact      120
gacctttgga tggtgctaca agctagtacc agttgagcca gataaggtag aagaggccaa      180
taaaggagag aacaccagct tgttacaccc tgtgagcctg catgggatgg atgacccgga      240
gagagaagtg ttagagtgga ggtttgacag ccgcctagca tttcatcacg tggcccgaga      300
gctgcatccg gagtacttca agaactgctg atatcgagct tgctacaagg acttttccgc      360
tggggacttt ccaggaggc gtggcctggg cgggactggg gagtggcgag ccctcagatc       420
ctgcatataa gcagctgctt tttgcctgta ctgggtctct ctggttagac cagatctgag      480
cctgggagct ctctggctaa ctagggaacc cactgcttaa gcctcaataa agcttgcctt      540
gagtgcttca agtagtgtgt gcccgtctgt tgtgtgactc tggtaactag agatccctca     600
gaccctttta gtcagtgtgg aaaatctcta gcttaattaa ccgtacgcgt actacgtata     660
aagccaggaa tggatggccc aaaagttaaa caatggccat tgacagaaga aaaaataaaa    720
```

```
gcattagtag aaatttgtac agagatggaa aaggaaggga aaatttcaaa aattgggcct      780
gaaaatccat acaatactcc agtatttgcc ataaagaaaa aagacagtac taaatggaga      840
aaattagtag atttcagaga acttaataag agaactcaag acttctggga agttcaatta      900
ggaataccac atcccgcagg gttaaaaaag aaaaaatcag taacagtact ggatgtgggt      960
gatgcatatt tttcagttcc cttagatgaa gacttcagga aatatactgc atttaccata     1020
cctagtataa acaatgagac accagggatt agatatcagt acaatgtgct tccacaggga     1080
tggaaaggat caccagcaat attccaaagt agcatgacaa aaatcttaga gccttttaga     1140
aaacaaaatc cagacatagt tatctatcaa tacatggatg atttgtatgt aggatctgac     1200
ttagaaatag ggcagcatag aacaaaaata gaggagctga gacaacatct gttgaggtgg     1260
ggacttacca caccagacaa aaaacatcag aaagaacctc cattcctttg gatgggttat     1320
gaactccatc ctgataaatg gacagtacag cctatagtgc tgccagaaaa agacagctgg     1380
actgtcaatg acatacagaa gttagtggga aaattgaatt gggcaagtca gatttaccca     1440
gggattaaag taaggcaatt atgtaaactc cttagaggaa ccaaagcact aacagaagta     1500
ataccactaa cagaagaagc agagctagaa ctggcagaaa acagagagat tctaaaagaa     1560
ccagtacatg gagtgtatta tgacccatca aaagacttaa tagcagaaat acagaagcag     1620
gggcaaggcc aatggacata tcaaatttat caagagccat ttaaaaatct gaaaacagga     1680
aaatatgcaa gaatgagggg tgcccacact aatgatgtaa aacaattaac agaggcagtg     1740
caaaaaataa ccacagaaag catagtaata tggggaaaga ctcctaaatt taaactgccc     1800
atacaaaagg aaacatggga acatggtgg acagagtatt ggcaagccac ctggattcct     1860
gagtgggagt ttgttaatac ccctcctta gtgaaattat ggtaccagtt agagaaagaa     1920
cccatagtag gagcagaaac cttctatgta gatggggcag ctaacaggga gactaaatta     1980
ggaaaagcag gatatgttac taatagagga agacaaaaag ttgtcaccct aactgacaca     2040
acaaatcaga agactgagtt acaagcaatt tatctagctt tgcaggattc gggattagaa     2100
gtaaacatag taacagactc acaatatgca ttaggaatca ttcaagcaca accagatcaa     2160
agtgaatcag agttagtcaa tcaaataata gagcagttaa taaaaaagga aaaggtctat     2220
ctggcatggg taccagcaca caaaggaatt ggaggaaatg aacaagtaga taaattagtc     2280
agtgctggaa tcaggaaagt actatttta gatggaatag ataaggccca agatgaacat     2340
gagaaatatc acagtaattg gagagcaatg gctagtgatt ttaacctgcc acctgtagta     2400
gcaaaagaaa tagtagccag ctgtgataaa tgtcagctaa aaggagaagc catgcatgga     2460
caagtagact gtagtccagg aatatggcaa ctagattgta cacatttaga aggaaaagtt     2520
atcctggtag cagttcatgt agccagtgga tatatagaag cagaagttat tccagcagaa     2580
acagggcagg aaacagcata ttttcttta aaattagcag gaagatggcc agtaaaaaca     2640
atacatacag acaatggcag caatttcacc agtgctacgg ttaaggccgc ctgttggtgg     2700
gcgggaatca agcaggaatt tggaattccc tacaatcccc aaagtcaagg agtagtagaa     2760
tctatgaata aagaattaaa gaaaattata ggacaggtaa gagatcaggc tgaacatctt     2820
aagacagcag tacaaatggc agtattcatc cacaatttta aaagaaaagg ggggattggg     2880
gggtacagtg caggggaaag aatagtagac ataatagcaa cagacataca aactaaagaa     2940
ttacaaaaac aaattacaaa aattcaaaat tttcgggttt attacaggga cagcagaaat     3000
ccactttgga aaggaccagc aaagctcctc tggaaaggtg aaggggcagt agtaatacaa     3060
gataatagtg acataaaagt agtgccaaga agaaaagcaa agatcattag ggattatgga     3120
```

```
aaacagatgg caggtgatga ttgtgtggca agtagacagg atgaggatta gaacatggaa    3180
aagtttagta aaacaccata tgtatgtttc agggaaagct aggggatggt tttatagaca    3240
tcactatgaa agccctcatc caagaataag ttcagaagta cacatcccac taggggatgc    3300
tagattggta ataacaacat attggggtct gcatacagga gaaagagact ggcatttggg    3360
tcagggagtc tccatagaat ggaggaaaaa gagatatagc acacaagtag accctgaact    3420
agcagaccaa ctaattcatc tgtattactt tgactgtttt tcagactctg ctataagaaa    3480
ggccttatta ggacacatag ttagccctag gtgtgaatat caagcaggac ataacaaggt    3540
aggatctcta caatacttgg cactagcagc attaataaca ccaaaaaaga taaagccacc    3600
tttgcctagt gttacgaaac tgacagagga tagatggaac aagccccaga agaccaaggg    3660
ccacagaggg agccacacaa tgaatggaca ctagagcttt tagaggagct taagaatgaa    3720
gctgttagac attttcctag gatttggctc catggcttag ggcaacatat ctatgaaact    3780 tatgggggata cttgggcagg agtggaagcc ataataagaa ttctgcaaca actgctgttt    3840
atccattttc agaattgggt gtcgacatag cagaataggc gttactcgac agaggagagc    3900
aagaaatgga gccagtagat cctagactag agccctggaa gcatccagga agtcagccta    3960
aaactgcttg taccaattgc tattgtaaaa agtgttgctt tcattgccaa gtttgtttca    4020
taacaaaagc cttaggcatc tcctatggca ggaagaagcg gagacagcga cgaagagctc    4080
atcagaacag tcagactcat caagcttctc tatcaaagca gtaagtagta catgtaacgc    4140
aacctatacc aatagtagca atagtagcat tagtagtagc aataataata gcaatagttg    4200
tgtggtccat agtaatcata gaatatagga aaatattaag acaaagaaaa atagacaggt    4260
taattgatag actaatagaa agagcagaag acagtggcaa tgagagtgaa ggagaaatat    4320
cagcacttgt ggagatgggg gtggagatgg ggcaccatgc tccttgggat gttgatgatc    4380
tgtagtgcta cagaaaaatt gtgggtcaca gtctattatg gggtacctgt gtggaaggaa    4440
gcaaccacca ctctattttg tgcatcagat gctaaagcat atgatacaga ggtacataat    4500
gtttgggcca cacatgcctg tgtacccaca gaccccaacc cacaagaagt agtattggta    4560
aatgtgacag aaaattttaa catgtggaaa aatgacatgg tagaacagat gcatgaggat    4620
ataatcagtt tatgggatca aagcctaaag ccatgtgtaa aattaacccc actctgtgtt    4680
agtttaaagt gcactgattt gaagaatgat actaatacca atagtagtag cgggagaatg    4740
ataatggaga aaggagagat aaaaaactgc tctttcaata tcagcacaag cataagaggt    4800
aaggtgcaga aagaatatgc attttttat aaacttgata taataccaat agataatgat    4860
actaccagct ataagttgac aagttgtaac acctcagtca ttacacaggc ctgtccaaag    4920
gtatcctttg agccaattcc catacattat tgtgccccgg ctggttttgc gattctaaaa    4980
tgtaataata agacgttcaa tggaacagga ccatgtacaa atgtcagcac agtacaatgt    5040
acacatggaa ttaggccagt agtatcaact caactgctgt taaatggcag tctagcagaa    5100
gaagaggtag taattagatc tgtcaatttc acggacaatg ctaaaaccat aatagtacag    5160
ctgaacacat ctgtagaaat taattgtaca agacccaaca acaatacaag aaaaagaatc    5220
cgtatccaga gaggaccagg gagagcattt gttacaatag gaaaaatagg aaatatgaga    5280
caagcacatt gtaacattag tagagcaaaa tggaataaca ctttaaaaca gatagctagc    5340
aaattaagag aacaatttgg aaataataaa acaataatct ttaagcaatc ctcaggaggg    5400
gacccagaaa ttgtaacgca cagttttaat tgtggagggg aatttttcta ctgtaattca    5460
```

```
acacaactgt ttaatagtac ttggtttaat agtacttgga gtactgaagg gtcaaataac   5520
actgaaggaa gtgacacaat caccctccca tgcagaataa aacaaattat aaacatgtgg   5580
cagaaagtag gaaaagcaat gtatgcccct cccatcagtg gacaaattag atgttcatca   5640
aatattacag ggctgctatt aacaagagat ggtggtaata gcaacaatga gtccgagatc   5700
ttcagacctg gaggaggaga tatgagggac aattggagaa gtgaattata taaatataaa   5760
gtagtaaaaa ttgaaccatt aggagtagca cccaccaagg caaagagaag agtggtgcag   5820
agagaaaaaa gagcagtggg aataggagct ttgttccttg ggttcttggg agcagcagga   5880
agcactatgg gcgcagcgtc aatgacgctg acggtacagg ccagacaatt attgtctggt   5940
atagtgcagc agcagaacaa tttgctgagg gctattgagg cgcaacagca tctgttgcaa   6000
ctcacagtct ggggcatcaa gcagctccag gcaagaatcc tggctgtgga agataccta    6060
aaggatcaac agctcctggg gatttggggt tgctctggaa aactcatttg caccactgct   6120
gtgccttgga atgctagttg gagtaataaa tctctggaac agatttggaa tcacacgacc   6180
tggatggagt gggacagaga aattaacaat tacacaagct taatacactc cttaattgaa   6240
gaatcgcaaa accagcaaga aaagaatgaa caagaattat tggaattaga taatgggca    6300
agtttgtgga attggtttaa cataacaaat tggctgtggt atataaaatt attcataatg   6360
atagtaggag gcttggtagg tttaagaata gttttgctg tactttctat agtgaataga    6420
gttaggcagg gatattcacc attatcgttt cagacccacc tcccaacccc gaggggaccc   6480
gacaggcccg aaggaataga agaagaaggt ggagagagag acagagacag atccattcga   6540
ttagtgaacg gatccttagc acttatctgg gacgatctgc ggagcctgtg cctcttcagc   6600
taccaccgct tgagagactt actcttgatt gtaacgagga ttgtggaact tctgggacgc   6660
agggggtggg aagccctcaa atattggtgg aatctcctac aatattggag tcaggagcta   6720
aagaatagtg ctgttagctt gctcaatgcc acagccatag cagtagctga ggggacagat   6780
agggttatag aagtagtaca aggagcttgt agagctattc gccacatacc tagaagaata   6840
agacagggct tggaaaggat tttgctataa gatgggtggc gcggccgcaa tggtgagcaa   6900
gggcgaggag ctgttcaccg gggtggtgcc catcctggtc gagctggacg gcgacgtaaa   6960
cggccacaag ttcagcgtgt ccggcgaggg cgagggcgat gccacctacg gcaagctgac   7020
cctgaagttc atctgcacca ccggcaagct gcccgtgccc tggcccaccc tcgtgaccac   7080
cctgacctac ggcgtgcagt gcttcagccg ctaccccgac cacatgaagc agcacgactt   7140
cttcaagtcc gccatgcccg aaggctacgt ccaggagcgc accatcttct tcaaggacga   7200
cggcaactac aagacccgcg ccgaggtgaa gttcgagggc gacaccctgg tgaaccgcat   7260
cgagctgaag ggcatcgact tcaaggagga cggcaacatc ctggggcaca agctggagta   7320
caactacaac agccacaacg tctatatcat ggccgacaag cagaagaacg gcatcaaggc   7380
gaacttcaag atccgccaca acatcgagga cggcagcgtg cagctcgccg accactacca   7440
gcagaacacc cccatcggcg acggccccgt gctgctgccc gacaaccact acctgagcac   7500
ccagtccgcc ctgagcaaag accccaacga gaagcgcgat cacatggtcc tgctggagtt   7560
cgtgaccgcc gccgggatca ctctcggcat ggacgagctg tacaagtaag aattctgact   7620
cgagacctag aaaaacatgg agcaatcaca gtagcaata cagcagctac caatgctgat    7680
tgtgcctggc tagaagcaca agaggaggag gaggtggggtt ttccagtcac acctcaggta   7740
cctttaagac caatgactta caaggcagct gtagatctta gccactttt aaaagaaaag    7800
gggggactgg aagggctaat tcactcccaa cgaagacaag atatccttga tctgtggatc   7860
```

```
taccacacac aaggctactt ccctgattgg cagaactaca caccagggcc agggatcaga    7920
tatccactga cctttggatg gtgctacaag ctagtaccag ttgagcaaga gaaggtagaa    7980
gaagccaatg aaggagagaa cacccgcttg ttacaccctg tgagcctgca tgggatggat    8040
gacccggaga gagaagtatt agagtggagg tttgacagcc gcctagcatt tcatcacatg    8100
gcccgagagc tgcatccgga gtacttcaag aactgctgac atcgagcttg ctacaaggga    8160
ctttccgctg gggactttcc agggaggcgt ggcctgggcg ggactgggga gtggcgagcc    8220
ctcagatgct gcatataagc agctgctttt tgcttgtact gggtctctct ggttagacca    8280
gatctgagcc tgggagctct ctggctaact agggaaccca ctgcttaagc ctcaataaag    8340
cttgccttga gtgcttcaag tagtgtgtgc ccgtctgttg tgtgactctg gcgcgcctct    8400
agaattaatt ccgtgtattc tatagtgtca cctaaatcgt atgtgtatga tacataaggt    8460
tatgtattaa ttgtagccgc gttctaacga caatatgtac aagcctaatt gtgtagcatc    8520
tggcttactg aagcagaccc tatcatctct ctcgtaaact gccgtcagag tcggtttggt    8580
tggacgaacc ttctgagttt ctggtaacgc cgtcccgcac ccggaaatgg tcagcgaacc    8640
aatcagcagg gtcatcgcta gccagatcct ctacgccgga cgcatcgtgg ccggcatcac    8700
cggcgccaca ggtgcggttg ctggcgccta tatcgccgac atcaccgatg gggaagatcg    8760
ggctcgccac ttcgggctca tgagcgcttg tttcggcgtg gtatggtgg caggccccgt    8820 ggccggggga ctgttgggcg ccatctcctt gcatgcacca ttccttgcgg cggcggtgct    8880
caacggcctc aacctactac tgggctgctt cctaatgcag gagtcgcata agggagagcg    8940
tcgaatggtg cactctcagt acaatctgct ctgatgccgc atagttaagc cagccccgac    9000
acccgccaac acccgctgac gcgccctgac gggcttgtct gctcccggca tccgcttaca    9060
gacaagctgt gaccgtctcc gggagctgca tgtgtcagag gttttcaccg tcatcaccga    9120
aacgcgcgag acgaaagggc ctcgtgatac gcctattttt ataggttaat gtcatgataa    9180
taatggtttc ttagacgtca ggtggcactt ttcggggaaa tgtgcgcgga accctatt    9240 gtttattttt ctaaatacat tcaaatatgt atccgctcat gagacaataa ccctgataaa    9300
tgcttcaata atattgaaaa aggaagagta tgagtattca catttccgt gtcgccctta    9360 ttccctttt tgcggcattt tgccttcctg ttttgctca cccagaaacg ctggtgaaag    9420
taaaagatgc tgaagatcag ttgggtgcac gagtgggtta catcgaactg gatctcaaca    9480
gcggtaagat ccttgagagt tttcgccccg aagaacgttt tccaatgatg agcactttta    9540
aagttctgct atgtggcgcg gtattatccc gtattgacgc cgggcaagag caactcggtc    9600
gccgcataca ctattctcag aatgacttgg ttgagtactc accagtcaca gaaaagcatc    9660
ttacggatgg catgacagta agagaattat gcagtgctgc cataaccatg agtgataaca    9720
ctgcggccaa cttacttctg acaacgatcg gaggaccgaa ggagctaacc gcttttttgc    9780
acaacatggg ggatcatgta actcgccttg atcgttggga accggagctg aatgaagcca    9840
taccaaacga cgagcgtgac accacgatgc ctgtagcaat ggcaacaacg ttgcgcaaac    9900
tattaactgg cgaactactt actctagctt cccggcaaca attaatagac tggatggagg    9960
cggataaagt tgcaggacca cttctgcgct cggcccttcc ggctggctgg tttattgctg    10020
ataaatctgg agccggtgag cgtgggtctc gcggtatcat tgcagcactg gggccagatg    10080
gtaagccctc ccgtatcgta gttatctaca cgacggggag tcaggcaact atggatgaac    10140
gaaatagaca gatcgctgag ataggtgcct cactgattaa gcattggtaa ctgtcagacc    10200
```

```
aagtttactc atatatactt tagattgatt taaaacttca ttttaatttt aaaggatct   10260 aggtgaagat ccttttttgat aatctcatga ccaaaatccc ttaacgtgag ttttcgttcc  10320
actgagcgtc agacccgta gaaaagatca aaggatcttc ttgagatcct ttttttctgc   10380
gcgtaatctg ctgcttgcaa acaaaaaaac caccgctacc agcggtggtt tgtttgccgg   10440
atcaagagct accaactctt tttccgaagg taactggctt cagcagagcg cagataccaa   10500
atactgttct tctagtgtag ccgtagttag gccaccactt caagaactct gtagcaccgc   10560
ctacatacct cgctctgcta atcctgttac cagtggctgc tgccagtggc gataagtcgt   10620
gtcttaccgg gttggactca agacgatagt taccggataa ggcgcagcgg tcgggctgaa   10680
cggggggttc gtgcacacag cccagcttgg agcgaacgac ctacaccgaa ctgagatacc   10740
tacagcgtga gctatgagaa agcgccacgc ttcccgaagg gagaaaggcg gacaggtatc   10800
cggtaagcgg cagggtcgga acaggagagc gcacgaggga gcttccaggg ggaaacgcct   10860
ggtatcttta tagtcctgtc gggtttcgcc acctctgact tgagcgtcga ttttgtgat    10920 gctcgtcagg ggggcggagc ctatggaaaa acgccagcaa cgcggccttt ttacggttcc   10980
tggccttttg ctggccttt gctcacatgt tctttcctgc gttatcccct gattctgtgg    11040
ataaccgtat taccgccttt gagtgagctg ataccgctcg ccgcagccga acgaccgagc   11100
gcagcgagtc agtgagcgag gaagcggaag agcgcccaat acgcaaaccg cctctccccg   11160
cgcgttggcc gattcattaa tgcagctgtg gaatgtgtgt cagttagggt gtggaaagtc   11220
cccaggctcc ccagcaggca gaagtatgca aagcatgcat ctcaattagt cagcaaccag   11280
gtgtggaaag tccccaggct ccccagcagg cagaagtatg caaagcatgc atctcaatta   11340
gtcagcaacc atagtcccgc ccctaactcc gcccatcccg ccctaactc cgcccagttc    11400 cgcccattct ccgcccatg gctgactaat tttttttatt tatgcagagg ccgaggccgc    11460
ctcggcctct gagctattcc agaagtagtg aggaggcttt tttggaggcc taggcttttg   11520
caaaaagctt ggacacaaga caggcttgcg agatatgttt gagaatacca ctttatcccg   11580
cgtcagggag aggcagtgcg taaaagacg cggactcatg tgaaatactg gtttttagtg    11640
cgccagatct ctataatctc gcgcaaccta ttttccctc gaacactttt taagccgtag   11700
ataaacaggc tgggacactt cacatgagcg aaaaatacat cgtcacctgg gacatgttgc   11760
agatccatgc acgtaaactc gcaagccgac tgatgccttc tgaacaatgg aaaggcatta   11820
ttgccgtaag ccgtggcggt ctggtaccgg gtgcgttact ggcgcgtgaa ctgggtattc   11880
gtcatgtcga taccgtttgt atttccagct acgatcacga caaccagcgc gagcttaaag   11940
tgctgaaacg cgcagaaggc gatggcgaag cttcatcgt tattgatgac ctggtggata    12000
ccggtggtac tgcggttgcg attcgtgaaa tgtatccaaa agcgcacttt gtcaccatct   12060
tcgcaaaacc ggctggtcgt ccgctggttg atgactatgt tgttgatatc ccgcaagata   12120
cctggattga acagcgtgg gatatggcg tcgtattcgt cccgccaatc tccggtcgct     12180
aatcttttca cgcctggca ctgccggcg ttgttctttt taacttcagg cgggttacaa     12240
tagtttccag taagtattct ggaggctgca tccatgacac aggcaaacct gagcgaaacc   12300
ctgttcaaac cccgctttaa acatcctgaa acctcgacgc tagtccgccg ctttaatcac   12360
ggcgcacaac cgcctgtgca gtcggccctt gatggtaaaa ccatccctca ctggtatcgc   12420
atgattaacc gtctgatgtg gatctggcgc ggcattgacc cacgcgaaat cctcgacgtc   12480
caggcacgta ttgtgatgag cgatgccgaa cgtaccgacg atgatttata cgatacggtg   12540
attggctacc gtggcggcaa ctggattat gagtgggccc cggatctttg tgaaggaacc   12600
```

```
ttacttctgt ggtgtgacat aattggacaa actacctaca gagatttaaa gctctaaggt    12660
aaatataaaa tttttaagtg tataatgtgt taaactactg attctaattg tttgtgtatt    12720
ttagattcca acctatggaa ctgatgaatg ggagcagtgg tggaatgcct taatgagga     12780 aaacctgttt tgctcagaag aaatgccatc tagtgatgat gaggctactg ctgactctca    12840
acattctact cctccaaaaa agaagagaaa ggtagaagac cccaaggact ttccttcaga    12900
attgctaagt ttttgagtc atgctgtgtt tagtaataga actcttgctt gctttgctat     12960
ttacaccaca aaggaaaaag ctgcactgct atacaagaaa attatggaaa atattctgt     13020 aacctttata agtaggcata acagttataa tcataacata ctgttttttc ttactccaca    13080
caggcataga gtgtctgcta ttaataacta tgctcaaaaa ttgtgtacct ttagcttttt    13140
aatttgtaaa ggggttaata aggaatattt gatgtatagt gccttgacta gagatcataa    13200
tcagccatac cacatttgta gaggttttac ttgctttaaa aaacctccca cacctccccc    13260
tgaacctgaa acataaaatg aatgcaattg ttgttgttaa cttgtttatt gcagcttata    13320
atggttacaa ataaagcaat agcatcacaa atttcacaaa taaagcattt ttttcactgc    13380
attctagttg tggtttgtcc aaactcatca atgtatctta tcatgtctgg atcaactgga    13440
taactcaagc taaccaaaat catcccaaac ttcccacccc atccctatt accactgcca     13500 attacctgtg gtttcattta ctctaaacct gtgattcctc tgaattattt tcattttaaa    13560
gaaattgtat ttgttaaata tgtactacaa acttagtagt                          13600
```

<210> SEQ ID NO 51
<211> LENGTH: 12682
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51

```
tggaagggct aattcactcc caagaagac aagatatcct tgatctgtgg atctaccaca      60
cacaaggcta cttccctgat tagcagaact acacaccagg gccagggtca gatatccact    120
gacctttgga tggtgctaca agctagtacc agttgagcca gataaggtag aagaggccaa    180
taaaggagag aacaccagct tgttacaccc tgtgagcctg catgggatgg atgacccgga    240
gagagaagtg ttagagtgga ggtttgacag ccgcctagca tttcatcacg tggcccgaga    300
gctgcatccg gagtacttca agaactgctg atatcgagct tgctacaagg actttccgc     360 tggggacttt ccaggagc gtggcctggg cgggactggg gagtggcgag ccctcagatc      420
ctgcatataa gcagctgctt tttgcctgta ctgggtctct ctggttagac cagatctgag    480
cctgggagct ctctggctaa ctagggaacc cactgcttaa gcctcaataa agcttgcctt    540
gagtgcttca agtagtgtgt gcccgtctgt tgtgtgactc tggtaactag agatccctca    600 gacccttta gtcagtgtgg aaaatctcta gcagtggcgc ccgaacaggg acttgaaagc     660
gaaagggaaa ccagaggagc tctctcgacg caggactcgg cttgctgaag cgcgcacggc    720
aagaggcgag gggcggcgac tggtgagtac gccaaaaatt tgactagcg gaggctagaa     780 ggagagagat gggtgcgaga gcgtcagtat taagcggggg agaattagat cgatgggaaa    840
aaattcggtt aaggccaggg ggaaagaaaa aatataaatt aaaacatata gtatgggcaa    900
gcagggagct agaacgattc gcagttaatc ctggcctgtt agaaacatca gaaggctgta    960
gacaaatact gggacagcta caaccatccc ttcagacagg atcagaagaa cttagatcat    1020
```

```
tatataatac agtagcaacc ctctattgtg tgcatcaaag gatagagata aaagacacca      1080
aggaagcttt agacaagata gaggaagagc aaaacaaaag taagaaaaaa gcacagcaag      1140
cagcagctga cacaggacac agcaatcagg tcagccaaaa ttaccctata gtgcagaaca      1200
tccaggggca aatggtacat caggccatat cacctgaaac tttaaatgca tgggtaaaag      1260
tagtagaaga gaaggctttc agcccagaag tgatacccat gttttcagca ttatcagaag      1320
gagccacccc acaagattta aacaccatgc taaacacagt gggggacat  caagcagcca      1380 tgcaaatgtt aaaagagacc atcaatgagg aagctgcaga atgggataga gtgcatccag      1440
tgcatgcagg gcctattgca ccaggccaga tgagagaacc aaggggaagt gacatagcag      1500
gaactactag tacccttcag gaacaaatag gatggatgac aaataatcca cctatcccag      1560
taggagaaat ttataaaaga tggataatcc tgggattaaa taaaatagta agaatgtata      1620
gccctaccag cattctggac ataagacaag gaccaaaaga acccttttaga gactatgtag      1680 accggttcta taaaactcta agagccgagc aagcttcaca ggaggtaaaa aattggatga      1740
cagaaacctt gttggtccaa aatgcgaacc cagattgtaa gactatttta aaagcattgg      1800
gaccagcggc tacactagaa gaaatgatga cagcatgtca gggagtagga ggacccggcc      1860
ataaggcaag agttttggct gaagcaatga gccaagtaac aaattcagct accataatga      1920
tgcagagagg caattttagg aaccaaagaa agattgttaa gtgtttcaat tgtggcaaag      1980
aagggcacac agccagaaat tgcagggccc ctaggaaaaa gggctgttgg aaatgtggaa      2040
aggaaggaca ccaaatgaaa gattgtactg agagacaggc taattttttta gggaagatct      2100 ggccttccta caagggaagg ccagggaatt ttcttcagag cagaccagag ccaacagccc      2160
caccagaaga gagcttcagg tctggggtag agacaacaac tccccctcag aagcaggagc      2220
cgatagacaa ggaactgtat cctttaactt ccctcagatc actctttggc aacgacccct      2280
cgtcacaata aagatagggg ggcaactaaa ggaagctcta ttagatacat taattaaccg      2340
tacgcgtact acgtaagaag tacacatccc actaggggat gctagattgg taataacaac      2400
atattggggt ctgcatacag gagaaagaga ctggcatttg ggtcagggag tctccataga      2460
atggaggaaa aagagatata gcacacaagt agaccctgaa ctagcagacc aactaattca      2520
tctgtattac tttgactgtt tttcagactc tgctataaga aaggccttat taggacacat      2580
agttagccct aggtgtgaat atcaagcagg acataacaag gtaggatctc tacaatactt      2640
ggcactagca gcattaataa caccaaaaaa gataaagcca ccctttgcct agtgttacgaa      2700 actgacagag gatagatgga acaagcccca gaagaccaag ggccacagag ggagccacac      2760
aatgaatgga cactagagct tttagaggag cttaagaatg aagctgttag acattttcct      2820
aggatttggc tccatggctt agggcaacat atctatgaaa cttatgggga tacttgggca      2880
ggagtggaag ccataataag aattctgcaa caactgctgt ttatccattt tcagaattgg      2940
gtgtcgacat agcagaatag gcgttactcg acagaggaga gcaagaaatg gagccagtag      3000
atcctagact agagccctgg aagcatccag gaagtcagcc taaaactgct tgtaccaatt      3060
gctattgtaa aaagtgttgc tttcattgcc aagtttgttt cataacaaaa gccttaggca      3120
tctcctatgg caggaagaag cggagacagc gacgaagagc tcatcagaac agtcagactc      3180
atcaagcttc tctatcaaag cagtaagtag tacatgtaac gcaacctata ccaatagtag      3240
caatagtagc attagtagta gcaataataa tagcaatagt tgtgtggtcc atagtaatca      3300
tagaatatag gaaaatatta agacaaagaa aaatagacag gttaattgat agactaatag      3360
```

```
aaagagcaga agacagtggc aatgagagtg aaggagaaat atcagcactt gtggagatgg      3420
gggtggagat ggggcaccat gctccttggg atgttgatga tctgtagtgc tacagaaaaa      3480
ttgtgggtca cagtctatta tggggtacct gtgtggaagg aagcaaccac cactctattt      3540
tgtgcatcag atgctaaagc atatgataca gaggtacata atgtttgggc cacacatgcc      3600
tgtgtaccca cagaccccaa cccacaagaa gtagtattgg taaatgtgac agaaaatttt      3660
aacatgtgga aaaatgacat ggtagaacag atgcatgagg atataatcag tttatgggat      3720
caaagcctaa agccatgtgt aaaattaacc ccactctgtg ttagtttaaa gtgcactgat      3780
ttgaagaatg atactaatac caatagtagt agcgggagaa tgataatgga gaaaggagag      3840
ataaaaaact gctcttttca tatcagcaca agcataagag gtaaggtgca gaaagaatat      3900
gcattttttt ataaacttga tataatacca atagataatg atactaccag ctataagttg      3960
acaagttgta acacctcagt cattacacag gcctgtccaa aggtatcctt tgagccaatt      4020
cccatacatt attgtgcccc ggctggtttt gcgattctaa aatgtaataa taagacgttc      4080
aatggaacag gaccatgtac aaatgtcagc acagtacaat gtacacatgg aattaggcca      4140
gtagtatcaa ctcaactgct gttaaatggc agtctagcag aagaagaggt agtaattaga      4200
tctgtcaatt tcacggacaa tgctaaaacc ataatagtac agctgaacac atctgtagaa      4260
attaattgta caagacccaa caacaataca agaaaaagaa tccgtatcca gagaggacca      4320
gggagagcat ttgttacaat aggaaaaata ggaaatatga caagcaca ttgtaacatt      4380 agtagagcaa aatggaataa cactttaaaa cagatagcta gcaaattaag agaacaattt      4440
ggaaataata aaacaataat ctttaagcaa tcctcaggag gggacccaga aattgtaacg      4500
cacagtttta attgtggagg ggaattttc tactgtaatt caacacaact gtttaatagt      4560
acttggttta atagtacttg gagtactgaa gggtcaaata cactgaagg aagtgacaca      4620 atcaccctcc catgcagaat aaaacaaatt ataaacatgt ggcagaaagt aggaaaagca      4680
atgtatgccc ctcccatcag tggacaaatt agatgttcat caaatattac agggctgcta      4740
ttaacaagag atggtggtaa tagcaacaat gagtccgaga tcttcagacc tggaggagga      4800
gatatgaggg acaattggag aagtgaatta tataaatata agtagtaaa aattgaacca      4860 ttaggagtag cacccaccaa ggcaaagaga agagtggtgc agagagaaaa aagagcagtg      4920
ggaataggag ctttgttcct tgggttcttg ggagcagcag gaagcactat gggcgcagcg      4980
tcaatgacgc tgacggtaca ggccagacaa ttattgtctg gtatagtgca gcagcagaac      5040
aatttgctga gggctattga ggcgcaacag catctgttgc aactcacagt ctggggcatc      5100
aagcagctcc aggcaagaat cctggctgtg gaaagatacc taaaggatca acagctcctg      5160
gggatttggg gttgctctgg aaaactcatt tgcaccactg ctgtgccttg gaatgctagt      5220
tggagtaata aatctctgga acagatttgg aatcacacga cctggatgga gtgggacaga      5280
gaaattaaca attacacaag cttaatacac tccttaattg aagaatcgca aaaccagcaa      5340
gaaaagaatg aacaagaatt attggaatta gataaatggg caagtttgtg gaattggttt      5400
aacataacaa attggctgtg gtatataaaa ttattcataa tgatagtagg aggcttggta      5460
ggtttaagaa tagttttgc tgtactttct atagtgaata gagttaggca gggatattca      5520
ccattatcgt ttcagaccca cctcccaacc ccgagggac ccgacaggcc cgaaggaata      5580
gaagaagaag gtggagagag agacagagac agatccattc gattagtgaa cggatcctta      5640
gcacttatct gggacgatct gcggagcctg tgcctcttca gctaccaccg cttgagagac      5700
ttactcttga ttgtaacgag gattgtggaa cttctgggac gcagggggtg gaagccctc      5760
```

```
aaatattggt ggaatctcct acaatattgg agtcaggagc taaagaatag tgctgttagc   5820
ttgctcaatg ccacagccat agcagtagct gaggggacag atagggttat agaagtagta   5880
caaggagctt gtagagctat tcgccacata cctagaagaa taagacaggg cttggaaagg   5940
attttgctat aagatgggtg gcgcggccgc aatggtgagc aagggcgagg agctgttcac   6000
cggggtggtg cccatcctgg tcgagctgga cggcgacgta aacggccaca agttcagcgt   6060
gtccggcgag ggcgagggcg atgccaccta cggcaagctg accctgaagt tcatctgcac   6120
caccggcaag ctgcccgtgc cctggcccac cctcgtgacc accctgacct acggcgtgca   6180
gtgcttcagc cgctaccccg accacatgaa gcagcacgac ttcttcaagt ccgccatgcc   6240
cgaaggctac gtccaggagc gcaccatctt cttcaaggac gacggcaact acaagacccg   6300
cgccgaggtg aagttcgagg gcgacaccct ggtgaaccgc atcgagctga agggcatcga   6360
cttcaaggag gacggcaaca tcctggggca caagctggag tacaactaca acagccacaa   6420
cgtctatatc atggccgaca gcagaagaa cggcatcaag gcgaacttca agatccgcca   6480
caacatcgag gacggcagcg tgcagctcgc cgaccactac cagcagaaca cccccatcgg   6540
cgacggcccc gtgctgctgc ccgacaacca ctacctgagc acccagtccg ccctgagcaa   6600
agaccccaac gagaagcgcg atcacatggt cctgctggag ttcgtgaccg ccgccgggat   6660
cactctcggc atggacgagc tgtacaagta agaattctga ctcgagacct agaaaaacat   6720
ggagcaatca caagtagcaa tacagcagct accaatgctg attgtgcctg gctagaagca   6780
caagaggagg aggaggtggg ttttccagtc acacctcagg tacctttaag accaatgact   6840
tacaaggcag ctgtagatct tagccacttt ttaaaagaaa agggggact ggaagggcta   6900 attcactccc aacgaagaca agatatcctt gatctgtgga tctaccacac acaaggctac   6960
ttccctgatt ggcagaacta cacaccaggg ccagggatca gatatccact gacctttgga   7020
tggtgctaca agctagtacc agttgagcaa gagaaggtag aagaagccaa tgaaggagag   7080
aacacccgct tgttacaccc tgtgagcctg catgggatgg atgacccgga gagagaagta   7140
ttagagtgga ggtttgacag ccgcctagca tttcatcaca tggcccgaga gctgcatccg   7200
gagtacttca agaactgctg acatcgagct tgctacaagg actttccgc tggggacttt   7260 ccagggaggc gtggcctggg cgggactggg gagtggcgag ccctcagatg ctgcatataa   7320
gcagctgctt tttgcttgta ctgggtctct ctggttagac cagatctgag cctgggagct   7380
ctctggctaa ctagggaacc cactgcttaa gcctcaataa agcttgcctt gagtgcttca   7440
agtagtgtgt gcccgtctgt tgtgtgactc tggcgcgcct ctagaattaa ttccgtgtat   7500
tctatagtgt cacctaaatc gtatgtgtat gatacataag gttatgtatt aattgtagcc   7560
gcgttctaac gacaatatgt acaagcctaa ttgtgtagca tctggcttac tgaagcagac   7620
cctatcatct ctctcgtaaa ctgccgtcag agtcggtttg gttggacgaa ccttctgagt   7680
ttctggtaac gccgtcccgc acccggaaat ggtcagcgaa ccaatcagca gggtcatcgc   7740
tagccagatc ctctacgccg gacgcatcgt ggccggcatc accggcgcca caggtgcggt   7800
tgctggcgcc tatatcgccg acatcaccga tggggaagat cgggctcgcc acttcgggct   7860
catgagcgct tgtttcggcg tgggtatggt ggcaggcccc gtggccgggg gactgttggg   7920
cgccatctcc ttgcatgcac cattccttgc ggcggcggtg ctcaacggcc tcaacctact   7980
actgggctgc ttcctaatgc aggagtcgca taagggagag cgtcgaatgg tgcactctca   8040
gtacaatctg ctctgatgcc gcatagttaa gccagccccg acaccgcca acaccgctg    8100
```

```
acgcgccctg acgggcttgt ctgctcccgg catccgctta cagacaagct gtgaccgtct    8160 ccggagctg  catgtgtcag aggttttcac cgtcatcacc gaaacgcgcg agacgaaagg    8220
gcctcgtgat acgcctattt ttataggtta atgtcatgat aataatggtt tcttagacgt    8280
caggtggcac ttttcgggga aatgtgcgcg gaacccctat ttgtttattt ttctaaatac    8340
attcaaatat gtatccgctc atgagacaat aaccctgata aatgcttcaa taatattgaa    8400
aaaggaagag tatgagtatt caacatttcc gtgtcgccct tattccctt ttttgcggcat    8460 tttgccttcc tgttttttgct cacccagaaa cgctggtgaa agtaaaagat gctgaagatc    8520
agttgggtgc acgagtgggt tacatcgaac tggatctcaa cagcggtaag atccttgaga    8580
gttttcgccc cgaagaacgt tttccaatga tgagcacttt taaagttctg ctatgtggcg    8640
cggtattatc ccgtattgac gccgggcaag agcaactcgg tcgccgcata cactattctc    8700
agaatgactt ggttgagtac tcaccagtca cagaaaagca tcttacggat ggcatgacag    8760
taagagaatt atgcagtgct gccataacca tgagtgataa cactgcgcc  aacttacttc    8820 tgacaacgat cggaggaccg aaggagctaa ccgcttttt  gcacaacatg ggggatcatg    8880
taactcgcct tgatcgttgg gaaccggagc tgaatgaagc cataccaaac gacgagcgtg    8940
acaccacgat gcctgtagca atggcaacaa cgttgcgcaa actattaact ggcgaactac    9000
ttactctagc ttcccggcaa caattaatag actggatgga ggcggataaa gttgcaggac    9060
cacttctgcg ctcggccctt ccggctggct ggtttattgc tgataaatct ggagccggtg    9120
agcgtgggtc tcgcggtatc attgcagcac tggggccaga tggtaagccc tcccgtatcg    9180
tagttatcta cacgacgggg agtcaggcaa ctatggatga acgaaataga cagatcgctg    9240
agataggtgc ctcactgatt aagcattggt aactgtcaga ccaagtttac tcatatatac    9300
tttagattga tttaaaactt cattttaat ttaaaaggat ctaggtgaag atccttttg     9360 ataatctcat gaccaaaatc ccttaacgtg agttttcgtt ccactgagcg tcagaccccg    9420
tagaaaagat caaaggatct tcttgagatc cttttttct  gcgcgtaatc tgctgcttgc    9480
aaacaaaaaa accaccgcta ccagcggtgg tttgtttgcc ggatcaagag ctaccaactc    9540
tttttccgaa ggtaactggc ttcagcagag cgcagatacc aaatactgtt cttctagtgt    9600
agccgtagtt aggccaccac ttcaagaact ctgtagcacc gcctacatac ctcgctctgc    9660
taatcctgtt accagtggct gctgccagtg gcgataagtc gtgtcttacc gggttggact    9720
caagacgata gttaccggat aaggcgcagc ggtcgggctg aacggggggt tcgtgcacac    9780
agcccagctt ggagcgaacg acctacaccg aactgagata cctacagcgt gagctatgag    9840
aaagcgccac gcttcccgaa gggagaaagg cggacaggta tccggtaagc ggcagggtcg    9900
gaacaggaga gcgcacgagg gagcttccag ggggaaacgc ctggtatctt tatagtcctg    9960
tcgggtttcg ccacctctga cttgagcgtc gatttttgtg atgctcgtca ggggggcgga   10020
gcctatggaa aaacgccagc aacgcggcct ttttacggtt cctggccttt tgctggcctt   10080
ttgctcacat gttctttcct gcgttatccc ctgattctgt ggataaccgt attaccgcct   10140
ttgagtgagc tgataccgct cgccgcagcc gaacgaccga gcgcagcgag tcagtgagcg   10200
aggaagcgga agagcgccca atacgcaaac cgcctctccc cgcgcgttgg ccgattcatt   10260
aatgcagctg tggaatgtgt gtcagttagg gtgtggaaag tccccaggct ccccagcagg   10320
cagaagtatg caaagcatgc atctcaatta gtcagcaacc aggtgtggaa agtcccagg    10380 ctcccccagca ggcagaagta tgcaaagcat gcatctcaat tagtcagcaa ccatagtccc   10440
gcccctaact ccgcccatcc cgcccctaac tccgcccagt tccgcccatt ctccgcccca   10500
```

```
tggctgacta attttttta tttatgcaga ggccgaggcc gcctcggcct ctgagctatt    10560
ccagaagtag tgaggaggct tttttggagg cctaggcttt tgcaaaaagc ttggacacaa    10620
gacaggcttg cgagatatgt ttgagaatac cactttatcc cgcgtcaggg agaggcagtg    10680 cgtaaaaga cgcggactca tgtgaaatac tggtttttag tgcgccagat ctctataatc    10740
tcgcgcaacc tattttcccc tcgaacactt tttaagccgt agataaacag gctgggacac    10800
ttcacatgag cgaaaaatac atcgtcacct gggacatgtt gcagatccat gcacgtaaac    10860
tcgcaagccg actgatgcct tctgaacaat ggaaaggcat tattgccgta agccgtggcg    10920
gtctggtacc gggtgcgtta ctggcgcgtg aactgggtat tcgtcatgtc gataccgttt    10980
gtatttccag ctacgatcac gacaaccagc gcgagcttaa agtgctgaaa cgcgcagaag    11040
gcgatggcga aggcttcatc gttattgatg acctggtgga taccggtggt actgcggttg    11100
cgattcgtga aatgtatcca aaagcgcact tgtcaccat cttcgcaaaa ccggctggtc    11160
gtccgctggt tgatgactat gttgttgata tcccgcaaga tacctggatt gaacagccgt    11220
gggatatggg cgtcgtattc gtcccgccaa tctccggtcg ctaatctttt caacgcctgg    11280
cactgccggg cgttgttctt tttaacttca ggcgggttac aatagtttcc agtaagtatt    11340
ctggaggctg catccatgac acaggcaaac ctgagcgaaa ccctgttcaa accccgcttt    11400
aaacatcctg aaacctcgac gctagtccgc cgctttaatc acggcgcaca accgcctgtg    11460
cagtcggccc ttgatggtaa aaccatccct cactggtatc gcatgattaa ccgtctgatg    11520
tggatctggc gcggcattga cccacgcgaa atcctcgacg tccaggcacg tattgtgatg    11580
agcgatgccg aacgtaccga cgatgattta tacgatacgg tgattggcta ccgtggcggc    11640 aactggatt atgagtgggc cccggatctt tgtgaaggaa ccttacttct gtggtgtgac    11700
ataattggac aaactaccta cagagattta aagctctaag gtaaatataa aattttaag    11760 tgtataatgt gttaaactac tgattctaat tgtttgtgta ttttagattc caacctatgg    11820
aactgatgaa tgggagcagt ggtggaatgc ctttaatgag gaaaacctgt tttgctcaga    11880
agaaatgcca tctagtgatg atgaggctac tgctgactct caacattcta ctcctccaaa    11940
aaagaagaga aaggtagaag acccccaagga ctttccttca gaattgctaa gttttttgag    12000
tcatgctgtg tttagtaata gaactcttgc ttgctttgct atttacacca caaaggaaaa    12060
agctgcactg ctatacaaga aaattatgga aaaatattct gtaaccttta taagtaggca    12120
taacagttat aatcataaca tactgttttt tcttactcca cacaggcata gagtgtctgc    12180
tattaataac tatgctcaaa aattgtgtac ctttagcttt ttaatttgta aaggggttaa    12240
taaggaatat ttgatgtata gtgccttgac tagagatcat aatcagccat accacatttg    12300
tagaggtttt acttgcttta aaaaacctcc cacacctccc cctgaacctg aaacataaaa    12360
tgaatgcaat tgttgttgtt aacttgttta ttgcagctta taatggttac aaataaagca    12420
atagcatcac aaatttcaca aataaagcat ttttttcact gcattctagt tgtggtttgt    12480
ccaaactcat caatgtatct tatcatgtct ggatcaactg gataactcaa gctaaccaaa    12540
atcatcccaa acttcccacc ccatacccta ttaccactgc caattacctg tggtttcatt    12600
tactctaaac ctgtgattcc tctgaattat tttcatttta aagaaattgt atttgttaaa    12660
tatgtactac aaacttagta gt                                             12682
```

<210> SEQ ID NO 52
<211> LENGTH: 12378
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 52

| | | | | | |
|---|---|---|---|---|---|
| gaatgcaatt | gttgttgtta | acttgtttat | tgcagcttat | aatggttaca | aataaagcaa | 60 |
| tagcatcaca | aatttcacaa | ataaagcatt | tttttcactg | cattctagtt | gtggtttgtc | 120 |
| caaactcatc | aatgtatctt | atcatgtctg | gatcaactgg | ataactcaag | ctaaccaaaa | 180 |
| tcatcccaaa | cttcccaccc | catacccctat | taccactgcc | aattacctgt | ggtttcattt | 240 |
| actctaaacc | tgtgattcct | ctgaattatt | tcattttaa | agaaattgta | tttgttaaat | 300 |
| atgtactaca | aacttagtag | ttggaagggc | taattcactc | ccaaagaaga | caagatatcc | 360 |
| ttgatctgtg | gatctaccac | acacaaggct | acttccctga | ttagcagaac | tacacaccag | 420 |
| ggccagggtc | agatatccac | tgacctttgg | atggtgctac | aagctagtac | cagttgagcc | 480 |
| agataaggta | gaagaggcca | ataaggaga | gaacaccagc | ttgttacacc | ctgtgagcct | 540 |
| gcatgggatg | gatgacccgg | agagagaagt | gttagagtgg | aggtttgaca | gccgcctagc | 600 |
| atttcatcac | gtggcccgag | agctgcatcc | ggagtacttc | aagaactgct | gatatcgagc | 660 |
| ttgctacaag | ggactttccg | ctggggactt | tccagggagg | cgtggcctgg | gcgggactgg | 720 |
| ggagtggcga | gccctcagat | cctgcatata | agcagctgct | ttttgcctgt | actgggtctc | 780 |
| tctggttaga | ccagatctga | gcctgggagc | tctctggcta | actagggaac | ccactgctta | 840 |
| agcctcaata | aagcttgcct | tgagtgcttc | aagtagtgtg | tgcccgtctg | ttgtgtgact | 900 |
| ctggtaacta | gagatccctc | agacccttt | agtcagtgtg | gaaaatctct | agcagtggcg | 960 |
| cccgaacagg | gacttgaaag | cgaaagggaa | accagaggag | ctctctcgac | gcaggactcg | 1020 |
| gcttgctgaa | gcgcgcacgg | caagaggcga | ggggcggcga | ctggtgagta | cgccaaaaat | 1080 |
| tttgactagc | ggaggctaga | aggagagaga | tgggtgcgag | agcgtcagta | ttaagcgggg | 1140 |
| gagaattaga | tcgatgggaa | aaaattcggt | taaggccagg | gggaagaaa | aaatataaat | 1200 |
| taaaacatat | agtatgggca | agcagggagc | tagaacgatt | cgcagttaat | cctggcctgt | 1260 |
| tagaaacatc | agaaggctgt | agacaaatac | tgggacagct | acaaccatcc | cttcagacag | 1320 |
| gatcagaaga | acttagatca | ttatataata | cagtagcaac | cctctattgt | gtgcatcaaa | 1380 |
| ggatagagat | aaaagacacc | aaggaagctt | tagacaagat | agaggaagag | caaaacaaaa | 1440 |
| gtaagaaaaa | agcacagcaa | gcagcagctg | acacaggaca | cagcaatcag | gtcagccaaa | 1500 |
| attaccctat | agtgcagaac | atccaggggc | aaatggtaca | tcaggccata | tcacctagaa | 1560 |
| ctttaaatgc | atgggtaaaa | gtagtagaag | agaaggcttt | cagcccagaa | gtgatacccca | 1620 |
| tgttttcagc | attatcagaa | ggagccaccc | cacaagattt | aaacaccatg | ctaaacacag | 1680 |
| tggggggaca | tcaagcagcc | atgcaaatgt | taaaagagac | catcaatgag | gaagctgcag | 1740 |
| aatgggatag | agtgcatcca | gtgcatgcag | ggcctattgc | accaggccag | atgagagaac | 1800 |
| caaggggaag | tgacatagca | ggaactacta | gtacccttca | ggaacaaata | ggatggatga | 1860 |
| caaataatcc | acctatccca | gtaggagaaa | tttataaaag | atggataatc | ctgggattaa | 1920 |
| ataaaatagt | aagaatgtat | agccctacca | gcattctgga | cataagacaa | ggaccaaaag | 1980 |
| aacccttag | agactatgta | gaccggttct | ataaaactct | aagagccgag | caagcttcac | 2040 |
| aggaggtaaa | aaattggatg | acagaaacct | tgttggtcca | aaatgcgaac | ccagattgta | 2100 |
| agactatttt | aaaagcattg | ggaccagcgg | ctacactaga | agaaatgatg | acagcatgtc | 2160 |

```
agggagtagg aggacccggc cataaggcaa gagttttggc tgaagcaatg agccaagtaa    2220
caaattcagc taccataatg atgcagagag gcaattttag gaaccaaaga aagattgtta    2280
agtgtttcaa ttgtggcaaa gaagggcaca cagccagaaa ttgcagggcc cctaggaaaa    2340
agggctttaa ttaaccgtac gcgtactacg taagaagtac acatcccact agggatgct     2400 agattggtaa taacaacata ttggggtctg catacaggag aaagagactg gcatttgggt    2460
cagggagtct ccatagaatg gaggaaaaag agatatagca cacaagtaga ccctgaacta    2520
gcagaccaac taattcatct gtattacttt gactgttttt cagactctgc tataagaaag    2580
gccttattag gacacatagt tagccctagg tgtgaatatc aagcaggaca taacaaggta    2640
ggatctctac aatacttggc actagcagca ttaataacac caaaaagat aaagccacct     2700 ttgcctagtg ttacgaaact gacagaggat agatggaaca gccccagaa gaccaagggc     2760 cacagaggga gccacacaat gaatggacac tagagctttt agaggagctt aagaatgaag    2820
ctgttagaca ttttcctagg atttggctcc atggcttagg gcaacatatc tatgaaactt    2880
atggggatac ttgggcagga gtggaagcca taataagaat tctgcaacaa ctgctgttta    2940 tccatttca gaattgggtg tcgacatagc agaataggcg ttactcgaca gaggagagca    3000
agaaatggag ccagtagatc ctagactaga gccctggaag catccaggaa gtcagcctaa    3060
aactgcttgt accaattgct attgtaaaaa gtgttgcttt cattgccaag tttgtttcat    3120
aacaaaagcc ttaggcatct cctatggcag gaagaagcgg agacagcgac gaagagctca    3180
tcagaacagt cagactcatc aagcttctct atcaaagcag taagtagtac atgtaacgca    3240
acctatacca atagtagcaa tagtagcatt agtagtagca ataataatag caatagttgt    3300
gtggtccata gtaatcatag aatataggaa aatattaaga caagaaaaa tagacaggtt     3360 aattgataga ctaatagaaa gagcagaaga cagtggcaat gagagtgaag gagaaatatc    3420
agcacttgtg gagatggggg tggagatggg gcaccatgct ccttgggatg ttgatgatct    3480
gtagtgctac agaaaaattg tgggtcacag tctattatgg ggtacctgtg tggaaggaag    3540
caaccaccac tctatttgt gcatcagatg ctaaagcata tgatacagag gtacataatg     3600
tttgggccac acatgcctgt gtacccacag acccccaaccc acaagaagta gtattggtaa    3660
atgtgacaga aaattttaac atgtggaaaa atgacatggt agaacagatg catgaggata    3720
taatcagttt atgggatcaa agcctaaagc catgtgtaaa attaacccca ctctgtgtta    3780
gtttaaagtg cactgatttg aagaatgata ctaataccaa tagtagtagc gggagaatga    3840
taatggagaa aggagagata aaaaactgct ctttcaatat cagcacaagc ataagaggta    3900
aggtgcagaa agaatatgca tttttttata aacttgatat aataccaata gataatgata    3960
ctaccagcta taagttgaca agttgtaaca cctcagtcat tacacaggcc tgtccaaagg    4020 tatccttga gccaattccc atacattatt gtgccccggc tggttttgcg attctaaaat     4080
gtaataataa gacgttcaat ggaacaggac catgtacaaa tgtcagcaca gtacaatgta    4140
cacatggaat taggccagta gtatcaactc aactgctgtt aaatggcagt ctagcagaag    4200
aagaggtagt aattagatct gtcaatttca cggacaatgc taaaaccata atagtacagc    4260
tgaacacatc tgtagaaatt aattgtacaa gacccaacaa caatacaaga aaaagaatcc    4320
gtatccagag aggaccaggg agagcatttg ttacaatagg aaaaatagga aatatgagac    4380
aagcacattg taacattagt agagcaaaat ggaataacac tttaaaacag atagctagca    4440
aattaagaga acaatttgga aataataaaa caataatctt taagcaatcc tcaggagggg    4500
acccagaaat tgtaacgcac agttttaatt gtggagggga atttttctac tgtaattcaa    4560
```

```
cacaactgtt taatagtact tggtttaata gtacttggag tactgaaggg tcaaataaca    4620
ctgaaggaag tgacacaatc accctcccat gcagaataaa acaaattata aacatgtggc    4680
agaaagtagg aaaagcaatg tatgcccctc ccatcagtgg acaaattaga tgttcatcaa    4740
atattacagg gctgctatta acaagagatg gtggtaatag caacaatgag tccgagatct    4800
tcagacctgg aggaggagat atgagggaca attggagaag tgaattatat aaatataaag    4860
tagtaaaaat tgaaccatta ggagtagcac ccaccaaggc aaagagaaga gtggtgcaga    4920
gagaaaaaag agcagtggga ataggagctt tgttccttgg gttcttggga gcagcaggaa    4980
gcactatggg cgcagcgtca atgacgctga cggtacaggc cagacaatta ttgtctggta    5040
tagtgcagca gcagaacaat ttgctgaggg ctattgaggc gcaacagcat ctgttgcaac    5100
tcacagtctg gggcatcaag cagctccagg caagaatcct ggctgtggaa agatacctaa    5160
aggatcaaca gctcctgggg atttggggtt gctctggaaa actcatttgc accactgctg    5220
tgccttggaa tgctagttgg agtaataaat ctctggaaca gatttggaat cacacgacct    5280
ggatggagtg ggacagagaa attaacaatt acacaagctt aatacactcc ttaattgaag    5340
aatcgcaaaa ccagcaagaa aagaatgaac aagaattatt ggaattagat aaatgggcaa    5400
gtttgtggaa ttggtttaac ataacaaatt ggctgtggta tataaaatta ttcataatga    5460
tagtaggagg cttggtaggt ttaagaatag ttttgctgt actttctata gtgaatagag    5520
ttaggcaggg atattcacca ttatcgtttc agacccacct cccaaccccg aggggacccg    5580
acaggcccga aggaatagaa gaagaaggtg gagagagaga cagagacaga tccattcgat    5640
tagtgaacgg atccttagca cttatctggg acgatctgcg gagcctgtgc ctcttcagct    5700
accaccgctt gagagactta ctcttgattg taacgaggat tgtggaactt ctgggacgca    5760
gggggtggga agccctcaaa tattggtgga atctcctaca atattggagt caggagctaa    5820
agaatagtgc tgttagcttg ctcaatgcca cagccatagc agtagctgag gggacagata    5880
gggttataga agtagtacaa ggagcttgta gagctattcg ccacatacct agaagaataa    5940
gacagggctt ggaaaggatt ttgctataag atgggtggcg cggccgcaat ggtgagcaag    6000
ggcgaggagc tgttcaccgg ggtggtgccc atcctggtcg agctggacgg cgacgtaaac    6060
ggccacaagt tcagcgtgtc cggcgagggc gagggcgatg ccacctacgg caagctgacc    6120
ctgaagttca tctgcaccac cggcaagctg cccgtgccct ggcccaccct cgtgaccacc    6180
ctgacctacg gcgtgcagtg cttcagccgc taccccgacc acatgaagca gcacgacttc    6240
ttcaagtccg ccatgcccga aggctacgtc caggagcgca ccatcttctt caaggacgac    6300
ggcaactaca agacccgcgc cgaggtgaag ttcgagggcg acaccctggt gaaccgcatc    6360
gagctgaagg gcatcgactt caaggaggac ggcaacatcc tggggcacaa gctggagtac    6420
aactacaaca gccacaacgt ctatatcatg gccgacaagc agaagaacgg catcaaggcg    6480
aacttcaaga tccgccacaa catcgaggac ggcagcgtgc agctcgccga ccactaccag    6540
cagaacaccc ccatcggcga cggccccgtg ctgctgcccg acaaccacta cctgagcacc    6600
cagtccgccc tgagcaaaga ccccaacgag aagcgcgatc acatggtcct gctggagttc    6660
gtgaccgccg ccgggatcac tctcggcatg gacgagctgt acaagtaaga attctgactc    6720
gagacctaga aaaacatgga gcaatcacaa gtagcaatac agcagctacc aatgctgatt    6780
gtgcctggct agaagcacaa gaggaggagg aggtgggttt tccagtcaca cctcaggtac    6840
ctttaagacc aatgacttac aaggcagctg tagatcttag ccactttta aaagaaaagg    6900
```

```
gggggactgga aagggctaatt cactcccaac gaagacaaga tatccttgat ctgtggatct    6960
accacacaca aggctacttc cctgattggc agaactacac accagggcca gggatcagat    7020
atccactgac ctttggatgg tgctacaagc tagtaccagt tgagcaagag aaggtagaag    7080
aagccaatga aggagagaac acccgcttgt tacaccctgt gagcctgcat gggatggatg    7140
acccggagag agaagtatta gagtggaggt ttgacagccg cctagcattt catcacatgg    7200
cccgagagct gcatccggag tacttcaaga actgctgaca tcgagcttgc tacaagggac    7260
tttccgctgg ggactttcca gggaggcgtg gcctgggcgg gactggggag tggcgagccc    7320
tcagatgctg catataagca gctgcttttt gcttgtactg ggtctctctg gttagaccag    7380
atctgagcct gggagctctc tggctaacta gggaacccac tgcttaagcc tcaataaagc    7440
ttgccttgag tgcttcaagt agtgtgtgcc cgtctgttgt gtgactctgg cgcgcctcta    7500
gaattaattc cgtgtattct atagtgtcac ctaaatcgta tgtgtatgat acataaggtt    7560
atgtattaat tgtagccgcg ttctaacgac aaatatgtaca agcctaattg tgtagcatct    7620
ggcttactga agcagaccct atcatctctc tcgtaaactg ccgtcagagt cggtttggtt    7680
ggacgaacct tctgagtttc tggtaacgcc gtcccgcacc cggaaatggt cagcgaacca    7740
atcagcaggg tcatcgctag ccagatcctc tacgccggac gcatcgtggc cggcatcacc    7800
ggcgccacag gtgcggttgc tggcgcctat atcgccgaca tcaccgatgg ggaagatcgg    7860
gctcgccact tcgggctcat gagcgcttgt ttcggcgtgg gtatggtggc aggccccgtg    7920 gccggggggac tgtttgggcgc catctccttg catgcaccat tccttgcggc ggcggtgctc    7980
aacggcctca acctactact gggctgcttc ctaatgcagg agtcgcataa gggagagcgt    8040
cgaatggtgc actctcagta caatctgctc tgatgccgca tagttaagcc agccccgaca    8100
cccgccaaca cccgctgacg cgccctgacg ggcttgtctg ctcccggcat ccgcttacag    8160
acaagctgtg accgtctccg ggagctgcat gtgtcagagg ttttcaccgt catcaccgaa    8220
acgcgcgaga cgaaagggcc tcgtgatacg cctattttta taggttaatg tcatgataat    8280
aatggtttct tagacgtcag gtggcacttt tcggggaaat gtgcgcggaa cccctatttg    8340
tttatttttc taaatacatt caaatatgta tccgctcatg agacaataac cctgataaat    8400
gcttcaataa tattgaaaaa ggaagagtat gagtattcaa catttccgtg tcgcccttat    8460
tccctttttt gcggcatttt gccttcctgt ttttgctcac ccagaaacgc tggtgaaagt    8520
aaaagatgct gaagatcagt tgggtgcacg agtgggttac atcgaactgg atctcaacag    8580
cggtaagatc cttgagagtt ttcgccccga agaacgtttt ccaatgatga gcactttaa    8640 agttctgcta tgtggcgcgg tattatcccg tattgacgcc gggcaagagc aactcggtcg    8700
ccgcatacac tattctcaga atgacttggt tgagtactca ccagtcacag aaaagcatct    8760
tacggatggc atgacagtaa gagaattatg cagtgctgcc ataaccatga gtgataacac    8820
tgcggccaac ttacttctga caacgatcgg aggaccgaag gagctaaccg cttttttgca    8880
caacatgggg gatcatgtaa ctcgccttga tcgttgggaa ccggagctga atgaagccat    8940
accaaacgac gagcgtgaca ccacgatgcc tgtagcaatg gcaacaacgt tgcgcaaact    9000
attaactggc gaactactta ctctagcttc ccggcaacaa ttaatagact ggatggaggc    9060
ggataaagtt gcaggaccac ttctgcgctc ggcccttccg gctggctggt ttattgctga    9120
taaatctgga gccggtgagc gtgggtctcg cggtatcatt gcagcactgg ggccagatgg    9180
taagccctcc cgtatcgtag ttatctacac gacggggagt caggcaacta tggatgaacg    9240
aaatagacag atcgctgaga taggtgcctc actgattaag cattggtaac tgtcagacca    9300
```

```
agtttactca tatatacttt agattgattt aaaacttcat ttttaattta aaaggatcta   9360
ggtgaagatc cttttgata atctcatgac caaaatccct taacgtgagt tttcgttcca    9420
ctgagcgtca gaccccgtag aaaagatcaa aggatcttct tgagatcctt tttttctgcg   9480
cgtaatctgc tgcttgcaaa caaaaaaacc accgctacca gcggtggttt gtttgccgga   9540
tcaagagcta ccaactcttt ttccgaaggt aactggcttc agcagagcgc agataccaaa   9600
tactgttctt ctagtgtagc cgtagttagg ccaccacttc aagaactctg tagcaccgcc   9660
tacataccte gctctgctaa tcctgttacc agtggctgct gccagtggcg ataagtcgtg   9720
tcttaccggg ttggactcaa gacgatagtt accggataag gcgcagcggt cgggctgaac   9780
ggggggttcg tgcacacagc ccagcttgga gcgaacgacc tacaccgaac tgagatacct   9840
acagcgtgag ctatgagaaa gcgccacgct tcccgaaggg agaaaggcgg acaggtatcc   9900
ggtaagcggc agggtcggaa caggagagcg cacgagggag cttccagggg gaaacgcctg   9960
gtatctttat agtcctgtcg ggtttcgcca cctctgactt gagcgtcgat ttttgtgatg  10020
ctcgtcaggg gggcggagcc tatggaaaaa cgccagcaac gcggccttt tacggttcct  10080
ggccttttgc tggccttttg ctcacatgtt ctttcctgcg ttatccctg attctgtgga  10140
taaccgtatt accgcctttg agtgagctga taccgctcgc cgcagccgaa cgaccgagcg  10200
cagcgagtca gtgagcgagg aagcggaaga gcgcccaata cgcaaaccgc ctctccccgc  10260
gcgttggccg attcattaat gcagctgtgg aatgtgtgtc agttagggtg tggaaagtcc  10320
ccaggctccc cagcaggcag aagtatgcaa agcatgcatc tcaattagtc agcaaccagg  10380
tgtggaaagt ccccaggctc cccagcaggc agaagtatgc aaagcatgca tctcaattag  10440
tcagcaacca tagtcccgcc cctaactccg cccatcccgc ccctaactcc gcccagttcc  10500
gcccattctc cgccccatgg ctgactaatt ttttttattt atgcagaggc cgaggccgcc  10560
tcggcctctg agctattcca gaagtagtga ggaggctttt ttggaggcct aggcttttgc  10620
aaaaagcttg gacacaagac aggcttgcga gatatgtttg agaataccac tttatcccgc  10680
gtcagggaga ggcagtgcgt aaaaagacgc ggactcatgt gaaatactgg ttttagtgc   10740
gccagatctc tataatctcg cgcaacctat ttcccctcg aacactttt aagccgtaga   10800
taaacaggct gggacacttc acatgagcga aaaatacatc gtcacctggg acatgttgca  10860
gatccatgca cgtaaactcg caagccgact gatgccttct gaacaatgga aaggcattat  10920
tgccgtaagc cgtggcggtc tggtaccggg tgcgttactg gcgcgtgaac tgggtattcg  10980
tcatgtcgat accgtttgta tttccagcta cgatcacgac aaccagcgcg agcttaaagt  11040
gctgaaacgc gcagaaggcg atggcgaagg cttcatcgtt attgatgacc tggtggatac  11100
cggtggtact gcggttgcga ttcgtgaaat gtatccaaaa gcgcactttg tcaccatctt  11160
cgcaaaaccg gctggtcgtc cgctggttga tgactatgtt gttgatatcc gcaagatac   11220
ctggattgaa cagccgtggg atatgggcgt cgtattcgtc ccgccaatct ccggtcgcta  11280
atcttttcaa cgcctggcac tgccgggcgt tgttcttttt aacttcaggc gggttacaat  11340
agtttccagt aagtattctg gaggctgcat ccatgacaca gcaaacctg agcgaaaccc   11400
tgttcaaacc ccgctttaaa catcctgaaa cctcgacgct agtccgccgc tttaatcacg  11460
gcgcacaacc gcctgtgcag tcggcccttg atggtaaaac catccctcac tggtatcgca  11520
tgattaaccg tctgatgtgg atctggcgcg gcattgaccc acgcgaaatc ctcgacgtcc  11580
aggcacgtat tgtgatgagc gatgccgaac gtaccgacga tgatttatac gatacggtga  11640
```

```
ttggctaccg tggcggcaac tggatttatg agtgggcccc ggatctttgt gaaggaacct    11700
tacttctgtg gtgtgacata attggacaaa ctacctacag agatttaaag ctctaaggta    11760
aatataaaat ttttaagtgt ataatgtgtt aaactactga ttctaattgt ttgtgtattt    11820
tagattccaa cctatggaac tgatgaatgg gagcagtggt ggaatgcctt taatgaggaa    11880
aacctgtttt gctcagaaga aatgccatct agtgatgatg aggctactgc tgactctcaa    11940
cattctactc ctccaaaaaa gaagagaaag gtagaagacc ccaaggactt tccttcagaa    12000
ttgctaagtt ttttgagtca tgctgtgttt agtaatagaa ctcttgcttg ctttgctatt    12060
tacaccacaa aggaaaaagc tgcactgcta tacaagaaaa ttatggaaaa atattctgta    12120
acctttataa gtaggcataa cagttataat cataacatac tgttttttct tactccacac    12180
aggcatagag tgtctgctat taataactat gctcaaaaat tgtgtacctt tagcttttta    12240
atttgtaaag gggttaataa ggaatatttg atgtatagtg ccttgactag agatcataat    12300
cagccatacc acatttgtag aggttttact tgctttaaaa aacctcccac acctcccct    12360 gaacctgaaa cataaaat                                                  12378

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gcccctagga aaagggctg ttgg                                            24

<210> SEQ ID NO 54
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ctaggaaaaa gggctgttgg aaatg                                          25

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
gtactggatg tgggtgatgc                                                20

<210> SEQ ID NO 56
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
gtgggaaaat tgaattggg                                                 19
```

```
<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
gccacctgga ttcctgagtg                                                   20

<210> SEQ ID NO 58
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58 ctcctttttag ctgacattta tcac                                             24

<210> SEQ ID NO 59
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
gcttgcatgc ctgcaggtcg actctagagg atccccgggt accgagctcg aattcgtaat       60
catggtcata                                                              70

<210> SEQ ID NO 60
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
ctgcagacac gttaacacac actagtacac gtcgacacag aattc                       45

<210> SEQ ID NO 61
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
ctgcagacac gttaacacac actagtacac gtcgacacac gaattc                      46

<210> SEQ ID NO 62
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
gcgtactacg taagaagtac acatccc                                           27
```

```
<210> SEQ ID NO 63
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
tctctagcag tggcgcccga aca                                              23

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
aagttcagaa gtacacatcc c                                                21

<210> SEQ ID NO 65
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
gtacggttaa ttaacgccac tgctagaga                                        29

<210> SEQ ID NO 66
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
gctctattag atacaggagc agatg                                            25

<210> SEQ ID NO 67
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
gtacggttaa ttaatgtatc taatagagc                                        29

<210> SEQ ID NO 68
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
gcgtactacg tataaagcca ggaatgg                                          27
```

```
<210> SEQ ID NO 69
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
tggaaaatct ctagcagtgg cg                                              22

<210> SEQ ID NO 70
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
agtaaaatta aagccaggaa tgg                                             23

<210> SEQ ID NO 71
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
gtacggttaa ttaagctaga gattttcca                                       29

<210> SEQ ID NO 72
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
ctaggaaaaa gggctgttgg aaatg                                           25

<210> SEQ ID NO 73
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
gtacggttaa ttaaagccct ttttcctag                                       29
```